US007700097B2

(12) United States Patent
Braslawsky et al.

(10) Patent No.: US 7,700,097 B2
(45) Date of Patent: Apr. 20, 2010

(54) PURIFICATION AND PREFERENTIAL SYNTHESIS OF BINDING MOLECULES

(75) Inventors: Gary R. Braslawsky, San Diego, CA (US); Scott Glaser, San Diego, CA (US); Tzung-Horng Yang, San Diego, CA (US); Jennifer Hopp, San Marcos, CA (US); Paul Chinn, Carlsbad, CA (US)

(73) Assignee: Biogen Idec MA Inc., Cambridge, MA (US)

( * ) Notice: Subject to any disclaimer, the term of this patent is extended or adjusted under 35 U.S.C. 154(b) by 144 days.

(21) Appl. No.: 10/880,320

(22) Filed: Jun. 28, 2004

(65) Prior Publication Data

US 2005/0163783 A1 Jul. 28, 2005

Related U.S. Application Data

(60) Provisional application No. 60/483,877, filed on Jun. 27, 2003, provisional application No. 60/508,810, filed on Oct. 3, 2003, provisional application No. 60/515,351, filed on Oct. 28, 2003, provisional application No. 60/516,030, filed on Oct. 30, 2003.

(51) Int. Cl.
*A61K 39/00* (2006.01)
*C12P 21/08* (2006.01)
*C07K 16/28* (2006.01)
*C07K 16/18* (2006.01)

(52) U.S. Cl. .............. 424/133.1; 424/134.1; 424/142.1; 424/143.1; 424/155.1; 530/324; 530/387.3; 530/388.22; 530/387.7; 530/388.8

(58) Field of Classification Search .................. None
See application file for complete search history.

(56) References Cited

U.S. PATENT DOCUMENTS

| | | |
|---|---|---|
| 5,041,533 A | 8/1991 | Wunsch et al. |
| 5,166,322 A | 11/1992 | Shaw et al. |
| 5,206,344 A | 4/1993 | Katre et al. |
| 5,208,020 A | 5/1993 | Chari et al. |
| 5,219,996 A | 6/1993 | Bodmer et al. |
| 5,348,876 A * | 9/1994 | Michaelsen et al. ......... 435/326 |
| 5,624,821 A | 4/1997 | Winter et al. |
| 5,641,870 A | 6/1997 | Rinderknecht et al. |
| 5,648,260 A | 7/1997 | Winter et al. |
| 5,677,425 A | 10/1997 | Bodmer et al. |
| 5,714,149 A | 2/1998 | Rhind et al. |
| 5,766,897 A | 6/1998 | Braxton |
| 5,821,333 A | 10/1998 | Carter et al. |
| 5,834,597 A | 11/1998 | Tso et al. |
| 5,837,821 A | 11/1998 | Wu |
| 5,877,291 A | 3/1999 | Mezes et al. |
| 5,892,019 A | 4/1999 | Schlom et al. |
| 5,959,083 A | 9/1999 | Bosslet et al. |
| 5,976,845 A | 11/1999 | Mezes et al. |
| 6,063,905 A | 5/2000 | Capra et al. |
| 6,066,719 A | 5/2000 | Zapata |
| 6,071,515 A | 6/2000 | Mezes et al. |
| 6,136,313 A | 10/2000 | Stevenson et al. |
| 6,165,476 A | 12/2000 | Strom et al. |
| 6,207,815 B1 | 3/2001 | Mezes et al. |
| 6,214,984 B1 | 4/2001 | Zapata |
| 6,218,149 B1 | 4/2001 | Morrison et al. |
| 6,284,536 B1 | 9/2001 | Morrison et al. |
| 6,329,507 B1 | 12/2001 | Mezes et al. |
| 6,348,581 B1 | 2/2002 | Anderson et al. |
| 6,495,137 B1 | 12/2002 | Mezes et al. |
| 6,552,170 B1 | 4/2003 | Thompson et al. |
| 6,576,746 B2 | 6/2003 | McBride et al. |
| 6,642,356 B1 | 11/2003 | Humphreys et al. |
| 6,737,056 B1 | 5/2004 | Presta |
| 6,759,518 B1 | 7/2004 | Kontermann et al. |
| 7,026,446 B1 | 4/2006 | Atwell et al. |
| 7,247,302 B1 | 7/2007 | Rosok et al. |

(Continued)

FOREIGN PATENT DOCUMENTS

EP 0327378 B1 11/1996

(Continued)

OTHER PUBLICATIONS

Santo et al, Clin Cancer Res 5(10): 3118-3123s, Oct. 1999.*
Alta et al, FEBS Letters 454: 90-94, 1999.*
Hudson et al, J. Immunological Method 231: 177-189, 1999.*
Shopes et al, J Immunology 148: 2918-2922, May 1992.*
Translation and sequence alignment of WO 02/22680 A2 above.*
International Search Report for Application No. PCT/US2006/000502, dated Aug. 2, 2006.
International Search Report for Application No. PCT/US2006/000505, dated Aug. 8, 2006.
Aalberse, R.C., et al. "IgG4 breaking the rules." *Immunology*. 2002; 105:9-19.

(Continued)

*Primary Examiner*—Phuong Huynh
(74) *Attorney, Agent, or Firm*—Lahive & Cockfield, LLP; Megan E. Williams

(57) ABSTRACT

The instant invention describes methods of separating or preferentially synthesizing dimers which are linked via at least one interchain disulfide linkage from dimers which are not linked via at least one interchain disulfide linkage from a mixture comprising the two types of polypeptide dimers. These forms can be separated from each other using hydrophobic interaction chromatography. In addition, the invention pertains to connecting peptides that result in the preferential biosynthesis of dimers that are linked via at least one interchain disulfide linkage or that are not linked via at least one interchain disulfide linkage. The invention also pertains to compositions in which a majority of the dimers are linked via at least one interchain disulfide linkage or are not linked via at least one interchain disulfide linkage. The invention still further pertains to novel binding molecules, e.g., comprising connecting peptides of the invention.

38 Claims, 36 Drawing Sheets

U.S. PATENT DOCUMENTS

| | | | |
|---|---|---|---|
| 7,276,585 | B2 | 10/2007 | Lazar et al. |
| 7,317,091 | B2 | 1/2008 | Lazar et al. |
| 2002/0002271 | A1 | 1/2002 | Rinderknecht et al. |
| 2002/0009446 | A1 | 1/2002 | Magilavy |
| 2002/0028486 | A1 | 3/2002 | Morrison et al. |
| 2002/0037558 | A1* | 3/2002 | Lo et al. |
| 2002/0062010 | A1 | 5/2002 | Arathoon et al. |
| 2003/0060444 | A1 | 3/2003 | Finney et al. |
| 2003/0078385 | A1 | 4/2003 | Arathoon et al. |
| 2003/0207346 | A1 | 11/2003 | Arathoon et al. |
| 2004/0033511 | A1 | 2/2004 | Pfizenmaier et al. |
| 2004/0101905 | A1 | 5/2004 | Brekke et al. |
| 2004/0146940 | A1 | 7/2004 | Sanicola-Nadel et al. |
| 2004/0176576 | A1 | 9/2004 | McKenzie et al. |
| 2005/0097625 | A1 | 5/2005 | Meade et al. |
| 2005/0152894 | A1 | 7/2005 | Krummen et al. |
| 2007/0269371 | A1 | 11/2007 | Krummen et al. |

FOREIGN PATENT DOCUMENTS

| | | | |
|---|---|---|---|
| EP | 0327378 | B1 | 12/1996 |
| WO | WO-88/07089 | A1 | 9/1988 |
| WO | WO-89/07142 | A1 | 8/1989 |
| WO | WO-94/09817 | A1 | 5/1994 |
| WO | WO-94/20625 | A1 | 9/1994 |
| WO | WO-94/29351 | A2 | 12/1994 |
| WO | WO-95/09917 | A1 | 4/1995 |
| WO | WO 95/22389 | | 8/1995 |
| WO | WO 97/11370 | | 3/1997 |
| WO | WO-97/44362 | A1 | 11/1997 |
| WO | WO-98/05787 | A1 | 2/1998 |
| WO | WO-98/23289 | A1 | 6/1998 |
| WO | WO-99/15549 | A2 | 4/1999 |
| WO | WO-99/58572 | A1 | 11/1999 |
| WO | WO 02/22680 | A2 * | 3/2002 |
| WO | WO-02/30986 | A2 | 4/2002 |
| WO | WO-02/44215 | A2 | 6/2002 |
| WO | WO-02/060955 | A2 | 8/2002 |
| WO | WO 02/060955 | A2 | 8/2002 |
| WO | WO-02/088170 | A2 | 11/2002 |
| WO | WO 02/096948 | A2 | 12/2002 |
| WO | WO-02/096948 | A2 | 12/2002 |
| WO | WO-2004/026427 | A2 | 4/2004 |
| WO | WO 2004/029207 | A2 | 4/2004 |
| WO | WO-2004/042017 | A2 | 5/2004 |
| WO | WO-2004/074434 | A2 | 9/2004 |
| WO | WO-2004/099249 | A2 | 11/2004 |
| WO | WO-2005/000899 | A2 | 1/2005 |
| WO | WO-2005/007809 | A2 | 1/2005 |
| WO | WO-2005/027966 | A2 | 3/2005 |
| WO | WO-2005/092927 | A1 | 10/2005 |
| WO | WO-2007/010231 | A1 | 1/2007 |

OTHER PUBLICATIONS

Angal, S., et al. "A Single Amino Acid Substitution Abolishes the Heterogeneity of Chimeric Mouse/Human (IgG4) Antibody." *Molecular Immunology.* 1993; 30(1):105-8.

Caron, P.C., et al. "Engineered Humanized Dimeric Forms of IgG Are More Effective Antibodies." *J. Exp. Med.* Oct. 1992; 176:1191-95.

Chintalacharuvu, K.R., et al. "Cysteine Residues Required for the Attachment of the Light Chain in Human IgA2$^1$." *The Journal of Immunology.* 2002; 169; 5072-77.

Coloma, M.J., et al. "Design and production of novel tetravalent bispecific antibodies." *Nature Biotechnology.* Feb. 1997; 15:159-63.

Coloma, M.J., et al. "The Hinge as a Spacer Contributes to Covalent Assembly and Is Required for Function of IgG$^1$." *The Journal of Immunology.* 1997; 158:733-40.

de Kruif, J., et al. "Leucine Zipper Dimerized Bivalent and Bispecific scFv Antibodies from a Semi-synthetic Antigody Phage Display Library." *The Journal of Biological Chemistry.* Mar. 29, 1996; 271(13):7630-34.

Hu, S., et al. "Minibody: A Novel Engineered Anti-Carcinoembryonic Antigen Antibody Fragment (Single-Chain Fv-$C_H3$) Which Exhibits Rapid, High-Level Targeting of Xenografts." *Cancer Research.* Jul. 1, 1996; 56:3055-61.

Inouye, K., et al. "Single-step purification of F(ab')$_{2\mu}$ fragments of mouse monoclonal antibodies (immunoglobulins M) by hydrophobic ingteraction high-performance liquid chromatography using TSKgel Ether-5PW." *Journal of Biochemical and Biophysical Methods.* 1993; 26:27-39.

Jendreyko, N., et al. "Intradiabodies, Bispecific, Tetravalent Antibodies for the Simultaneous Functional Knockout of Two Cell Surface Receptors." *The Journal of Biological Chemistry.* Nov. 28, 2003; 278(48):47812-19.

Lee, C.V., et al. "Bivalent antibody phage display mimics natural immunoglobulin." *Journal of Immunological Methods.* 2004; 284:119-32.

Lund, J., et al. "Multiple Interactions of IgG with Its Core Oligosaccharide Can Modulate Recognition by Complement and Human Fcγ Receptor I and Influence the Synthesis of Its Oligosacharide Chains." *The Journal of Immunology.* 1996; 157:4963-69.

Michaelsen, T.E., et al. "Antibody Dependent Cell-Mediated Cytotoxicity Induced by Chimeric Mouse-Human IgG Subclasses and IgG3 Antibodies with Altered Hinge Region." *Molecular Immunology.* 1992; 29(3):319-26.

Morimoto, K., et al. "Method for the preparation of bispecific F(ab')2μ fragments from mouse monoclonal antibodies of the immunoglobulin M class and characterization of the fragments." *Journal of Immunological Methods.* 1999; 224:43-50.

Morimoto, K., et al. "Single-step purification of F(ab')$_2$ fragments of mouse monoclonal antibodies (immunoglobulins G1) by hydrophobic interaction high performance liquid chromatography using TSKgel Phenyl-5PW." *Journal of Biochemical and Biophysical Methods.* 1992; 24:107-17.

Norderhaug, L., et al. "Chimeric mouse human IgG3 antibodies with an IgG4-like hinge region induce complement-mediated lysis more efficiently than IgG3 with normal hinge." *Eur. J. Immunol.* 1991; 21:2379-84.

Roux, K.H., et al. "Comparisons of the Ability of Human IgG3 Hinge Mutants, IgM, IgE, and IgA2, to Form Small Immune Complexes: A Role for Flexibility and Geometry." *The Journal of Immunology.* 1998; 161:4083-90.

Schuuman, J., et al. "The inter-heavy chain disulfide bonds of IgG4 are in equilibrium with intra-chain disulfide bonds." *Molecular Immunology.* 2001; 38:1-8.

Adams, Gregory P., et al., "Highly Specific in Vivo Tumor Targeting by Monovalent and Divalent Forms of 741F8 Anti-c-*erbB*-2 Single-Chain Fv$^1$," *Cancer Research*, vol. 53:4026-4034 (1993).

Alt, Margitta, et al., "Novel tetravalent and bispecific IgG-like antibody molecules combining single-chain diabodies with the immunoglobulin γl Fc or CH3 region," *FEBS Letters*, vol. 454:90-94 (1999).

Benhar, Itai, et al., "*Pseudomonas* Exotoxin A Mutants," *The Journal of Biological Chemistry*, vol. 269(18):13398-13404 (1994).

Bera, Tapan K., et al., "A Bivalent Disulfide-stabilized Fv with Improved Antigen Binding to erbB2," *J. Mol. Biol.*, vol. 281:475-483 (1998).

Bloom, James W., et al., "Interchain disulfide bond in the core hinge region of human IgG4," *Protein Science*, vol. 6:407-415 (1997).

Brekke, Ole Henrik, et al., "The structural requirements for complement activation by IgG: does it hinge on the hinge?" *Immunology Today*, vol. 16(2):85-90 (1995).

Carter, Paul, et al., "Engineering antibodies for imaging and therapy," *Current Opinion in Biotechnology*, vol. 8:449-454 (1997).

Dorai, Haimanti, et al., "Role of Inter-heavy and Light Chain Disulfide Bonds in the Effector Functions of Human Immunoglobulin IgG1," *Molecular Immunology*, vol. 29(12):1487-1491 (1992).

Chintalacharuvu, Koteswara R., et al., "Production and characterization of recombinant IgA," *Immunotechnology*, vol. 4:165-174 (1999).

Chintalacharuvu, Koteswara R., et al., "Hybrid IgA2/IgG1 Antibodies with Tailor-Made Effector Functions," *Clinical Immunology*, vol. 101(1):21-31 (2001).

Chintalacharuvu, Koteswara R., et al., "Residues Critical for H-L Disulfide Bond Formation in Human IgA1 and IgA2[1]," *The Journal of Immunology*, vol. 157:3443-3449 (1996).

Chintalacharuvu, Koteswara R., et al., "Cysteine Residues Required for the Attachment of the Light Chain in Human IgA2[1]," *Journal of Immunology*, vol. 169:5072-5077 (2002).

FitzGerald, Kevin, et al., "Improved tumour targeting by disulphide stabilized diabodies expressed in *Pichia pastoris*," *Protein Engineering*, vol. 10(10):1221-1225 (1997).

Gillies, Stephen D., et al., "Antigen binding and biological activities of engineered mutant chimeric antibodies with human tumor specificities," *Hum. Antibod. Hybridomas*, vol. 1(1):47-54 (1990).

Glockshuber, Rudi, et al., "A Comparison of Strategies To Stabilize Immunoglobulin $F_v$-Fragments," *Biochemistry*, vol. 29:1362-1367 (1990).

Guan, Lufeng, et al., "Homogeneous immunoconjugates for boron neutron-capture therapy: Design, synthesis, and preliminary characterization," *Proc. Natl. Acad. Sci. USA*, vol. 95:13206-13210 (1998).

Haran, G., et al., "Domain motions in phosphoglycerate kinase: Determination of interdomain distance distributions by site-specific labeling and time-resolved fluorescence energy transfer," *Proc. Natl. Acad. Sci. USA*, vol. 89:11764-11768 (1992).

Hudson, Peter J., "Recombinant antibody constructs in cancer therapy," *Current Opinion in Immunology*, vol. 11:548-557 (1999).

Humphreys, David P., et al., "$F(ab')_2$ molecules made from *Escherichia coli* produced Fab' with hinge sequences conferring increased serum survival in an animal model," *Journal of Immunological Methods*, vol. 217:1-10 (1998).

Jue, Rodney, et al., "Addition of Sulfhydryl Groups to *Escherichia coli* Ribosomes by Protein Modification with 2-Iminothiolane (Methyl 4-Mercaptobutyrimidate)," *Biochemistry*, vol. 17(25):5399-5406 (1978).

Kipriyanov, Sergey M., et al., "Bacterial Expression and Refolding of Single-Chain Fv Fragments with C-Terminal Cysteines," *Cell Biophysics*, vol. 26:187-204 (1995).

Kreitman, Robert J., et al., "Site-Specific Conjugation to Interleukin 4 Containing Mutated Cysteine Residues Produces Interleukin 4-Toxin Conjugates with Improved Binding and Activity," *Biochemistry*, vol. 33:11637-11644 (1994).

Lee, Hyun-Sil, et al., "Generation and characterization of a novel single-gene-encoded single-chain immunoglobulin molecule with antigen binding activity and effector functions," *Molecular Immunology*, vol. 36:61-71 (1999).

Lyons, Alan, et al., "Site-specific attachment to recombinant antibodies via introduced surface cysteine residues," *Protein Engineering*, vol. 3(8):703-708 (1990).

Olafsen, Tove, et al., "Covalent disulfide-linked anti-CEA diabody allows site-specific conjugation and radiolabeling for tumor targeting applications," *Protein Engineering, Design & Selection*, vol. 17(1):21-27 (2004).

Palmer, Michael, et al., "*Staphylococcus aureus* α-Toxin," *The Journal of Biological Chemistry*, vol. 268(16):11959-11962 (1993).

Queiroz, J.A., et al., "hydrophobic interaction chromatography of proteins," *Journal of Biotechnology*, vol. 87:143-159 (2001).

Reff, Mitchell E., et al., "A review of modifications to recombinant antibodies: attempt to increase efficacy in oncology applications," *Critical Reviews in Oncology/Hematology*, vol. 40:25-35 (2001).

Reiter, Yoram, et al., "Engineering interchain disulfide bonds into conserved framework regions of Fv Fragments: improved biochemical characteristics of recombinant immunotoxins containing disulfide-stabilized Fv," *Protein Engineering*, vol. 7(5):697-704 (1994).

Shopes, Bob, "A Genetically Engineered Human IgG Mutant with Enhanced Cytolytic Activity," *The Journal of Immunology*, vol. 148(9):2918-2922 (1992).

Shopes, Bob, "A Genetically Engineered Human IgG with Limited Flexibility Fully Initiates Cytolysis via Complement," *Molecular Immunology*, vol. 30(6):603-609 (1993).

Slavin-Chiorini, Dale C., et al., "Biological Properties of Chimeric Domain-deleted Anticarcinoma Immunoglobulin," *Cancer Research*, (Suppl.) vol. 55:5957s-5967s (1995).

Smith, Richard I.F., et al., "Recombinant Polymeric IgG: An Approach to Engineering More Potent Antibodies," *Bio/Technology*, vol. 12:683-688 (1994).

Tsutsumi, Yasuo, et al., "Site-specific chemical modification with polyethylene glycol of recombinant immunotoxin anti-Tac(Fv)-PE38 (LMB-2) improves antitumor activity and reduces animal toxicity and immunogenicity," *PNAS*, vol. 97(15):8548-8553 (2000).

Webber, Keith O., et al., "Preparation and Characterization of a Disulfide-Stabilized Fv Fragment of the Anti-Tac Antibody: Comparison with its Single-Chain Analog," *Molecular Immunology*, vol. 32(4):249-258 (1995).

Yazaki, Paul J., et al., "Mammalian expression and hollow fiber bioreactor production of recombinant anti-CEA diabody and minibody for clinical applications," *Journal of Immunological Methods*, vol. 253:195-208 (2001).

Zhao, Zhan G., et al., "Site-Specific Modification of a Single-Chain Antibody Using a Novel Glyoxylyl-Based Labeling Reagent," *Bioconjugate Chem.*, vol. 10:424-430 (1999).

International Preliminary Report on Patentability for App. No. PCT/US2004/020944, dated Dec. 22. 2005.

International Search Report for App. No. PCT/US2004/020944, dated Feb. 8, 2005.

Adkins, Heather B. et al, "Antibody blockade of the Cripto CFC domain suppresses tumor cell growth in vivo," *The Journal of Clinical Investigation*, vol. 112(4):575-587 (2003).

Brekke, Ole Henrik et al, "The structural requirement for complement activation by IgG: does it hinge on the hinge?" *Immunology Today*, vol. 16(2):85-90 (1995).

Hu, Xiu Feng et al, "Cripto Monoclonal Antibodies," *Drug News Perspect.*, vol. 18(5):293-303 (2005).

LePage, Doreen J. et al, "Inhibition of human tumor xenografts by anti-Cripto antibodies," *Proceedings of the American Association for Cancer Research*, vol. 44:145 (2003) Poster #749.

Leung, Shui-on et al, "The Effects of Domain Deletion, Glycosylation, and Long $IgG_3$ Hinge on the Biodistribution and Serum Stability Properties of a Humanized $IgG_1$ Immunoglobulin, hLL2, and Its Fragments," *Clinical Cancer Research*, vol. 3:3106s-3117s (1999).

Lu, Dan et al, "Di-diabody: a novel tetravalent bispecific antibody molecule by design," *Journal of Immunological Methods*, vol. 279:219-232 (2003).

Plückthun, Andreas et al, "New protein engineering approaches to multivalent and bispecific antibody fragments," *Immunotechnology*, vol. 3:83-105 (1997).

\* cited by examiner

Diagrammatic Representation of the Two Secreted forms of the Domain Deleted Constructs Figure 4A.
Single-stranded DNA sequence of heavy chain CH2 domain-deleted huCC49
Pro243Ala244Pro245 + [Gly/Ser] hinge connecting peptide
CAGGTCCAGCTGGTGCAGTCCGGCGCTGAGGTGGTGAAACCTGGGGCTTC
CGTGAAGATTTCCTGCAAGGCAAGCGGCTACACCTTCACTGATCACGCAA
TCCACTGGGTGAAACAGAATCCTGGACAGCGCCTGGAGTGGATTGGATAT
TTCTCTCCCGGAAACGATGATTTTAAGTACAATGAGAGGTTCAAGGGCAA
GGCCACACTGACTGCAGACACATCTGCCAGCACTGCCTACGTGGAGCTCT
CCAGCCTGAGATCCGAGGATACTGCAGTGTACTTCTGCACAAGATCCCTG
AATATGGCCTACTGGGGACAGGGAACCCTGGTCACCGTCTCCAGCGCTAG
CACCAAGGGCCCATCGGTCTTCCCCCTGGCACCCTCCTCCAAGAGCACCTC
TGGGGGCACAGCGGCCCTGGGCTGCCTGGTCAAGGACTACTTCCCCGAAC
CGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTG
ACCGTGCCCTCCAGCAGCTTGGGCACCCAGACCTACATCTGCAACGTGAA
TCACAAGCCCAGCAACACCAAGGTGGACAAGAAAGTTGAGCCCAAATCTT
GTGACAAAACTCACACATGCCCACCGTGCCCAGCACCTGGAGGTGGCTCG
AGTGGAGGCGGATCCGGAGGGCAGCCCCGAGAACCACAGGTGTACACCC
TGCCCCCATCCCGGGATGAGCTGACCAAGAACCAGGTCAGCCTGACCTGC
CTGGTCAAAGGCTTCTATCCCAGCGACATCGCCGTGGAGTGGGAGAGCAA
TGGGCAGCCGGAGAACAACTACAAGACCACGCCTCCCGTGCTGGACTCCG
ACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAA
CCACTACACGCAGAAGAGCCTCTCCCTGTCTCCGGGTAAATGA Figure 4B.
Single-stranded DNA sequence of light chain CH2 domain-deleted huCC49
GACATCGTGATGAGCCAGTCTCCAGACTCCCTGGCCGTGTCCCTGGGCGA
GAGGGTGACTCTGAATTGCAAGTCCAGCCAGTCCCTGCTCTATAGCGGAA
ATCAGAAGAACTATCTCGCCTGGTATCAGCAGAAACCAGGGCAGAGCCCT
AAACTGCTGATTTACTGGGCATCCGCTAGGGAATCCGGCGTGCCTGATCG
CTTCAGCGGCAGCGGATCTGGGACAGACTTCACTCTGACAATCAGCAGCG
TGCAGGCAGAAGACGTGGCAGTCTATTATTGTCAGCAGTATTATAGCTATC
CCCTCACATTCGGCGCTGGCACCAAGCTGGAACTGAAACGTACGGTGGCT
GCACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAG
TGTCACAGAGCAGGACAGCAAGGACAGCACCTACAGCCTCAGCAGCACC
CTGACGCTGAGCAAAGCAGACTACGAGAAACACAAAGTCTACGCCTGCG
AAGTCACCCATCAGGGCCTGAGCTCGCCCGTCACAAAGAGCTTCAACAGG
GGAGAGTGTTGA

SDS-PAGE
HuCC49 G1/G3: PAP

1. HuCC49 G1/G3: PAP non-reduced (5μg)
2. Blank
3. Mark 12 Marker
4. HuCC49 G1/G3: PAP reduced (5μg)

SDS-PAGE
HuCC49 V2 G1/G3: PAP

1. HuCC49 V2 G/G3: PAP non-reduced (5μg)
2. Blank
3. Mark 12 Marker
4. HuCC49 V2 G/G3: PAP reduced (5μg)

A.
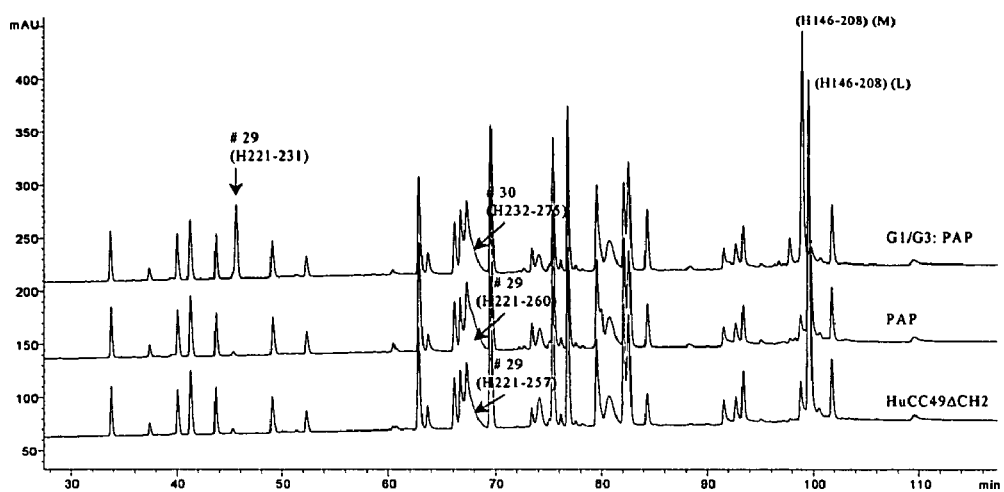
B.
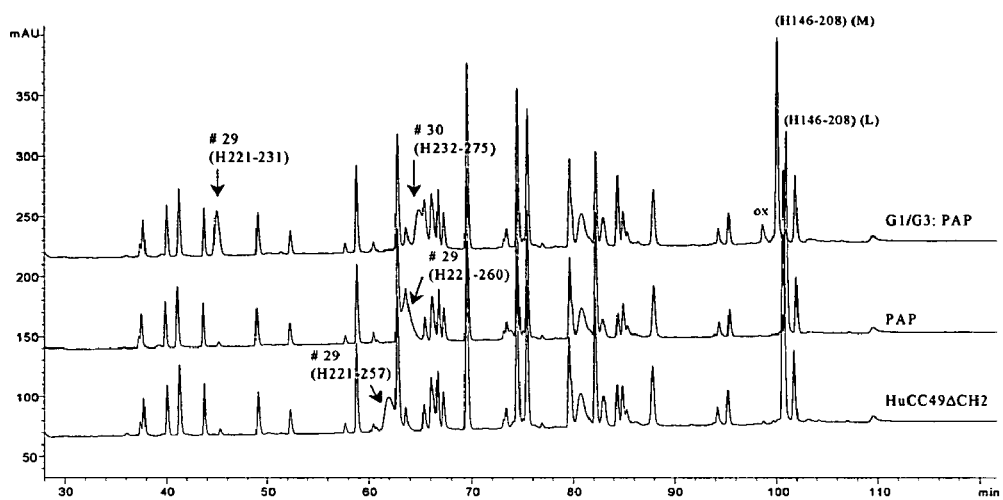
C.
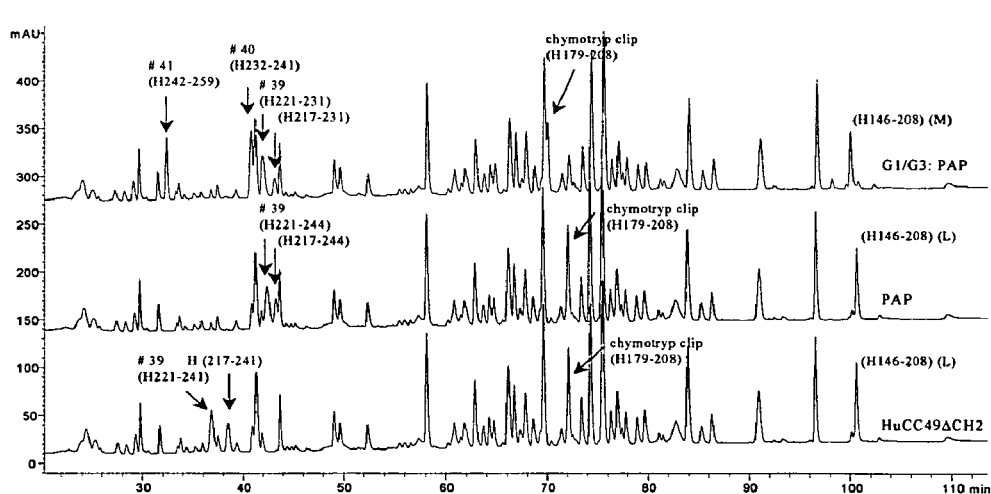
Figure 7.

Figure 8A. Amino acid sequence of heavy chain CH2 domain-deleted huCC49 Pro243Ala244Pro245 + [Gly/Ser] hinge connecting peptide
QVQLVQSGAEVVKPGASVKISCKASGYTFTDHAIHWVKQNPGQRLEWIGYFS
PGNDDFKYNERFKGKATLTADTSASTAYVELSSLRSEDTAVYFCTRSLNMAY
WGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKV
DKKVEPKSCDKTHTCPPCPAPGGGSSGGGSGGQPREPQVYTLPPSRDELTKN
QVSLTCLVKGFYPSDIAVEWESNGQPENNYKTTPPVLDSDGSFFLYSKLTVDK
SRWQQGNVFSCSVMHEALHNHYTQKSLSLSPGK Figure 8B. Amino acid sequence of light chain CH2 domain-deleted huCC49
DIVMSQSPDSLAVSLGERVTLNCKSSQSLLYSGNQKNYLAWYQQKPGQSPKL
LIYWASARESGVPDRFSGSGSGTDFTLTISSVQAEDVAVYYCQQYYSYPLTFG
AGTKLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSP
VTKSFNRGEC Single-stranded DNA sequence of heavy chain CH2 domain-deleted huCC49
G1/G3/Pro243 + [Gly/Ser] hinge connecting peptide
CAGGTCCAGCTGGTGCAGTCCGGCGCTGAGGTGGTGAAACCTGGGGCTTC
CGTGAAGATTTCCTGCAAGGCAAGCGGCTACACCTTCACTGATCACGCAA
TCCACTGGGTGAAACAGAATCCTGGACAGCGCCTGGAGTGGATTGGATAT
TTCTCTCCCGGAAACGATGATTTTAAGTACAATGAGAGGTTCAAGGGCAA
GGCCACACTGACTGCAGACACATCTGCCAGCACTGCCTACGTGGAGCTCT
CCAGCCTGAGATCCGAGGATACTGCAGTGTACTTCTGCACAAGATCCTG
AATATGGCCTACTGGGGACAGGGAACCCTGGTCACCGTCTCCAGCGCTAG
CACCAAGGGCCCATCGGTCTTCCCCCTGGCACCCTCCTCCAAGAGCACCTC
TGGGGGCACAGCGGCCCTGGGCTGCCTGGTCAAGGACTACTTCCCCGAAC
CGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTG
ACCGTGCCCTCCAGCAGCTTGGGCACCCAGACCTACATCTGCAACGTGAA
TCACAAGCCCAGCAACACCAAGGTGGACAAGAAAGTTGAGCCCAAATCTT
GTGACAAAACTCACACATGCCCACCGTGCCCAGAGCCCAAATCTTGTGAC
ACACCTCCCCCATGCCCACGGTGCCCAGGAGGTGGCTCGAGTGGAGGCGG
ATCCGGAGGGCAGCCCCGAGAACCACAGGTGTACACCCTGCCCCCATCCC
GGGATGAGCTGACCAAGAACCAGGTCAGCCTGACCTGCCTGGTCAAAGGC
TTCTATCCCAGCGACATCGCCGTGGAGTGGGAGAGCAATGGGCAGCCGGA
GAACAACTACAAGACCACGCCTCCCGTGCTGGACTCCGACGGCTCCTTCTT
CCTCTACAGCAAGCTCACCGTGGACAAGAGCAGGTGGCAGCAGGGGAAC
GTCTTCTCATGCTCCGTGATGCATGAGGCTCTGCACAACCACTACACGCAG
AAGAGCCTCTCCCTGTCTCCGGGTAAATGA

Single-stranded DNA sequence of heavy chain CH2 domain-deleted huCC49
containing G1/G3/ Pro243Ala244Pro245 + [Gly/Ser] hinge connecting peptide CAGGTCCAGCTGGTGCAGTCCGGCGCTGAGGTGGTGAAACCTGGGGCTTC
CGTGAAGATTTCCTGCAAGGCAAGCGGCTACACCTTCACTGATCACGCAA
TCCACTGGGTGAAACAGAATCCTGGACAGCGCCTGGAGTGGATTGGATAT
TTCTCTCCCGGAAACGATGATTTTAAGTACAATGAGAGGTTCAAGGGCAA
GGCCACACTGACTGCAGACACATCTGCCAGCACTGCCTACGTGGAGCTCT
CCAGCCTGAGATCCGAGGATACTGCAGTGTACTTCTGCACAAGATCCCTG
AATATGGCCTACTGGGGACAGGGAACCCTGGTCACCGTCTCCAGCGCTAG
CACCAAGGGCCCATCGGTCTTCCCCCTGGCACCCTCCTCCAAGAGCACCTC
TGGGGGCACAGCGGCCCTGGGCTGCCTGGTCAAGGACTACTTCCCCGAAC
CGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTG
ACCGTGCCCTCCAGCAGCTTGGGCACCCAGACCTACATCTGCAACGTGAA
TCACAAGCCCAGCAACACCAAGGTGGACAAGAAAGTTGAGCCCAAATCTT
GTGACAAAACTCACACATGCCCACCGTGCCCAGAGCCCAAATCTTGTGAC
ACACCTCCCCCATGCCCACGGTGCCCAGCACCTGGAGGTGGCTCGAGTGG
AGGCGGATCCGGAGGGCAGCCCCGAGAACCACAGGTGTACACCCTGCCCC
CATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCATGAGGCTCTGCACAACCACTAC
ACGCAGAAGAGCCTCTCCCTGTCTCCGGGTAAATGA Amino acid sequence of heavy chain CH2 domain-deleted huCC49 containing
G1/G3/Pro243 + [Gly/Ser] hinge connecting peptide QVQLVQSGAEVVKPGASVKISCKASGYTFTDHAIHWVKQNPGQRLEWIGYFS
PGNDDFKYNERFKGKATLTADTSASTAYVELSSLRSEDTAVYFCTRSLNMAY
WGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKV
DKKVEPKSCDKTHTCPPCPEPKSCDTPPPCPRCPGGGSSGGGSGGQPREPQVY
TLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

Figure 11

Amino acid sequence of heavy chain CH2 domain-deleted huCC49 containing
G1/G3/Pro243Ala244Pro245 + [Gly/Ser] hinge connecting peptide QVQLVQSGAEVVKPGASVKISCKASGYTFTDHAIHWVKQNPGQRLEWIGYFS
PGNDDFKYNERFKGKATLTADTSASTAYVELSSLRSEDTAVYFCTRSLNMAY
WGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKV
DKKVEPKSCDKTHTCPPCPEPKSCDTPPPCPRCPAPGGGSSGGGSGGQPREPQ
VYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

Figure 12

Figure 13A. Single-stranded DNA sequence of heavy chain CH2 domain-deleted huCC49 V2 containing G1/G3/Pro243Ala244Pro245 + [Gly/Ser] hinge connecting peptide CAGGTCCAGCTGGTGCAGTCCGGCGCTGAGGTGGTGAAACCTGGGGCTTC
CGTGAAGATTTCCTGCAAGGCAAGCGGCTACACCTTCACTGATCACGCAA
TCCACTGGGTGAAACAGAATCCTGGACAGCGCCTGGAGTGGATTGGATAT
TTCTCTCCCGGAAACGATGATTTTAAGTACAATGAGAGGTTCAAGGGCAA
GGCCACAATCACTGCAGACACATCTGCCAGCACTGCCTACGTGGAGCTCT
CCAGCCTGAGATCCGAGGATACTGCAGTGTACTTCTGCGCCAGATCCCTG
AATATGGCCTACTGGGGACAGGGAACCCTGGTCACCGTCTCCAGCGCTAG
CACCAAGGGCCCATCGGTCTTCCCCCTGGCACCCTCCTCCAAGAGCACCTC
TGGGGGCACAGCGGCCCTGGGCTGCCTGGTCAAGGACTACTTCCCCGAAC
CGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTG
ACCGTGCCCTCCAGCAGCTTGGGCACCCAGACCTACATCTGCAACGTGAA
TCACAAGCCCAGCAACACCAAGGTGGACAAGAAAGTTGAGCCCAAATCTT
GTGACAAAACTCACACATGCCCACCGTGCCCAGAGCCCAAATCTTGTGAC
ACACCTCCCCCATGCCCACGGTGCCCAGCACCTGGAGGTGGCTCGAGTGG
AGGCGGATCCGGAGGGCAGCCCCGAGAACCACAGGTGTACACCCTGCCCC
CATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCATGAGGCTCTGCACAACCACTAC
ACGCAGAAGAGCCTCTCCCTGTCTCCGGGTAAATGA Figure 13B. Single-stranded DNA sequence of light chain CH2 domain-deleted huCC49 V2

GACATCGTGATGAGCCAGTCTCCAGACTCCCTGGCCGTGTCCCTGGGCGA
GAGGGTGACTCTGAATTGCAAGTCCAGCCAGTCCCTGCTCTATAGCGGAA
ATCAGAAGAACTATCTCGCCTGGTATCAGCAGAAACCAGGGCAGCCCCCT
AAACTGCTGATTTACTGGGCATCCGCTAGGGAATCCGGCGTGCCTGATCG
CTTCAGCGGCAGCGGATCTGGGACAGACTTCACTCTGACAATCAGCAGCG
TGCAGGCAGAAGACGTGGCAGTCTATTATTGTCAGCAGTATTATAGCTATC
CCCTCACATTCGGCGCTGGCACCAAGCTGGAACTGAAACGTACGGTGGCT
GCACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAG
TGTCACAGAGCAGGACAGCAAGGACAGCACCTACAGCCTCAGCAGCACC
CTGACGCTGAGCAAAGCAGACTACGAGAAACACAAAGTCTACGCCTGCG
AAGTCACCCATCAGGGCCTGAGCTCGCCCGTCACAAAGAGCTTCAACAGG
GGAGAGTGTTGA

FIGURE 14A. Amino acid sequence of heavy chain CH2 domain-deleted huCC49 V2 containing G1/G3/Pro243Ala244Pro245 + [GlySer] hinge connecting peptide QVQLVQSGAEVVKPGASVKISCKASGYTFTDHAIHWVKQNPGQRLEWIGYFS
PGNDDFKYNERFKGKATITADTSASTAYVELSSLRSEDTAVYFCARSLNMAY
WGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKV
DKKVEPKSCDKTHTCPPCPEPKSCDTPPPCPRCPAPGGGSSGGGSGGQPREPQ
VYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK FIGURE 14B. Amino acid sequence of light chain CH2 domain-deleted huCC49 V2

DIVMSQSPDSLAVSLGERVTLNCKSSQSLLYSGNQKNYLAWYQQKPGQPPKL
LIYWASARESGVPDRFSGSGSGTDFTLTISSVQAEDVAVYYCQQYYSYPLTFG
AGTKLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSP
VTKSFNRGEC

FIGURE 14

FIGURE 17 PANEL A
UV 280 nm
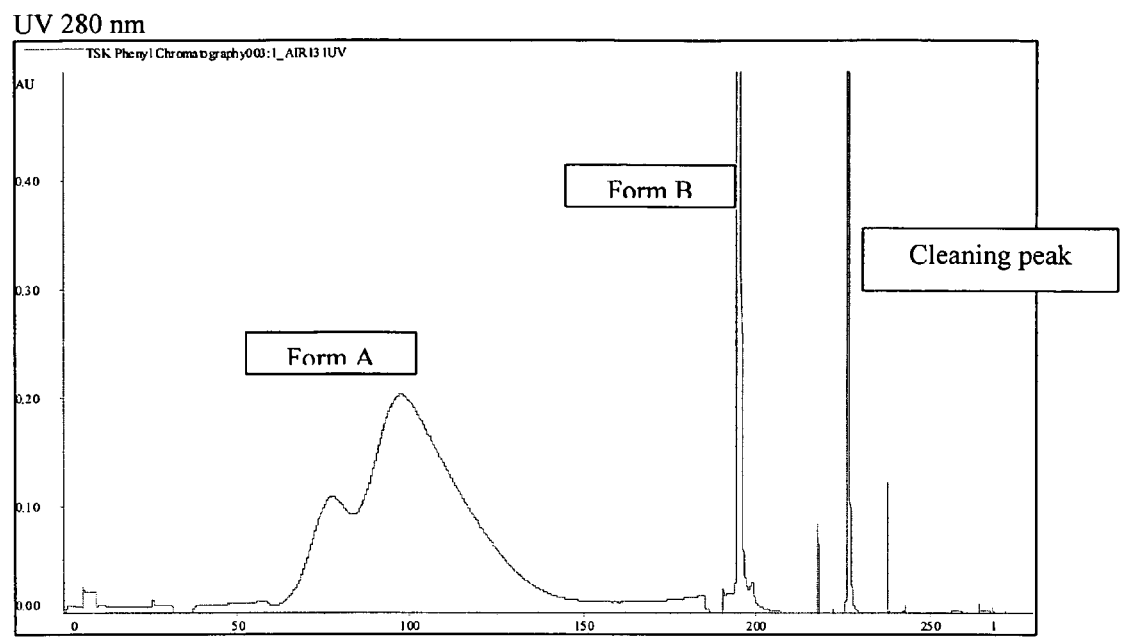
FIGURE 17 PANEL B
UV 280 nm
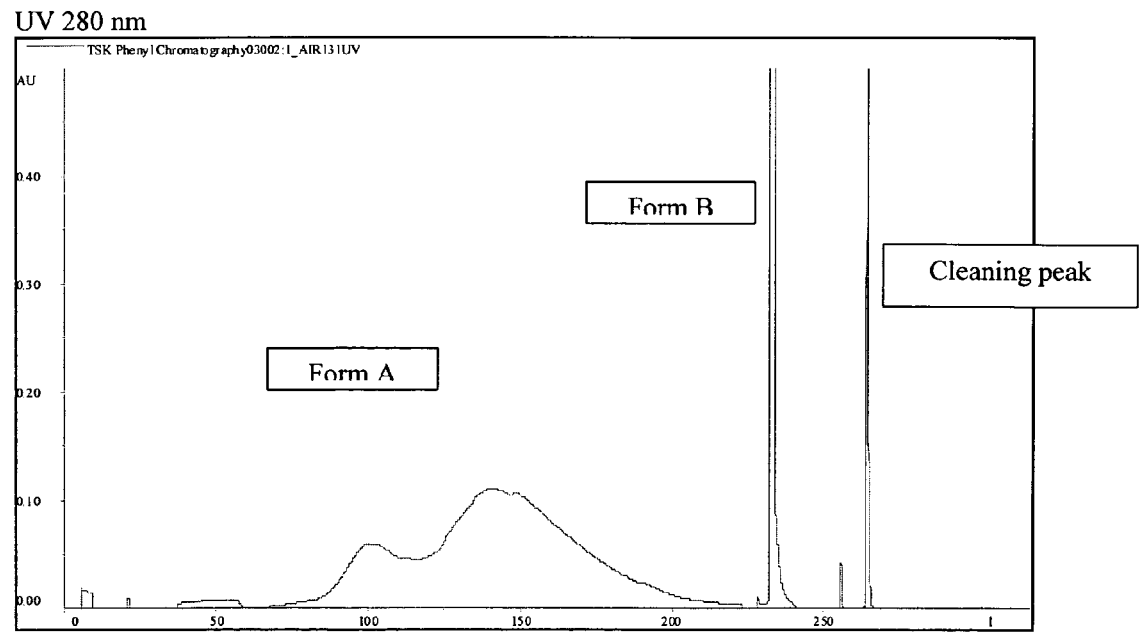

SDS-PAGE

~ 120 kd (form A)

~ 60 kd (form B)

Legend:
Lane 1: Mark 12 MW Marker, 15ul
Lane 2: CC49 Std, 10ul
Lane 3: HCCF, 13ul
Lane 4: Protein G Eluate, 5ul
Lane 5: TMAE Eluate, 10ul
Lane 6: HIC Eluate Cycle1, 5ul
Lane 7: HIC Eluate Cycle 2, 5ul
Lane 8: HIC Cycle 2 Fraction #1, 10ul Figure 19A
HuCC49 Light chain (Kabat numbering system)

```
Kabat #                 4
                        |
Murine CC49    DIVMSQSPSSLPVSVGEKVTLSC              FR1
LEN            DIVMTQSPDSLAVSLGERATINC
HuCC49         DIVMSQSPDSLAVSLGERVTLNC
HuCC49 V2      DIVMSQSPDSLAVSLGERVTLNC Murine CC49    KSSQSLLYSGNQKNYLA                    CDR1
LEN            KSSQSVLYSSNSKNYLA
HuCC49         KSSQSLLYSGNQKNYLA
HuCC49 V2      KSSQSLLYSGNQKNYLA 38   43
                        |   ||
Murine CC49    WYQQKPGQSPKLLIY                      FR2
LEN            WYQQKPGQPPKLLIY
HuCC49         WYQQKPGQSPKLLIY
HuCC49 V2      WYQQKPGQPPKLLIY Murine CC49    WASARES                              CDR2
LEN            WASTRES
HuCC49         WASARES
HuCC49 V2      WASARES 58  62 65 69 73           85
                |   |  ||||  |            |
Murine CC49    GVPDRFTGSGSGTDFTLSISSVKTEDLAVYYC  FR3
LEN            GVPDRFSGSGSGTDFTLTISSLQAEDVAVYYC
HuCC49         GVPDRFSGSGSGTDFTLTISSVQAEDVAVYYC
HuCC49 V2      GVPDRFSGSGSGTDFTLTISSVQAEDVAVYYC Murine CC49    QQYYSYPLT                            CDR3
LEN            QQYYSTPYS
HuCC49         QQYYSYPLT
HuCC49 V2      QQYYSYPLT 98
                    |
Murine CC49    FGAGTKLVLK    (SEQ ID NO:28)         FR4
LEN            FGQGTKLEIK    (SEQ ID NO:29)
HuCC49         FGAGTKLELK    (SEQ ID NO:30)
HuCC49 V2      FGAGTKLELK    (SEQ ID NO:31)
```

Figure 19B

HuCC49 Heavy Chain (Kabat numbering system)

```
Kabat #            2 4
                   | |
Murine CC49     QVQLQQSDAELVKPGASVKISCKASGYTFT              FR1
21/28'CL        QVQLVQSGAEVKKPGASVKVSCKASGYTFT
HuCC49          QVQLVQSGAEVVKPGASVKISCKASGYTFT
HuCC49 V2       QVQLVQSGAEVVKPGASVKISCKASGYTFT Murine CC49     DHAIH                                        CDR1
21/28'CL        SYAMH
HuCC49          DHAIH
HuCC49 V2       DHAIH 36 39   4345
                |  |    | |
Murine CC49     WVKQNPEQGLEWIG                               FR2
21/28'CL        WVRQAPGQRLEWMG
HuCC49          WVKQNPGQRLEWIG
HuCC49 V2       WVKQNPGQRLEWIG Murine CC49     YFSPGNDDFKYNERFKG                            CDR2
21/28'CL        WINAGNGNTKYSQKFQG
HuCC49          YFSPGNDDFKYNERFKG
HuCC49 V2       YFSPGNDDFKYNERFKG 69   74                    93
                   ||   |                     |
Murine CC49     KATLTADKSSSTAYVQLNSLTSEDSAVYFCTR             FR3
21/28'CL        RVTITRDTSASTAYMELSSLRSEDTAVYYCAR
HuCC49          KATLTADTSASTAYVELSSLRSEDTAVYFCTR
HuCC49 V2       KATITADTSASTAYVELSSLRSEDTAVYFCAR Murine CC49     SLNMA     Y                                  CDR3
21/28'CL        GGYYGSGSNY
HuCC49          SLNMA     Y
HuCC49 V2       SLNMA     Y Murine CC49     WGQGTSVTVSS    (SEQ ID NO:32)                FR4
21/28'CL        WGQGTLVTVSS    (SEQ ID NO:33)
HuCC49          WGQGTLVTVSS    (SEQ ID NO:34)
HuCC49 V2       WGQGTLVTVSS    (SEQ ID NO:35)
```

CH2 Domain-Deleted CC49:
Gly-Ser vs γ1γ3 Hinge Stability Toward Reducing Agents Figure 25A. Nucleic acid sequence of the heavy chain CH2 domain-deleted anti-CD20 IgG1 C2B8 containing the G1/G3/Pro243Ala244Pro245 + [GlySer] hinge connecting peptide.

```
CAGGTACAACTGCAGCAGCCTGGGGCTGAGCTGGTGAAGCCTGGGGCCTCAGTGAAGATGTCCTGCAAGGC
TTCTGGCTACACATTTACCAGTTACAATATGCACTGGGTAAAACAGACACCTGGTCGGGGCCTGGAATGGAT
TGGAGCTATTTATCCCGGAAATGGTGATACTTCCTACAATCAGAAGTTCAAAGGCAAGGCCACATTGACTGC
AGACAAATCCTCCAGCACAGCCTACATGCAGCTCAGCAGCCTGACATCTGAGGACTCTGCGGTCTATTACTG
TGCAAGATCGACTTACTACGGCGGTGACTGGTACTTCAATGTCTGGGGCGCAGGGACCACGGTCACCGTCT
CTGCAGCTAGCACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGAC
CGTGCCCTCCAGCAGCTTGGGCACCCAGACCTACATCTGCAACGTGAATCACAAGCCCAGCAACACCAAGG
TGGACAAGAAAGTTGAGCCCAAATCTTGTGACAAAACTCACACATGCCCACCGTGCCCAGAGCCCAAATCT
TGTGACACACCTCCCCCATGCCCACGGTGCCCAGCACCTGGAGGTGGCTCGAGTGGAGGCGGTTCCGGAGG
GCAGCCCCGAGAACCACAGGTGTACACCCTGCCCCCATCCCGGGATGAGCTGACCAAGAACCAGGTCAGCC
TGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTG
GACAAGAGCAGGTGGCAGCAGGGGAACGTCTTCTCATGCTCCGTGATGCATGAGGCTCTGCACAACCACTA
CACGCAGAAGAGCCTCTCCCTGTCTCCGGGTAAATGA
```

Figure 25B. Amino acid sequence of the heavy chain CH2 domain-deleted anti-CD20 IgG1 C2B8 containing the G1/G3/Pro243Ala244Pro245 + [GlySer] hinge connecting peptide.

```
QVQLQQPGAELVKPGASVKMSCKASGYTFTSYNMHWVKQTPGRGLEWIGAIYPGNGDTSYNQKFKGKATLTA
DKSSSTAYMQLSSLTSEDSAVYYCARSTYYGGDWYFNVWGAGTTVTVSAASTKGPSVFPLAPSSKSTSGGTAAL
GCLVKDYFPEPVTVSWNSGALTSGVHTFPAVLQSSGLYSLSSVVTVPSSSLGTQTYICNVNHKPSNTKVDKKVEP
KSCDKTHTCPPCPEPKSCDTPPPCPRCPAPGGGSSGGGSGGQPREPQVYTLPPSRDELTKNQVSLTCLVKGFYPSD
IAVEWESNGQPENNYKTTPPVLDSDGSFFLYSKLTVDKSRWQQGNVFSCSVMHEALHNHYTQKSLSLSPGK*
```

Figure 26A. Nucleotide sequence of the light chain CH2 domain-deleted anti-CD20 IgG1 C2B8.

CAAATTGTTCTCTCCCAGTCTCCAGCAATCCTGTCTGCATCTCCAGGGGAGAAGGTCACAATGA
CTTGCAGGGCCAGCTCAAGTGTAAGTTACATCCACTGGTTCCAGCAGAAGCCAGGATCGTCCCC
CAAACCCTGGATTTATGCCACATCCAACCTGGCTTCTGGAGTCCCTGTTCGCTTCAGTGGCAGT
GGGTCTGGGACTTCTTACTCTCTCACAATCAGCAGAGTGGAGGCTGAAGATGCTGCCACTTATT
ACTGCCAGCAGTGGACTAGTAACCCACCCACGTTCGGAGGGGGGACCAAGCTGGAAATCAAAC
GTACGGTGGCTGCACCATCTGTCTTCATCTTCCCGCCATCTGATGAGCAGTTGAAATCTGGAAC
TGCCTCTGTTGTGTGCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTAC
GCCTGCGAAGTCACCCATCAGGGCCTGAGCTCGCCCGTCACAAAGAGCTTCAACAGGGGAGAG
TGTTGA

Figure 26B. Amino acid sequence of the light chain CH2 domain-deleted anti-CD20 IgG1 C2B8.

QIVLSQSPAILSASPGEKVTMTCRASSSVSYIHWFQQKPGSSPKPWIYATSNLASGVPVRFSGSGSGT
SYSLTISRVEAEDAATYYCQQWTSNPPTFGGGTKLEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLS
SPVTKSFNRGEC*

| Lane | Sample |
|------|--------|
| 1 | MW markers |
| 2 | ddCC49 |
| 3 | dd anti-CD20 G1/G3/PAP |

Figure 28A. Single-stranded DNA sequence of heavy chain CH2 domain-deleted anti-CD23 containing G1/G3/Pro243Ala244Pro245 + [Gly/Ser] hinge connecting peptide GAGGTGCAGCTGGTGGAGTCTGGGGGCGGCTTGGCAAAGCCTGGGGGGTCCCTGAGACTCTCC
TGCGCAGCCTCCGGGTTCAGGTTCACCTTCAATAACTACTACATGGACTGGGTCCGCCAGGCTC
CAGGGCAGGGGCTGGAGTGGGTCTCACGTATTAGTAGTAGTGGTGATCCCACATGGTACGCAG
ACTCCGTGAAGGGCAGATTCACCATCTCCAGAGAGAACGCCAAGAACACACTGTTTCTTCAAA
TGAACAGCCTGAGAGCTGAGGACACGGCTGTCTATTACTGTGCGAGCTTGACTACAGGGTCTG
ACTCCTGGGGCCAGGGAGTCCTGGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTGGTGACCGTGCCCT
CCAGCAGCTTGGGCACCCAGACCTACATCTGCAACGTGAATCACAAGCCCAGCAACACCAAGG
TGGACAAGAAAGTTGAGCCCAAATCTTGTGACAAAACTCACACATGCCCACCGTGCCCAGAGC
CCAAATCTTGTGACACACCTCCCCCATGCCCACGGTGCCCAGCACCTGGAGGTGGCTCGAGTGG
AGGCGGTTCCGGAGGGCAGCCCCGAGAACCACAGGTGTACACCCTGCCCCCATCCCGGGATGA
GCTGACCAAGAACCAGGTCAGCCTGACCTGCCTGGTCAAAGGCTTCTATCCCAGCGACATCGCC
GTGGAGTGGGAGAGCAATGGGCAGCCGGAGAACAACTACAAGACCACGCCTCCCGTGCTGGA
CTCCGACGGCTCCTTCTTCCTCTACAGCAAGCTCACCGTGGACAAGAGCAGGTGGCAGCAGGG
GAACGTCTTCTCATGCTCCGTGATGCATGAGGCTCTGCACAACCACTACACGCAGAAGAGCCTC
TCCCTGTCTCCGGGTAAA Figure 28B. Single-stranded DNA sequence of light chain CH2 domain-deleted anti-CD23

GACATCCAGATGACCCAGTCTCCATCTTCCCTGTCTGCATCTGTAGGGGACAGAGTCACCATCA
CTTGCAGGGCAAGTCAGGACATTAGGTATTATTTAAATTGGTATCAGCAGAAACCAGGAAAAG
CTCCTAAGCTCCTGATCTATGTTGCATCCAGTTTGCAAAGTGGGGTCCCATCAAGGTTCAGCGG
CAGTGGATCTGGGACAGAGTTCACTCTCACCGTCAGCAGCCTGCAGCCTGAAGATTTTGCGACT
TATTACTGTCTACAGGTTTATAGTACCCCTCGGACGTTCGGCCAAGGGACCAAGGTGGAAATCA
AACGTACGGTGGCTGCACCATCTGTCTTCATCTTCCCGCCATCTGATGAGCAGTTGAAATCTGG
AACTGCCTCTGTTGTGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCAGGACAGCAAGGAC
AGCACCTACAGCCTCAGCAGCACCCTGACGCTGAGCAAAGCAGACTACGAGAAACACAAAGTC
TACGCCTGCGAAGTCACCCATCAGGGCCTGAGCTCGCCCGTCACAAAGAGCTTCAACAGGGGA
GAGTGT

Figure 29A. Amino acid sequence of heavy chain CH2 domain-deleted anti-CD23 containing G1/G3/Pro243Ala244Pro245 + [Gly/Ser] hinge connecting peptide EVQLVESGGGLAKPGGSLRLSCAASGFRFTFNNYYMDWVRQAPGQGLEWVSRISSSGDPTWYADS
VKGRFTISRENAKNTLFLQMNSLRAEDTAVYYCASLTTGSDSWGQGVLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPEPKSCDTPPPCPRCPAPGGGSSGGGSGGQPREPQ
VYTLPPSRDELTKNQVSLTCLVKGFYPSDIAVEWESNGQPENNYKTTPPVLDSDGSFFLYSKLTVDK
SRWQQGNVFSCSVMHEALHNHYTQKSLSLSPGK Figure 29B. Amino acid sequence of light chain CH2 domain-deleted anti-CD23

DIQMTQSPSSLSASVGDRVTITCRASQDIRYYLNWYQQKPGKAPKLLIYVASSLQSGVPSRFSGSGS
GTEFTLTVSSLQPEDFATYYCLQVYSTPRTFGQGTKVEIKRTVAAPSVFIFPPSDEQLKSGTASVVCL
LNNFYPREAKVQWKVDNALQSGNSQESVTEQDSKDSTYSLSSTLTLSKADYEKHKVYACEVTHQG
LSSPVTKSFNRGEC

5E8ΔCH2 G1/G3:PAP

Lane 1. Mark 12 standards
Lane 2. 5E8ΔCH2 G1/G3:PAP (non-reduced)
Lane 3. Blank
Lane 4. 5E8ΔCH2 G1/G3:PAP (reduced)

Figure 32A. Nucleic acid sequence of heavy chain CH2 domain-deleted chB3F6 containing G1/G3:Pro243Ala244Pro245 + [Gly/Ser] hinge connecting peptide CAGGTCCAACTGCAGCAGGTTGGGGCTGAACTGGTGAAGCCTGGGGCTTCAGTGAAGCTGTCC
TGCAAGGCTTCTGGCTACACCTTCACCAGCTACTGGATACACTGGGTGAAGCAGAGGCCTGGA
CAGGGCCTTGAGTGGATTGGAGAGAATGATCCTAGCAACGGTCGTACTAACTACAATGAGAAG
TTCAAGAACAAGGCCACACTGACTGTAGACAAATCCTCCAGCACAGCCTACATGCATCTCAGC
AGCCTGACATCTGAGGACTCTGCGGTCTATTACTGTTCAAGGGGCCCTAATTACTTCTATTCTAT
GGACTACTGGGGTCAAGGAACCTCAGTCACCGTCTCCTCAGCTAGCACCAAGGGCCCATCGGT
CTTCCCCCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGACCGTGC
CCTCCAGCAGCTTGGGCACCCAGACCTACATCTGCAACGTGAATCACAAGCCCAGCAACACCA
AGGTGGACAAGAAAGTTGAGCCCAAATCTTGTGACAAAACTCACACATGCCCACCGTGCCCAG
AGCCCAAATCTTGTGACACACCTCCCCCATGCCCACGGTGCCCAGCACCTGGAGGTGGCTCGAG
TGGAGGCGGTTCCGGAGGGCAGCCCCGAGAACCACAGGTGTACACCCTGCCCCCATCCCGGGA
TGAGCTGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAGAGC
CTCTCCCTGTCTCCGGGT Figure 32B. Nucleic acid sequence of light chain CH2 domain-deleted chB3F6

GATTTTTTGATGACCCAAACTCCACTCTCCCTGCCTGTCAGTCTTGGAGATCAAGCCTCCATCTC
TTGCAGATCAAGTCAGAGCATTGTACATAGTAATGGAAACACCTATTTAGAATGGTACCTGCAG
AAACCAGGCCAGTCTCCAAAGCTCCTCATCTACAAAGTTTCCAACCGATTTTCTGGGGTCCCAG
ACAGGTTCAGTGGCAGTGGATCAGGGACAGATTTCACACTCAAGATCAGCAGAGTGGAGGCTG
AGGATCTGGGAGTTTATTACTGCTTTCAAGGTTCACATGTTCCTCTCACGTTCGGTGCTGGGACC
AAGCTGGAGCTGAAGCGTACGGTGGCTGCACCATCTGTCTTCATCTTCCCGCCATCTGATGAGC
AGTTGAAATCTGGAACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGAGTGTCACAGAGCA
GGACAGCAAGGACAGCACCTACAGCCTCAGCAGCACCCTGACGCTGAGCAAAGCAGACTACG
AGAAACACAAAGTCTACGCCTGCGAAGTCACCCATCAGGGCCTGAGCTCGCCCGTCACAAAGA
GCTTCAACAGGGGAGAGTGT

Figure 33A. Amino acid sequence of heavy chain CH2 domain-deleted chB3F6 containing G1/G3:Pro243Ala244Pro245 + [Gly/Ser] hinge connecting peptide QVQLQQVGAELVKPGASVKLSCKASGYTFTSYWIHWVKQRPGQGLEWIGENDPSNGRTNYNEKF
KNKATLTVDKSSSTAYMHLSSLTSEDSAVYYCSRGPNYFYSMDYWGQGTSVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPEPKSCDTPPPCPRCPAPGGGSSGGGSGGQPRE
PQVYTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPG Figure 33B. Amino acid sequence of light chain CH2 domain-deleted chB3F6

DFLMTQTPLSLPVSLGDQASISCRSSQSIVHSNGNTYLEWYLQKPGQSPKLLIYKVSNRFSGVPDRFS
GSGSGTDFTLKISRVEAEDLGVYYCFQGSHVPLTFGAGTKLELKRTVAAPSVFIFPPSDEQLKSGTAS
VVCLLNNFYPREAKVQWKVDNALQSGNSQESVTEQDSKDSTYSLSSTLTLSKADYEKHKVYACEV
THQGLSSPVTKSFNRGEC

ChB3F6ΔCH2 G1/G3:PAP

Lane 1. Mark 12 standards
Lane 2. ChB3F6ΔCH2 G1/G3:PAP reduced
Lane 3. Blank
Lane 4. ChB3F6ΔCH2 G1/G3:PAP non-reduced

```
                         SEQUENCE LISTING

<160> NUMBER OF SEQ ID NOS: 53

<210> SEQ ID NO 1
<211> LENGTH: 10
<212> TYPE: PRT
<213> ORGANISM: Artificial Sequence
<220> FEATURE:
<223> OTHER INFORMATION: Synthetic construct

<400> SEQUENCE: 1

Gly Gly Gly Ser Ser Gly Gly Gly Ser Gly
 1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Glu Pro Lys Ser Cys Asp Lys Thr His Thr
 1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic construct

<400> SEQUENCE: 3

Cys Pro Pro Cys Pro
 1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic construct

<400> SEQUENCE: 4

Ala Pro Glu Leu Leu Gly Gly Pro
```

<210> SEQ ID NO 5
<211> LENGTH: 12
<212> TYPE: PRT
<213> ORGANISM: Artificial Sequence
<220> FEATURE:
<223> OTHER INFORMATION: Synthetic construct

<400> SEQUENCE: 5

Glu Leu Lys Thr Pro Leu Gly Asp Thr Thr His Thr
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Synthetic construct

<400> SEQUENCE: 6

Cys Pro Arg Cys Pro Glu Pro Lys Ser Cys Asp Thr Pro Pro Pro Cys
1               5                   10                  15

Pro Arg Cys Pro
            20

<210> SEQ ID NO 7
<211> LENGTH: 24
<212> TYPE: PRT
<213> ORGANISM: Artificial Sequence
<220> FEATURE:
<223> OTHER INFORMATION: Synthetic construct

<400> SEQUENCE: 7

Glu Pro Lys Ser Cys Asp Lys Thr His Thr Cys Pro Pro Cys Gly Gly
1               5                   10                  15

Gly Ser Ser Gly Gly Gly Ser Gly
            20

<210> SEQ ID NO 8
<211> LENGTH: 40
<212> TYPE: PRT
<213> ORGANISM: Artificial Sequence
<220> FEATURE:
<223> OTHER INFORMATION: Synthetic construct

<400> SEQUENCE: 8

Glu Pro Lys Ser Cys Asp Lys Thr His Thr Cys Pro Pro Cys Pro Glu
1               5                   10                  15

Pro Lys Ser Cys Asp Thr Pro Pro Pro Cys Pro Arg Cys Pro Gly Gly
            20                  25                  30

Gly Ser Ser Gly Gly Gly Ser Gly
        35                  40

<210> SEQ ID NO 9
<211> LENGTH: 42
<212> TYPE: PRT
<213> ORGANISM: Artificial Sequence
<220> FEATURE:
<223> OTHER INFORMATION: Synthetic construct

<400> SEQUENCE: 9

Glu Pro Lys Ser Cys Asp Lys Thr His Thr Cys Pro Pro Cys Pro Glu
1               5                   10                  15

-continued

```
Pro Lys Ser Cys Asp Thr Pro Pro Cys Pro Arg Cys Pro Ala Pro
            20                  25                  30
Gly Gly Gly Ser Ser Gly Gly Ser Gly
            35                  40

<210> SEQ ID NO 10
<211> LENGTH: 25
<212> TYPE: PRT
<213> ORGANISM: Artificial Sequence
<220> FEATURE:
<223> OTHER INFORMATION: Synthetic construct

<400> SEQUENCE: 10

Glu Pro Lys Ser Cys Asp Lys Thr His Thr Ser Pro Pro Cys Pro Gly
  1               5                  10                  15
Gly Gly Ser Ser Gly Gly Gly Ser Gly
            20                  25

<210> SEQ ID NO 11
<211> LENGTH: 27
<212> TYPE: PRT
<213> ORGANISM: Artificial Sequence
<220> FEATURE:
<223> OTHER INFORMATION: Synthetic construct

<400> SEQUENCE: 11

Glu Pro Lys Ser Cys Asp Lys Thr His Thr Ser Pro Pro Cys Pro Ala
  1               5                  10                  15
Pro Gly Gly Gly Ser Ser Gly Gly Gly Ser Gly
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic construct

<400> SEQUENCE: 12

Glu Pro Lys Ser Cys Asp Lys Thr His Thr Cys Pro Pro Ser Pro Gly
  1               5                  10                  15
Gly Gly Ser Ser Gly Gly Gly Ser Gly
            20                  25

<210> SEQ ID NO 13
<211> LENGTH: 27
<212> TYPE: PRT
<213> ORGANISM: Artificial Sequence
<220> FEATURE:
<223> OTHER INFORMATION: Synthetic construct

<400> SEQUENCE: 13

Glu Pro Lys Ser Cys Asp Lys Thr His Thr Cys Pro Pro Ser Pro Ala
  1               5                  10                  15
Pro Gly Gly Gly Ser Ser Gly Gly Gly Ser Gly
            20                  25

<210> SEQ ID NO 14
<211> LENGTH: 27
<212> TYPE: PRT
<213> ORGANISM: Artificial Sequence
<220> FEATURE:
<223> OTHER INFORMATION: Synthetic construct

<400> SEQUENCE: 14
```

Glu Pro Lys Ser Cys Asp Lys Thr His Thr Cys Pro Pro Cys Pro Ala
1               5                   10                  15

Pro Gly Gly Gly Ser Ser Gly Gly Gly Ser Gly
            20                  25

<210> SEQ ID NO 15
<211> LENGTH: 25
<212> TYPE: PRT
<213> ORGANISM: Artificial Sequence
<220> FEATURE:
<223> OTHER INFORMATION: Synthetic construct

<400> SEQUENCE: 15

Glu Pro Lys Ser Cys Asp Lys Thr His Thr Cys Pro Pro Cys Pro Gly
1               5                   10                  15

Gly Gly Ser Ser Gly Gly Gly Ser Gly
            20                  25

<210> SEQ ID NO 16
<211> LENGTH: 1044
<212> TYPE: DNA
<213> ORGANISM: Artificial Sequence
<220> FEATURE:
<223> OTHER INFORMATION: Synthetic construct

<400> SEQUENCE: 16
caggtccagc tggtgcagtc cggcgctgag gtggtgaaac ctggggcttc cgtgaagatt      60
tcctgcaagg caagcggcta caccttcact gatcacgcaa tccactgggt gaaacagaat     120
cctggacagc gcctggagtg gattggatat ttctctcccg aaacgatga ttttaagtac      180 aatgagaggt tcaagggcaa ggccacactg actgcagaca catctgccag cactgcctac     240
gtggagctct ccagcctgag atccgaggat actgcagtgt acttctgcac aagatccctg     300
aatatggcct actggggaca gggaaccctg gtcaccgtct ccagcgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgt gaccgtgcc ctccagcagc ttgggcaccc agacctacat ctgcaacgtg      600
aatcacaagc ccagcaacac caaggtggac aagaaagttg agcccaaatc ttgtgacaaa     660
actcacacat gcccaccgtg cccagcacct ggaggtggct cgagtggagg cggatccgga     720
gggcagcccc gagaaccaca ggtgtacacc ctgcccccat cccgggatga gctgaccaag     780
aaccaggtca gcctgacctg cctggtcaaa ggcttctatc ccagcgacat cgccgtggag     840
tgggagagca atgggcagcc ggagaacaac tacaagacca cgcctcccgt gctggactcc     900
gacggctcct tcttcctcta cagcaagctc accgtggaca gagcaggtg gcagcagggg     960 aacgtcttct catgctccgt gatgcatgag gctctgcaca accactacac gcagaagagc    1020
ctctccctgt ctccgggtaa atga                                           1044

<210> SEQ ID NO 17
<211> LENGTH: 663
<212> TYPE: DNA
<213> ORGANISM: Artificial Sequence
<220> FEATURE:
<223> OTHER INFORMATION: Synthetic construct

<400> SEQUENCE: 17

```
gacatcgtga tgagccagtc tccagactcc ctggccgtgt ccctgggcga gagggtgact    60
ctgaattgca agtccagcca gtccctgctc tatagcggaa atcagaagaa ctatctcgcc   120
tggtatcagc agaaaccagg gcagagccct aaactgctga tttactgggc atccgctagg   180
gaatccggcg tgcctgatcg cttcagcggc agcggatctg ggacagactt cactctgaca   240
atcagcagcg tgcaggcaga agacgtggca gtctattatt gtcagcagta ttatagctat   300 ccectcacat tcggcgctgg caccaagctg gaactgaaac gtacggtggc tgcaccatct   360
gtcttcatct cccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc   600 gaagtcaccc atcagggcct gagctcgccc gtcacaaaga gcttcaacag gggagagtgt   660
tga                                                                 663
```

<210> SEQ ID NO 18
<211> LENGTH: 347
<212> TYPE: PRT
<213> ORGANISM: Artificial Sequence
<220> FEATURE:
<223> OTHER INFORMATION: Synthetic construct

<400> SEQUENCE: 18

```
Gln Val Gln Leu Val Gln Ser Gly Ala Glu Val Val Lys Pro Gly Ala
 1               5                  10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Gly Gly Gly Ser Gly Gly Gly Ser Gly
225                 230                 235                 240
```

```
Gly Gln Pro Arg Glu Pro Gln Val Tyr Thr Leu Pro Pro Ser Arg Asp
                245                 250                 255

Glu Leu Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 19
<211> LENGTH: 220
<212> TYPE: PRT
<213> ORGANISM: Artificial Sequence
<220> FEATURE:
<223> OTHER INFORMATION: Synthetic construct

<400> SEQUENCE: 19

Asp Ile Val Met Ser Gln Ser Pro Asp Ser Leu Ala Val Ser Leu Gly
1               5                   10                  15

Glu Arg Val Thr Leu Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 20
<211> LENGTH: 1083
<212> TYPE: DNA
<213> ORGANISM: Artificial Sequence
<220> FEATURE:
```

<400> SEQUENCE: 20

```
caggtccagc tggtgcagtc cggcgctgag gtggtgaaac ctggggcttc cgtgaagatt      60
tcctgcaagg caagcggcta caccttcact gatcacgcaa tccactgggt gaaacagaat     120
cctggacagc gcctggagtg gattggatat ttctctcccg gaaacgatga ttttaagtac     180
aatgagaggt tcaagggcaa ggccacactg actgcagaca catctgccag cactgcctac     240
gtggagctct ccagcctgag atccgaggat actgcagtgt acttctgcac aagatccctg     300
aatatggcct actggggaca gggaaccctg gtcaccgtct ccagcgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagagccc aaatcttgtg acacacctcc cccatgccca     720
cggtgcccag gaggtggctc gagtggaggc ggatccggag ggcagccccg agaaccacag     780
gtgtacaccc tgcccccatc ccgggatgag ctgaccaaga accaggtcag cctgacctgc     840
ctggtcaaag cttctatcc cagcgacatc gccgtggagt gggagagcaa tgggcagccg     900
gagaacaact acaagaccac gcctcccgtg ctggactccg acggctcctt cttcctctac     960
agcaagctca ccgtggacaa gagcaggtgg cagcagggga acgtcttctc atgctccgtg    1020
atgcatgagg ctctgcacaa ccactacacg cagaagagcc tctccctgtc tccgggtaaa    1080
tga                                                                  1083
```

<210> SEQ ID NO 21
<211> LENGTH: 1089
<212> TYPE: DNA
<213> ORGANISM: Artificial Sequence
<220> FEATURE:
<223> OTHER INFORMATION: Synthetic construct

<400> SEQUENCE: 21

```
caggtccagc tggtgcagtc cggcgctgag gtggtgaaac ctggggcttc cgtgaagatt      60
tcctgcaagg caagcggcta caccttcact gatcacgcaa tccactgggt gaaacagaat     120
cctggacagc gcctggagtg gattggatat ttctctcccg gaaacgatga ttttaagtac     180
aatgagaggt tcaagggcaa ggccacactg actgcagaca catctgccag cactgcctac     240
gtggagctct ccagcctgag atccgaggat actgcagtgt acttctgcac aagatccctg     300
aatatggcct actggggaca gggaaccctg gtcaccgtct ccagcgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagagccc aaatcttgtg acacacctcc cccatgccca     720
cggtgcccag cacctggagg tggctcgagt ggaggcggat ccgagggca gccccgagaa     780
ccacaggtgt acaccctgcc cccatcccgg gatgagctga ccaagaacca ggtcagcctg     840
```

-continued

```
acctgcctgg tcaaaggctt ctatcccagc gacatcgccg tggagtggga gagcaatggg      900
cagccggaga caactacaa gaccacgcct cccgtgctgg actccgacgg ctccttcttc       960
ctctacagca agctcaccgt ggacaagagc aggtggcagc aggggaacgt cttctcatgc     1020
tccgtgatgc atgaggctct gcacaaccac tacacgcaga gagcctctc cctgtctccg     1080 ggtaaatga                                                             1089
```

<210> SEQ ID NO 22
<211> LENGTH: 360
<212> TYPE: PRT
<213> ORGANISM: Artificial Sequence
<220> FEATURE:
<223> OTHER INFORMATION: Synthetic construct

<400> SEQUENCE: 22

```
Gln Val Gln Leu Val Gln Ser Gly Ala Glu Val Val Lys Pro Gly Ala
  1               5                  10                  15

Ser Val Lys Ile Ser Cys Lys Ala Ser Gly Tyr Thr Phe Thr Asp His
             20                  25                  30

Ala Ile His Trp Val Lys Gln Asn Pro Gly Gln Arg Leu Glu Trp Ile
         35                  40                  45

Gly Tyr Phe Ser Pro Gly Asn Asp Asp Phe Lys Tyr Asn Glu Arg Phe
     50                  55                  60

Lys Gly Lys Ala Thr Leu Thr Ala Asp Thr Ser Ala Ser Thr Ala Tyr
 65                  70                  75                  80

Val Glu Leu Ser Ser Leu Arg Ser Glu Asp Thr Ala Val Tyr Phe Cys
                 85                  90                  95

Thr Arg Ser Leu Asn Met Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Glu Pro Lys Ser Cys Asp Thr Pro Pro Cys Pro
225                 230                 235                 240

Arg Cys Pro Gly Gly Ser Ser Gly Gly Ser Gly Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
```

```
                 305                 310                 315                 320
Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
                340                 345                 350

Ser Leu Ser Leu Ser Pro Gly Lys
                355                 360

<210> SEQ ID NO 23
<211> LENGTH: 362
<212> TYPE: PRT
<213> ORGANISM: Artificial Sequence
<220> FEATURE:
<223> OTHER INFORMATION: Synthetic construct

<400> SEQUENCE: 23

Gln Val Gln Leu Val Gln Ser Gly Ala Glu Val Val Lys Pro Gly Ala
  1               5                  10                  15

Ser Val Lys Ile Ser Cys Lys Ala Ser Gly Tyr Thr Phe Thr Asp His
                 20                  25                  30

Ala Ile His Trp Val Lys Gln Asn Pro Gly Gln Arg Leu Glu Trp Ile
             35                  40                  45

Gly Tyr Phe Ser Pro Gly Asn Asp Asp Phe Lys Tyr Asn Glu Arg Phe
 50                  55                  60

Lys Gly Lys Ala Thr Leu Thr Ala Asp Thr Ser Ala Ser Thr Ala Tyr
 65                  70                  75                  80

Val Glu Leu Ser Ser Leu Arg Ser Glu Asp Thr Ala Val Tyr Phe Cys
                 85                  90                  95

Thr Arg Ser Leu Asn Met Ala Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Glu Pro Lys Ser Cys Asp Thr Pro Pro Cys Pro
225                 230                 235                 240

Arg Cys Pro Ala Pro Gly Gly Ser Gly Gly Gly Ser Gly Gly
                245                 250                 255

Gln Pro Arg Glu Pro Gln Val Tyr Thr Leu Pro Pro Ser Arg Asp Glu
            260                 265                 270

Leu Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
    290                 295                 300

Asn Tyr Lys Thr Thr Pro Pro Val Leu Asp Ser Asp Gly Ser Phe Phe
```

```
                305                 310                 315                 320
Leu Tyr Ser Lys Leu Thr Val Asp Lys Ser Arg Trp Gln Gln Gly Asn
                    325                 330                 335
Val Phe Ser Cys Ser Val Met His Glu Ala Leu His Asn His Tyr Thr
                    340                 345                 350
Gln Lys Ser Leu Ser Leu Ser Pro Gly Lys
                    355                 360
```

```
<210> SEQ ID NO 24
<211> LENGTH: 1089
<212> TYPE: DNA
<213> ORGANISM: Artificial Sequence
<220> FEATURE:
<223> OTHER INFORMATION: Synthetic construct

<400> SEQUENCE: 24
caggtccagc tggtgcagtc cggcgctgag gtggtgaaac ctggggcttc cgtgaagatt      60
tcctgcaagg caagcggcta caccttcact gatcacgcaa tccactgggt gaaacagaat    120
cctggacagc gcctggagtg gattggatat ttctctcccg gaaacgatga tttttaagtac   180 aatgagaggt tcaagggcaa ggccacaatc actgcagaca catctgccag cactgcctac    240
gtggagctct ccagcctgag atccgaggat actgcagtgt acttctgcgc cagatccctg    300
aatatggcct actggggaca gggaaccctg gtcaccgtct ccagcgctag caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagagccc aaatcttgtg acacacctcc cccatgccca    720
cggtgcccag cacctggagg tggctcgagt ggaggcggat ccggagggca gccccgagaa    780
ccacaggtgt acaccctgcc cccatcccgg gatgagctga ccaagaacca ggtcagcctg    840
acctgcctgg tcaaaggctt ctatcccagc gacatcgccg tggagtggga gagcaatggg    900
cagccggaga caactacaa gaccacgcct cccgtgctgg actccgacgg ctccttcttc     960
ctctacagca agctcaccgt ggacaagagc aggtggcagc aggggaacgt cttctcatgc   1020
tccgtgatgc atgaggctct gcacaaccac tacacgcaga gagcctctcc ctgtctccg    1080 ggtaaatga                                                            1089
```

```
<210> SEQ ID NO 25
<211> LENGTH: 663
<212> TYPE: DNA
<213> ORGANISM: Artificial Sequence
<220> FEATURE:
<223> OTHER INFORMATION: Synthetic construct

<400> SEQUENCE: 25
gacatcgtga tgagccagtc tccagactcc ctggccgtgt ccctgggcga gagggtgact     60
ctgaattgca gtccagcca gtccctgctc tatagcggaa atcagaagaa ctatctcgcc    120
tggtatcagc agaaaccagg gcagcccccct aaactgctga tttactgggc atccgctagg   180
gaatccggcg tgcctgatcg cttcagcggc agcggatctg ggacagactt cactctgaca    240
atcagcagcg tgcaggcaga agacgtggca gtctattatt gtcagcagta ttatagctat    300
```

```
cccctcacat tcggcgctgg caccaagctg gaactgaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
tga                                                                  663
```

```
<210> SEQ ID NO 26
<211> LENGTH: 362
<212> TYPE: PRT
<213> ORGANISM: Artificial Sequence
<220> FEATURE:
<223> OTHER INFORMATION: Synthetic construct

<400> SEQUENCE: 26
```

```
Gln Val Gln Leu Val Gln Ser Gly Ala Glu Val Val Lys Pro Gly Ala
  1               5                  10                  15

Ser Val Lys Ile Ser Cys Lys Ala Ser Gly Tyr Thr Phe Thr Asp His
             20                  25                  30

Ala Ile His Trp Val Lys Gln Asn Pro Gly Gln Arg Leu Glu Trp Ile
         35                  40                  45

Gly Tyr Phe Ser Pro Gly Asn Asp Asp Phe Lys Tyr Asn Glu Arg Phe
     50                  55                  60

Lys Gly Lys Ala Thr Ile Thr Ala Asp Thr Ser Ala Ser Thr Ala Tyr
 65                  70                  75                  80

Val Glu Leu Ser Ser Leu Arg Ser Glu Asp Thr Ala Val Tyr Phe Cys
                 85                  90                  95

Ala Arg Ser Leu Asn Met Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Glu Pro Lys Ser Cys Asp Thr Pro Pro Cys Pro
225                 230                 235                 240

Arg Cys Pro Ala Pro Gly Gly Ser Ser Gly Gly Ser Gly Gly
                245                 250                 255

Gln Pro Arg Glu Pro Gln Val Tyr Thr Leu Pro Pro Ser Arg Asp Glu
            260                 265                 270

Leu Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
```

```
            290                 295                 300
Asn Tyr Lys Thr Thr Pro Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

Val Phe Ser Cys Ser Val Met His Glu Ala Leu His Asn His Tyr Thr
                340                 345                 350

Gln Lys Ser Leu Ser Leu Ser Pro Gly Lys
                355                 360

<210> SEQ ID NO 27
<211> LENGTH: 220
<212> TYPE: PRT
<213> ORGANISM: Artificial Sequence
<220> FEATURE:
<223> OTHER INFORMATION: Synthetic construct

<400> SEQUENCE: 27

Asp Ile Val Met Ser Gln Ser Pro Asp Ser Leu Ala Val Ser Leu Gly
1               5                   10                  15

Glu Arg Val Thr Leu Asn Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Trp Ala Ser Ala Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 28
<211> LENGTH: 113
<212> TYPE: PRT
<213> ORGANISM: Artificial Sequence
<220> FEATURE:
<223> OTHER INFORMATION: Synthetic construct

<400> SEQUENCE: 28

Asp Ile Val Met Ser Gln Ser Pro Ser Ser Leu Pro Val Ser Val Gly
1               5                   10                  15
```

-continued

```
Glu Lys Val Thr Leu Ser Cys Lys Ser Ser Gln Ser Leu Leu Tyr Ser
             20                  25                  30

Gly Asn Gln Lys Asn Tyr Leu Ala Trp Tyr Gln Gln Lys Pro Gly Gln
         35                  40                  45

Ser Pro Lys Leu Leu Ile Tyr Trp Ala Ser Ala Arg Glu Ser Gly Val
     50                  55                  60

Pro Asp Arg Phe Thr Gly Ser Gly Ser Gly Thr Asp Phe Thr Leu Ser
 65                  70                  75                  80

Ile Ser Ser Val Lys Thr Glu Asp Leu Ala Val Tyr Tyr Cys Gln Gln
                 85                  90                  95

Tyr Tyr Ser Tyr Pro Leu Thr Phe Gly Ala Gly Thr Lys Leu Val Leu
            100                 105                 110

Lys
```

<210> SEQ ID NO 29
<211> LENGTH: 113
<212> TYPE: PRT
<213> ORGANISM: Artificial Sequence
<220> FEATURE:
<223> OTHER INFORMATION: Synthetic construct

<400> SEQUENCE: 29

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Ser Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Tyr Ser Phe Gly Gln Gly Thr Lys Leu Glu Ile
            100                 105                 110

Lys
```

<210> SEQ ID NO 30
<211> LENGTH: 113
<212> TYPE: PRT
<213> ORGANISM: Artificial Sequence
<220> FEATURE:
<223> OTHER INFORMATION: Synthetic construct

<400> SEQUENCE: 30

```
Asp Ile Val Met Ser Gln Ser Pro Asp Ser Leu Ala Val Ser Leu Gly
 1               5                  10                  15

Glu Arg Val Thr Leu Asn Cys Lys Ser Ser Gln Ser Leu Leu Tyr Ser
             20                  25                  30

Gly Asn Gln Lys Asn Tyr Leu Ala Trp Tyr Gln Gln Lys Pro Gly Gln
         35                  40                  45

Ser Pro Lys Leu Leu Ile Tyr Trp Ala Ser Ala Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
```

```
                    85                  90                  95
Tyr Tyr Ser Tyr Pro Leu Thr Phe Gly Ala Gly Thr Lys Leu Glu Leu
                100                 105                 110

Lys

<210> SEQ ID NO 31
<211> LENGTH: 113
<212> TYPE: PRT
<213> ORGANISM: Artificial Sequence
<220> FEATURE:
<223> OTHER INFORMATION: Synthetic construct

<400> SEQUENCE: 31

Asp Ile Val Met Ser Gln Ser Pro Asp Ser Leu Ala Val Ser Leu Gly
  1               5                  10                  15

Glu Arg Val Thr Leu Asn Cys Lys Ser Ser Gln Ser Leu Leu Tyr Ser
                 20                  25                  30

Gly Asn Gln Lys Asn Tyr Leu Ala Trp Tyr Gln Gln Lys Pro Gly Gln
             35                  40                  45

Pro Pro Lys Leu Leu Ile Tyr Trp Ala Ser Ala Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                 85                  90                  95

Tyr Tyr Ser Tyr Pro Leu Thr Phe Gly Ala Gly Thr Lys Leu Glu Leu
                100                 105                 110

Lys

<210> SEQ ID NO 32
<211> LENGTH: 115
<212> TYPE: PRT
<213> ORGANISM: Artificial Sequence
<220> FEATURE:
<223> OTHER INFORMATION: Synthetic construct

<400> SEQUENCE: 32

Gln Val Gln Leu Gln Gln Ser Asp Ala Glu Leu Val Lys Pro Gly Ala
  1               5                  10                  15

Ser Val Lys Ile Ser Cys Lys Ala Ser Gly Tyr Thr Phe Thr Asp His
                 20                  25                  30

Ala Ile His Trp Val Lys Gln Asn Pro Glu Gln Gly Leu Glu Trp Ile
             35                  40                  45

Gly Tyr Phe Ser Pro Gly Asn Asp Asp Phe Lys Tyr Asn Glu Arg Phe
 50                  55                  60

Lys Gly Lys Ala Thr Leu Thr Ala Asp Lys Ser Ser Ser Thr Ala Tyr
 65                  70                  75                  80

Val Gln Leu Asn Ser Leu Thr Ser Glu Asp Ser Ala Val Tyr Phe Cys
                 85                  90                  95

Thr Arg Ser Leu Asn Met Ala Tyr Trp Gly Gln Gly Thr Ser Val Thr
                100                 105                 110

Val Ser Ser
        115

<210> SEQ ID NO 33
<211> LENGTH: 119
<212> TYPE: PRT
<213> ORGANISM: Artificial Sequence
```

```
<220> FEATURE:
<223> OTHER INFORMATION: Synthetic construct

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
            100                 105                 110

Thr Leu Val Thr Val Ser Ser
        115

<210> SEQ ID NO 34
<211> LENGTH: 115
<212> TYPE: PRT
<213> ORGANISM: Artificial Sequence
<220> FEATURE:
<223> OTHER INFORMATION: Synthetic construct

<400> SEQUENCE: 34

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser
        115

<210> SEQ ID NO 35
<211> LENGTH: 115
<212> TYPE: PRT
<213> ORGANISM: Artificial Sequence
<220> FEATURE:
<223> OTHER INFORMATION: Synthetic construct

<400> SEQUENCE: 35

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30
```

```
Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Ile Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Ala Arg Ser Leu Asn Met Ala Tyr Trp Gly Gln Gly Thr Leu Val Thr
            100                 105                 110

Val Ser Ser
        115

<210> SEQ ID NO 36
<211> LENGTH: 10
<212> TYPE: PRT
<213> ORGANISM: Artificial Sequence
<220> FEATURE:
<223> OTHER INFORMATION: Synthetic construct

<400> SEQUENCE: 36

Ile Gly Lys Thr Ile Ser Lys Lys Ala Lys
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Synthetic construct

<400> SEQUENCE: 37

Cys Pro Glu Pro Lys Ser Cys Asp Thr Pro Pro Cys Pro Arg
1               5                   10              15

<210> SEQ ID NO 38
<211> LENGTH: 1095
<212> TYPE: DNA
<213> ORGANISM: Artificial Sequence
<220> FEATURE:
<223> OTHER INFORMATION: Synthetic construct

<400> SEQUENCE: 38
gaggtgcagc tggtggagtc tgggggcggc ttggcaaagc ctggggggtc cctgagactc      60
tcctgcgcag cctccgggtt caggttcacc ttcaataact actacatgga ctgggtccgc     120
caggctccag ggcaggggct ggagtgggtc tcacgtatta gtagtagtgg tgatcccaca     180
tggtacgcag actccgtgaa gggcagattc accatctcca gagagaacgc caagaacaca     240
ctgtttcttc aaatgaacag cctgagagct gaggacacgg ctgtctatta ctgtgcgagc     300
ttgactacag ggtctgactc ctggggccag ggagtcctgg tcaccgtctc ctcagctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca agaaagttga gcccaaatct     660
tgtgacaaaa ctcacacatg cccaccgtgc ccagagccca atcttgtgca cacctcccc      720
ccatgcccac ggtgcccagc acctggaggt ggctcgagtg gaggcggttc cggagggcag     780
```

```
cccgagaac acaggtgta caccctgccc ccatcccggg atgagctgac caagaaccag    840
gtcagcctga cctgcctggt caaaggcttc tatcccagcg acatcgccgt ggagtgggag    900
agcaatgggc agccggagaa caactacaag accacgcctc ccgtgctgga ctccgacggc    960
tccttcttcc tctacagcaa gctcaccgtg gacaagagca ggtggcagca ggggaacgtc    1020
ttctcatgct ccgtgatgca tgaggctctg cacaaccact acacgcagaa gagcctctcc    1080
ctgtctccgg gtaaa                                                     1095
```

<210> SEQ ID NO 39
<211> LENGTH: 642
<212> TYPE: DNA
<213> ORGANISM: Artificial Sequence
<220> FEATURE:
<223> OTHER INFORMATION: Synthetic construct

<400> SEQUENCE: 39

```
gacatccaga tgacccagtc tccatcttcc ctgtctgcat ctgtagggga cagagtcacc     60
atcacttgca gggcaagtca ggacattagg tattatttaa attggtatca gcagaaacca    120
ggaaaagctc ctaagctcct gatctatgtt gcatccagtt tgcaaagtgg ggtcccatca    180
aggttcagcg gcagtggatc tgggacagag ttcactctca ccgtcagcag cctgcagcct    240
gaagattttg cgacttatta ctgtctacag gtttatagta cccctcggac gttcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 40
<211> LENGTH: 365
<212> TYPE: PRT
<213> ORGANISM: Artificial Sequence
<220> FEATURE:
<223> OTHER INFORMATION: Synthetic construct

<400> SEQUENCE: 40

```
Glu Val Gln Leu Val Glu Ser Gly Gly Gly Leu Ala Lys Pro Gly Gly
  1               5                  10                  15

Ser Leu Arg Leu Ser Cys Ala Ala Ser Gly Phe Arg Phe Thr Phe Asn
                 20                  25                  30

Asn Tyr Tyr Met Asp Trp Val Arg Gln Ala Pro Gly Gln Gly Leu Glu
             35                  40                  45

Trp Val Ser Arg Ile Ser Ser Gly Asp Pro Thr Trp Tyr Ala Asp
         50                  55                  60

Ser Val Lys Gly Arg Phe Thr Ile Ser Arg Glu Asn Ala Lys Asn Thr
 65                  70                  75                  80

Leu Phe Leu Gln Met Asn Ser Leu Arg Ala Glu Asp Thr Ala Val Tyr
                 85                  90                  95

Tyr Cys Ala Ser Leu Thr Thr Gly Ser Asp Ser Trp Gly Gln Gly Val
            100                 105                 110

Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Glu Pro Lys Ser Cys Asp Thr Pro Pro
225                 230                 235                 240

Pro Cys Pro Arg Cys Pro Ala Pro Gly Gly Ser Ser Gly Gly Gly
                245                 250                 255

Ser Gly Gly Gln Pro Arg Glu Pro Gln Val Tyr Thr Leu Pro Pro Ser
            260                 265                 270

Arg Asp Glu Leu Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
        355                 360                 365

<210> SEQ ID NO 41
<211> LENGTH: 214
<212> TYPE: PRT
<213> ORGANISM: Artificial Sequence
<220> FEATURE:
<223> OTHER INFORMATION: Synthetic construct

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Tyr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Glu Asp Phe Ala Thr Tyr Tyr Cys Leu Gln Val Tyr Ser Thr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 42
<211> LENGTH: 1095
<212> TYPE: DNA
<213> ORGANISM: Artificial Sequence
<220> FEATURE:
<223> OTHER INFORMATION: Synthetic construct

<400> SEQUENCE: 42
caggtccaac tgcagcaggt tggggctgaa ctggtgaagc ctggggcttc agtgaagctg      60
tcctgcaagg cttctggcta caccttcacc agctactgga tacactgggt gaagcagagg     120
cctggacagg gccttgagtg gattggagag aatgatccta gcaacggtcg tactaactac     180
aatgagaagt tcaagaacaa ggccacactg actgtagaca atcctccag cacagcctac      240 atgcatctca gcagcctgac atctgaggac tctgcggtct attactgttc aagggggcct    300
aattacttct attctatgga ctactggggt caaggaacct cagtcaccgt ctcctcagct     360
agcaccaagg gcccatcggt cttccccctg gcaccctcct ccaagagcac ctctggggc     420 acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagagc ccaaatcttg tgacacacct     720
cccccatgcc cacggtgccc agcacctgga ggtggctcga gtggaggcgg ttccggaggg     780
cagccccgag aaccacaggt gtacaccctg cccccatccc gggatgagct gaccaagaac     840
caggtcagcc tgacctgcct ggtcaaaggc ttctatccca gcgacatcgc cgtggagtgg     900
gagagcaatg ggcagccgga gaacaactac aagaccacgc ctcccgtgct ggactccgac     960
ggctccttct tcctctacag caagctcacc gtggacaaga gcaggtggca gcaggggaac    1020
gtcttctcat gctccgtgat gcatgaggct ctgcacaacc actacacgca gaagagcctc    1080
tccctgtctc cgggt                                                     1095

<210> SEQ ID NO 43
<211> LENGTH: 657
<212> TYPE: DNA
<213> ORGANISM: Artificial Sequence
<220> FEATURE:
<223> OTHER INFORMATION: Synthetic construct

<400> SEQUENCE: 43
gattttttga tgacccaaac tccactctcc ctgcctgtca gtcttggaga tcaagcctcc      60
atctcttgca gatcaagtca gagcattgta catagtaatg gaaacaccta tttagaatgg     120
```

-continued

```
tacctgcaga aaccaggcca gtctccaaag ctcctcatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcct    300
ctcacgttcg gtgctgggac caagctggag ctgaagcgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657
```

<210> SEQ ID NO 44
<211> LENGTH: 365
<212> TYPE: PRT
<213> ORGANISM: Artificial Sequence
<220> FEATURE:
<223> OTHER INFORMATION: Synthetic construct

<400> SEQUENCE: 44

```
Gln Val Gln Leu Gln Gln Val Gly Ala Glu Leu Val Lys Pro Gly Ala
  1               5                  10                  15

Ser Val Lys Leu Ser Cys Lys Ala Ser Gly Tyr Thr Phe Thr Ser Tyr
             20                  25                  30

Trp Ile His Trp Val Lys Gln Arg Pro Gly Gln Gly Leu Glu Trp Ile
         35                  40                  45

Gly Glu Asn Asp Pro Ser Asn Gly Arg Thr Asn Tyr Asn Glu Lys Phe
     50                  55                  60

Lys Asn Lys Ala Thr Leu Thr Val Asp Lys Ser Ser Thr Ala Tyr
 65                  70                  75                  80

Met His Leu Ser Ser Leu Thr Ser Glu Asp Ser Ala Val Tyr Tyr Cys
                 85                  90                  95

Ser Arg Gly Pro Asn Tyr Phe Tyr Ser Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Glu Pro Lys Ser Cys Asp Thr Pro
225                 230                 235                 240

Pro Pro Cys Pro Arg Cys Pro Ala Pro Gly Gly Ser Ser Gly Gly
                245                 250                 255

Gly Ser Gly Gly Gln Pro Arg Glu Pro Gln Val Tyr Thr Leu Pro Pro
            260                 265                 270
```

```
Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
        290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
                340                 345                 350

Asn His Tyr Thr Gln Lys Ser Leu Ser Leu Ser Pro Gly
                355                 360                 365

<210> SEQ ID NO 45
<211> LENGTH: 219
<212> TYPE: PRT
<213> ORGANISM: Artificial Sequence
<220> FEATURE:
<223> OTHER INFORMATION: Synthetic construct

<400> SEQUENCE: 45

Asp Phe Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 46
<211> LENGTH: 1107
<212> TYPE: DNA
<213> ORGANISM: Artificial Sequence
<220> FEATURE:
<223> OTHER INFORMATION: Synthetic construct
```

-continued

```
<400> SEQUENCE: 46
caggtacaac tgcagcagcc tggggctgag ctggtgaagc ctggggcctc agtgaagatg      60
tcctgcaagg cttctggcta cacatttacc agttacaata tgcactgggt aaaacagaca     120
cctggtcggg gcctggaatg gattggagct atttatcccg gaaatggtga tacttcctac     180
aatcagaagt tcaaaggcaa ggccacattg actgcagaca atcctccag cacagcctac      240 atgcagctca gcagcctgac atctgaggac tctgcggtct attactgtgc aagatcgact     300
tactacggcg gtgactggta cttcaatgtc tggggcgcag ggaccacggt caccgtctct     360
gcagctagca ccaagggccc atcggtcttc cccctggcac cctcctccaa gagcacctct     420
gggggcacag cggccctggg ctgcctggtc aaggactact ccccgaaccc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagagcccaa atcttgtgac     720
acacctcccc catgcccacg gtgcccagca cctggaggtg gctcgagtgg aggcggttcc     780
ggagggcagc cccgagaacc acaggtgtac accctgcccc catcccggga tgagctgacc     840
aagaaccagg tcagcctgac ctgcctggtc aaaggcttct atcccagcga catcgccgtg     900
gagtgggaga gcaatgggca gccggagaac aactacaaga ccacgcctcc cgtgctggac     960
tccgacggct ccttcttcct ctacagcaag ctcaccgtgg acaagagcag gtggcagcag    1020
gggaacgtct tctcatgctc cgtgatgcat gaggctctgc acaaccacta cacgcagaag    1080
agcctctccc tgtctccggg taaatga                                        1107
```

<210> SEQ ID NO 47
<211> LENGTH: 368
<212> TYPE: PRT
<213> ORGANISM: Artificial Sequence
<220> FEATURE:
<223> OTHER INFORMATION: Synthetic construct

<400> SEQUENCE: 47

```
Gln Val Gln Leu Gln Gln Pro Gly Ala Glu Leu Val Lys Pro Gly Ala
 1               5                  10                  15

Ser Val Lys Met Ser Cys Lys Ala Ser Gly Tyr Thr Phe Thr Ser Tyr
             20                  25                  30

Asn Met His Trp Val Lys Gln Thr Pro Gly Arg Gly Leu Glu Trp Ile
         35                  40                  45

Gly Ala Ile Tyr Pro Gly Asn Gly Asp Thr Ser Tyr Asn Gln Lys Phe
     50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Glu Pro Lys Ser Cys Asp
225                 230                 235                 240

Thr Pro Pro Pro Cys Pro Arg Cys Pro Ala Pro Gly Gly Gly Ser Ser
            245                 250                 255

Gly Gly Gly Ser Gly Gly Gln Pro Arg Glu Pro Gln Val Tyr Thr Leu
            260                 265                 270

Pro Pro Ser Arg Asp Glu Leu Thr Lys Asn Gln Val Ser Leu Thr Cys
        275                 280                 285

Leu Val Lys Gly Phe Tyr Pro Ser Asp Ile Ala Val Glu Trp Glu Ser
290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
            325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 48
<211> LENGTH: 642
<212> TYPE: DNA
<213> ORGANISM: Artificial Sequence
<220> FEATURE:
<223> OTHER INFORMATION: Synthetic construct

<400> SEQUENCE: 48
caaattgttc tctcccagtc tccagcaatc ctgtctgcat ctccagggga gaaggtcaca      60
atgacttgca gggccagctc aagtgtaagt tacatccact ggttccagca gaagccagga    120
tcgtccccca aaccctggat ttatgccaca tccaacctgg cttctggagt ccctgttcgc    180
ttcagtggca gtgggtctgg gacttcttac tctctcacaa tcagcagagt ggaggctgaa    240
gatgctgcca cttattactg ccagcagtgg actagtaacc cacccacgtt cggagggggg    300
accaagctgg aaatcaaacg tacggtggct gcaccatctg tcttcatctt cccgccatct    360
gatgagcagt tgaaatctgg aactgcctct gttgtgtgcc tgctgaataa cttctatccc    420
agagaggcca aagtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt ga                       642

<210> SEQ ID NO 49
<211> LENGTH: 213
<212> TYPE: PRT
<213> ORGANISM: Artificial Sequence
<220> FEATURE:
<223> OTHER INFORMATION: Synthetic construct
```

<400> SEQUENCE: 49

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 50
<211> LENGTH: 7
<212> TYPE: PRT
<213> ORGANISM: Artificial Sequence
<220> FEATURE:
<223> OTHER INFORMATION: Synthetic construct

<400> SEQUENCE: 50

Glu Ser Lys Tyr Gly Pro Pro
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic construct

<400> SEQUENCE: 51

Cys Pro Ser Cys Pro
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic construct -continued

```
<400> SEQUENCE: 52

Ala Pro Glu Phe Leu Gly Gly Pro
1               5

<210> SEQ ID NO 53
<211> LENGTH: 29
<212> TYPE: PRT
<213> ORGANISM: Artificial Sequence
<220> FEATURE:
<223> OTHER INFORMATION: Synthetic construct

<400> SEQUENCE: 53

Glu Ser Lys Tyr Gly Pro Pro Cys Pro Ser Cys Pro Glu Pro Lys Ser
1               5                   10                  15

Cys Asp Thr Pro Pro Pro Cys Pro Arg Cys Pro Ala Pro
            20                  25
```

PURIFICATION AND PREFERENTIAL SYNTHESIS OF BINDING MOLECULES

RELATED APPLICATIONS

This application claims priority to U.S. Ser. No. 60/483,877, titled "Purification and Preferential Synthesis of Polypeptides," filed on Jun. 27, 2003 and to U.S. Ser. No. 60/508,810, titled "Purification and Preferential Synthesis of Antigen Binding Polypeptides," filed Oct. 3, 2003. This application also claims priority to U.S. Ser. No. 60/515,351, titled "Modified Antibody Molecules Comprising Connecting Peptides," Oct. 28, 2003 and to U.S. Ser. No. 60/516,030, titled "Modified Antibody Molecules Comprising Connecting Peptides," filed Oct. 30, 2003. This application is also related to U.S. Ser. No. 10/880,028, titled "Modified Binding Molecules Comprising Connecting Peptides" filed on Jun. 28, 2004. The contents of these applications are incorporated in their entirety by this reference.

BACKGROUND OF THE INVENTION

Antibodies are dimeric molecules; each monomer making up the dimer comprises one light and one heavy chain. Solutions of antibody molecules exist in two forms associated with hinge heterogeneity. Using SDS-PAGE analysis of purified Mab MAb, typically the two forms are observed as two protein bands, a major band (MW approximately 150-160 kDa) and a minor band (MW approximately 75-80 kDa). This latter form is typically observed after SDS-PAGE analysis of purified IgG4 preparations, but can be identified at much lower frequencies in all IgG isotypes, including purified, recombinant MAbs (Angal et al. 1993. *Mol. Immunol.* 30:105; Norderhaug et al. 1990. *Eur. J. Immunol.* 21:2370). The larger molecular weight isoform, referred to as Form A, contains covalent interchain disulfide bonds at positions corresponding to 239 and 242, Kabat numbering system (positions 226 and 229, EU numbering system) (Kabat, E, Wu, T T, Perry, H M, Gottesman, K S, Foeller, C: Sequences of Proteins of Immunological Interest. Bethesda, US Department of Health and Human Services, NIH, 1991). The second isoform, Form B, is thought to contain no covalent linkages between the two heavy chains and an intrachain disulfide bond between the two neighboring cysteine residues as evidenced by the 75-80 kDa seen in non-reducing SDS-PAGE electrophoresis. The two heavy chains of Form B are presumably held together by strong non-covalent (e.g., ionic) interactions associated with the CH3 domain region of the molecule. These mixtures of A and B forms are not present in solutions of MAb fragments that contain an intact hinge, but lack a CH3 domain, such as, for example, $F(ab)_2$ fragments. Typically, genetically engineered or enzymatically digested $F(ab)_2$ MAb preparations lack the B-form, since the molecule lacks the necessary domains for maintaining non-covalent interactions (e.g., hydrogen bonding). However, they are present in MAb preparations that do contain a CH3 domain, such as IgG4, the CH2 domain deleted MAb fragments (e.g., as described in 02/060955 A2) and minibodies (see, e.g., Hu et al. 1996. Cancer Research 56:3055) as well as in IgG4 molecule.

The application of protein engineering techniques to therapeutic antibody design has also produced a number of antibody formats that have been shown to have altered, and in some cases, improved pharmacodynamic, biodistribution, and activity profiles. Some altered antibody molecules have been made in which the number of cysteine residues in the hinge region is reduced to one to facilitate assembly of antibody molecules as it is only necessary to form a single disulfide bond. This also provides a specific target for attaching the hinge region either to another hinge region or to an effector or reporter molecule (U.S. Pat. No. 5,677,425). The number of cysteine residues in the antibody hinge has also been increased (U.S. Pat. No. 5,677,425). Other mutated antibodies have been constructed in which the IgG1 hinge region and the CH2 domain have been replaced with the human IgG3 hinge region. (WO 97/11370). These molecules contain 11 sulfhydryl groups for substitution of multiple haptens via thiol groups.

CH2 domain deleted antibodies have a molecular mass of approximately 120 kDa and have been shown to penetrate tumors significantly better than full length IgG. Minibodies, which also have deletion of the CH2 domain, have similar characteristics. These domain deleted molecules accumulate at tumor sites more efficiently than other MAb fragments, such as $F(ab)'_2s$, but without the unfavorable pharmacodynamic profiles seen with intact IgG antibody. CH2 domain deleted antibodies consist of a VLCL light chain and a VH1 heavy chain domain and a portion of the hinge region (e.g., the upper and middle hinge) genetically fused (either directly or through a synthetic peptide spacer) to a CH3 domain. As an example, the biosynthesis of recombinant CH2 domain deleted ddCC49, a domain deleted antibody that recognizes the tumor associated TAG72 antigen expressed on a variety of human carcinomas, produces the A and B forms in approximately 50:50 distribution in cell cultures. Cells engineered to express alternative forms of CH2 domain deleted antibodies, for example, tetravalent CH2 domain deleted antibodies, minibodies, or tetravalent minibodies also express a mixture consisting of A and B forms and/or monomeric half-mer molecules.

Form A and Form B are extremely difficult to separate even after MAb purification, since they are composed of identical amino acids and, therefore, have identical molecular weight and similar physical and chemical properties. They cannot be separated by standard gel filtration, affinity chromatography, or ion exchange chromatography typically used to purify antibody molecules, including recombinant MAb proteins. Current manufacturing processes discard at least 50% of the total antibody produced, having a negative impact on overall yield. Moreover, the presence of the two isoforms increases efforts required for downstream processing. Thus, a method of separating forms A and B or of increasing biosynthesis of one or the other form of antibody would be of great benefit.

SUMMARY OF THE INVENTION

The invention is based, at least in part, on the finding that in a composition comprising a mixture of dimeric polypeptide molecules comprising different isoforms (molecules comprising two heavy chain portions in which a fraction of the molecules comprise two heavy chain portions that are linked via at least one interchain disulfide linkage (Form A) and a portion of the molecules comprise two heavy chain portions that are not linked via at least one interchain disulfide linkage (Form B)) one form or the other can be preferentially obtained, e.g., by separation using-hydrophobic interaction chromatography or by inclusion of synthetic connecting peptides which result in the preferential biosynthesis of either Form A or Form B. The connecting peptides of the invention can be included in any dimeric molecule that tends to form both Form A and Form B, e.g., antibody molecules, domain deleted antibody molecules (e.g., lacking all or part of a CH2 domain), minibodies, diabodies, fusion proteins, etc. In a preferred embodiment, the formation of Form A is enhanced.

Form A polypeptide dimers show enhanced stability in vitro and enhanced biodistribution in vivo.

Accordingly, in one aspect, the invention pertains to a composition comprising polypeptide dimers having at least two binding sites and at least two polypeptide chains, wherein said at least two polypeptide chains comprise at least one heavy chain portion and a synthetic connecting peptide, wherein greater than 50% of the polypeptide dimers are linked via at least one interchain disulfide linkage.

In one embodiment, greater than 90% of the polypeptide dimers are linked via at least one interchain disulfide linkage.

In one embodiment, the polypeptide chains comprise a CH3 domain genetically fused to a VL, VH or CH1 via the connecting peptide.

In one embodiment, the polypeptide chains lack all or part of a CH2 domain.

In one embodiment, the polypeptide dimers are linked via two or more interchain disulfide linkages.

In one embodiment, the heavy chain portion is derived from an antibody of an isotype selected from the group consisting of: IgG1, IgG2, IgG3, and IgG4.

In one embodiment, the heavy chain portion comprises an amino acid sequence derived from a hinge region selected from the group consisting of: a γ1 hinge, a γ2 hinge, a γ3 hinge, and a γ4 hinge.

In one embodiment, wherein the heavy chain portion comprises a chimeric hinge.

In one embodiment, the synthetic connecting peptide comprises at least a portion of an IgG1 hinge domain, at least a portion of an IgG3 hinge domain.

In one embodiment, the binding sites are individually selected from the group consisting of: an antigen binding site, a ligand binding portion of a receptor, and a receptor binding portion of a ligand.

In one embodiment, the polypeptide dimer comprises four polypeptide chains.

In another embodiment, two of the polypeptide chains comprise at least one heavy chain portion and a synthetic connecting peptide.

In another aspect, the invention pertains to a composition comprising polypeptide dimers having at least two binding sites and at least two polypeptide chains, wherein said at least two polypeptide chains comprise at least one heavy chain portion and a synthetic connecting peptide, wherein greater than about 50% of the polypeptide dimers are linked via at least one interchain disulfide linkage and wherein the connecting peptide comprises a proline residue at position 243 of the Kabat numbering system.

In one embodiment, greater than 90% of the polypeptide dimers are linked via at least one interchain disulfide linkage.

In one embodiment, the synthetic connecting peptide further comprises a cysteine residue at position 239 or 242 of the Kabat numbering system.

In one embodiment, at least one of the polypeptide chains comprises a CH3 domain linked to a VL, VH or CH1 domain via the connecting peptide.

In one embodiment, the synthetic connecting peptide further comprises an alanine residue at position 244 and a proline residue at position 245 of the Kabat numbering system.

In another aspect, the invention pertains to a method of treating a subject that would benefit from treatment with a binding molecule comprising administering a composition of the invention to the subject such that treatment occurs.

In one embodiment, the subject is suffering from cancer.

In one embodiment, the subject is suffering from lymphoma.

In one embodiment, the subject is suffering from an autoimmune disease or disorder.

In one embodiment, the subject is suffering from an inflammatory disease or disorder.

In one embodiment, the binding sites are individually selected from the group consisting of: an antigen binding site, a ligand binding portion of a receptor, and a receptor binding portion of a ligand.

In another aspect, the invention pertains to a nucleic acid molecule comprising a nucleotide sequence encoding a polypeptide chain of the invention.

In another aspect, the invention pertains to a host cell comprising the nucleic acid molecule of claim 23.

In one embodiment, the polypeptide dimers comprise four polypeptide chains and wherein two of the polypeptide chains comprise at least one heavy chain portion and a synthetic connecting peptide.

In one aspect, the invention pertains to a connecting peptide comprising an amino acid sequence selected from the group consisting of: SEQ ID NOs: 8-15 and 53.

In one aspect, the invention pertains to a connecting peptide consisting of an amino acid sequence selected from the group consisting of: SEQ ID NOs: 8-15 and 53.

In one aspect, the invention pertains to a nucleic acid molecule encoding a polypeptide chain, wherein the nucleic acid molecule comprises a nucleotide sequence selected from the group consisting of: SEQ ID NOs:16, 20, 21, 38, 42, 46 and 47.

In one aspect, the invention pertains to a nucleic acid molecule encoding a polypeptide chain, wherein the nucleic acid molecule comprises a nucleotide sequence selected from the group consisting of: SEQ ID NOs:24 and 25.

In one aspect, the invention pertains to a domain deleted antibody molecule comprising an amino acid sequence selected from the group consisting of: SEQ ID NOs: 18, 22, 23, 40, and 44.

In one aspect, the invention pertains to a domain deleted antibody molecule comprising an amino acid sequence selected from the group consisting of: SEQ ID NOs: 26 and 27.

In one aspect, the invention pertains to an antibody molecule comprising the amino acid sequence shown in SEQ ID NO: 31.

In one aspect, the invention pertains to an antibody molecule comprising the amino acid sequence shown in SEQ ID NO: 35.

In one aspect, the invention pertains to a method for separating a first and a second polypeptide dimer wherein the first polypeptide dimer comprises at least two binding sites and at least two polypeptide chains, wherein said at least two polypeptide chains comprises a heavy chain portion and wherein the first polypeptide dimer is linked via at least one disulfide linkage and wherein the second polypeptide dimer comprises at least two binding sites and at least two polypeptide chains, wherein said at least two polypeptide chains comprises a heavy chain portion and wherein the second polypeptide dimer is not linked via at least one disulfide linkage, comprising the steps of:

i) contacting a mixture comprising the first and the second polypeptide dimers with a medium that separates the polypeptide dimers based on hydrophobic interaction under conditions that allow the second polypeptide dimmer to bind to the medium; and ii) collecting the first polypeptide dimer to thereby separate the first and the collecting step comprises contacting the medium with a solution having a conductivity of approximately 120 mS/cm at approximately neutral pH.

In one embodiment the conductivity is approximately 116 mS/cm.

In one embodiment the method further comprises contacting the medium with a solution having a conductivity of approximately 140 mS/cm and at approximately neutral pH prior to step ii) such that both the first and second polypeptide dimers bind to the medium.

In one embodiment, the polypeptide chains comprise a CH3 domain linked to a VL, VH or CH1 domain via a synthetic connecting peptide.

In one embodiment, the heavy chain portions of the first and second polypeptide dimers are derived from an antibody of an isotype selected from the group consisting of: IgG1, IgG2, IgG3, and IgG4.

In one embodiment, the heavy chain portions comprises an amino acid sequence derived from a hinge region selected from the group consisting of: a γ1 hinge, a γ2 hinge a γ3 hinge, and a γ4 hinge.

In one embodiment, the binding sites are individually selected from the group consisting of: an antigen binding site, a ligand binding portion of a receptor, and a receptor binding portion of a ligand.

In one embodiment, at least one binding site of a polypeptide dimer comprises at least one CDR from an antibody selected from the group consisting of: 2B8, Lym 1, Lym 2, LL2, Her2, B1, MB1, BH3, B4, B72.3, CC49, and 5E10.

In one embodiment, at least one binding site of a polypeptide dimer comprises the receptor binding portion of a ligand.

In one embodiment, at least one binding site of a polypeptide dimer comprises the ligand binding portion of a receptor.

In another aspect, the invention pertains to a method of treating a subject that would benefit from treatment with a binding molecule comprising administering a composition of the invention to the subject such that treatment occurs.

In one embodiment, the polypeptide dimers comprise four polypeptide chains and wherein two of the polypeptide chains comprise at least one heavy chain portion.

In another aspect, the invention pertains to a method for separating a first properly folded antibody molecule from a second improperly folded antibody molecule, wherein each of the first and second antibody molecules comprises four polypeptide chains, wherein at least two of the chains comprise at least one heavy chain portion, and at least two of the chains comprise at least one light chain portion, the method comprising the steps of:
  i) contacting a mixture comprising the first and second antibody molecules with a medium that separates antibody molecules based on hydrophobic interaction;
  ii) contacting the medium with a solution having a conductivity of approximately 120 mS/cm and at an approximately neutral pH, such that the first antibody molecule is not bound to the medium and the second antibody molecule is bound to the medium, thereby separating the first and second antibody molecules.

In one embodiment, the invention pertains to a method for increasing the amount of a first polypeptide dimer relative to the amount of a second polypeptide dimer produced by a cell, wherein the first and second polypeptide dimers comprise at least two binding sites and at least two polypeptide chains, said at least two polypeptide chains comprising a heavy chain portion, wherein the first dimer is linked via at least one disulfide linkage and wherein the second dimer is not linked via at least one disulfide linkage, the method comprising the step of engineering said polypeptide chain to include a synthetic connecting peptide, such that the amount of the first polypeptide dimer produced by the cell is increased relative to the amount of the second polypeptide dimer.

In one embodiment, the invention pertains to a composition comprising a first polypeptide prepared by the methods of the invention.

In one embodiment, the polypeptide dimers comprise four polypeptide chains and wherein two of the polypeptide chains comprise at least one heavy chain portion and a synthetic connecting peptide.

In one embodiment, the invention pertains to a polypeptide comprising a synthetic connecting peptide which comprises the amino acid sequence of SEQ ID NO: 37, wherein the polypeptide is not a naturally occurring IgG3 molecule.

In one embodiment, the molecule is an IgG4 molecule.

In one embodiment, the polypeptide binds to VLA-4.

In one aspect, the invention pertains to a method for increasing the amount of dimers linked via at least one disulfide linkage in a population of IgG4 molecules produced by a cell, comprising the step of causing the cell to express an IgG4 molecule comprising a synthetic connecting peptide, such that the amount dimers linked via at least one disulfide linkage in a population of IgG4 molecules is increased.

In one aspect, the invention pertains to composition comprising polypeptide dimers having at least two binding sites and at least two polypeptide chains, wherein said at least two polypeptide chains comprise at least one heavy chain portion and lacks all or part of a CH2 domain, wherein greater than 50% of the polypeptide dimers are linked via at least one interchain disulfide linkage.

In one aspect, the invention pertains to composition of claim 1 or 31.

BRIEF DESCRIPTION OF THE DRAWINGS

FIG. 4A (SEQ ID NO: 16) shows the single-stranded DNA sequence of heavy chain CH2 domain-deleted huCC49 Pro243Ala244Pro245+[Gly/Ser] hinge connecting peptide. FIG. 4B (SEQ ID NO: 17) shows the single-stranded DNA sequence of light chain CH2 domain-deleted huCC49.

FIGS. 7A-C shows peptide mapping HPLC-MS of hinge-engineered HuCC49□CH2 antibodies. FIG. 7A is Endo Lys-C non-reduced. FIG. 7B is Endo Lys-C reduced. FIG. 7C is Tryptic. G1/G3: PAP fragment H146-208 shows a shift in retention time relative to PAP and HuCC49□CH2 resulting from a Leu→Met mutation due to a PCR artifact. This was corrected in all subsequent constructs.

FIG. 8A (SEQ ID NO: 18) shows the amino acid sequence of heavy chain CH2 domain-deleted huCC49 Pro243Ala244Pro245+[Gly/Ser] hinge connecting peptide. FIG. 8B (SEQ ID NO: 19) shows the amino acid sequence of light chain CH2 domain-deleted huCC49.

FIG. 9 (SEQ ID NO: 20) shows the single-stranded DNA sequence of heavy chain CH2 domain-deleted huCC49 G1/G3/Pro243+[Gly/Ser] hinge connecting peptide.

FIG. 10 (SEQ ID NO: 21) shows the single-stranded DNA sequence of heavy chain CH2 domain-deleted huCC49 containing G1/G3/Pro243Ala244Pro245+[Gly/Ser] hinge connecting peptide.

FIG. 11 (SEQ ID NO: 22) shows the amino acid sequence of heavy chain CH2 domain-deleted huCC49 G1/G3/Pro243+[Gly/Ser] hinge connecting peptide.

FIG. 12 (SEQ ID NO: 23) shows the amino acid sequence of heavy chain CH2 domain-deleted huCC49 containing G1/G3/Pro243Ala244Pro245+[GlySer] hinge connecting peptide.

FIG. 13A (SEQ ID NO: 24) shows the DNA sequence of heavy chain CH2 domain-deleted huCC49 V2 containing G1/G3/Pro243Ala244Pro245+[GlySer] hinge connecting peptide. FIG. 13B (SEQ ID NO: 25) shows the DNA sequence of light chain CH2 domain-deleted huCC49 V2.

FIG. 14A (SEQ ID NO: 26) shows the amino acid sequence of heavy chain CH2 domain-deleted huCC49 V2 containing G1/G3/Pro243Ala244Pro245+[GlySer] hinge connecting peptide. FIG. 14B (SEQ ID NO: 27) shows the amino acid sequence of light chain CH2 domain-deleted huCC49 V2.

FIG. 17A-B shows the separation of the two CH2 domain-deleted huCC49 isoforms at a preparative scale. The first two peaks comprise the isocratic elution of Form A, the second peak shows the eluted Form B, while the third peak contains impurities, which are removed from the stationary phase during cleaning.

FIG. 19A shows an alignment of the light chain variable regions of murine CC49 (SEQ ID NO:28), LEN (SEQ ID NO:29) humanized CC49 V1 (version 1) (SEQ ID NO:30), and humanized CC49 V2 (version 2; which comprises one amino acid substitution in the light chain as compared to humanized CC49 V1, see underlined amino acid) (SEQ ID NO:31) and FIG. 19B shows alignment of the heavy chain variable regions of murine CC49 (SEQ ID NO:32), 21/28' CL (SEQ ID NO:33), humanized CC49 V1 (SEQ ID NO:34), and humanized CC49 V2 (which comprises two amino acid substitutions in the heavy chain as compared to humanized CC49, see underlined amino acids (SEQ ID NO:35).

FIG. 25A (SEQ ID NO: 46) shows the DNA sequence of the heavy chain CH2 domain-deleted anti-CD20 IgG1 C2B8 containing the G1/G3/Pro243Ala244Pro245+[GlySer] hinge connecting peptide. FIG. 25B (SEQ ID NO: 47) shows the corresponding amino acid sequence of heavy chain C2B8 containing the G1/G3/Pro243Ala244Pro245+[GlySer] hinge connecting peptide.

FIG. 26A (SEQ ID NO: 48) shows the DNA sequence of the light chain CH2 domain-deleted anti-CD20 IgG1 C2B8. FIG. 26B (SEQ ID NO: 49) shows the corresponding amino acid sequence of light chain C2B8.

FIG. 28 A (SEQ ID NO: 38) shows the DNA sequence of heavy chain CH2 domain-deleted the anti-CD23 Ab 5E8 containing the G1/G3/Pro243Ala244Pro245+[GlySer] hinge connecting peptide. FIG. 28B (SEQ ID NO: 39) shows the DNA sequence of light chain CH2 domain-deleted the anti-CD23 5E8.

FIG. 29A (SEQ ID NO: 40) shows the amino acid sequence of heavy chain CH2 domain-deleted anti-CD23 antibody 5E8 containing G1/G3/Pro243Ala244Pro245+[GlySer] hinge connecting peptide. FIG. 29B (SEQ ID NO: 41) shows the amino acid sequence of light chain CH2 domain-deleted anti-CD23 antibody 5E8.

FIG. 32 A (SEQ ID NO: 42) shows the DNA sequence of heavy chain CH2 domain-deleted chB3F6 containing G1/G3/Pro243Ala244Pro245+[GlySer] hinge connecting peptide. FIG. 32B (SEQ ID NO: 43) shows the DNA sequence of light chain CH2 domain-deleted chB3F6.

FIG. 33A (SEQ ID NO: 44) shows the amino acid sequence of heavy chain CH2 domain-deleted chB3F6 containing G1/G3/Pro243Ala244Pro245+[GlySer] hinge connecting peptide. FIG. 33B (SEQ ID NO: 45) shows the amino acid sequence of light chain CH2 domain-deleted chB3F6.

DETAILED DESCRIPTION OF THE INVENTION

Figure 1:
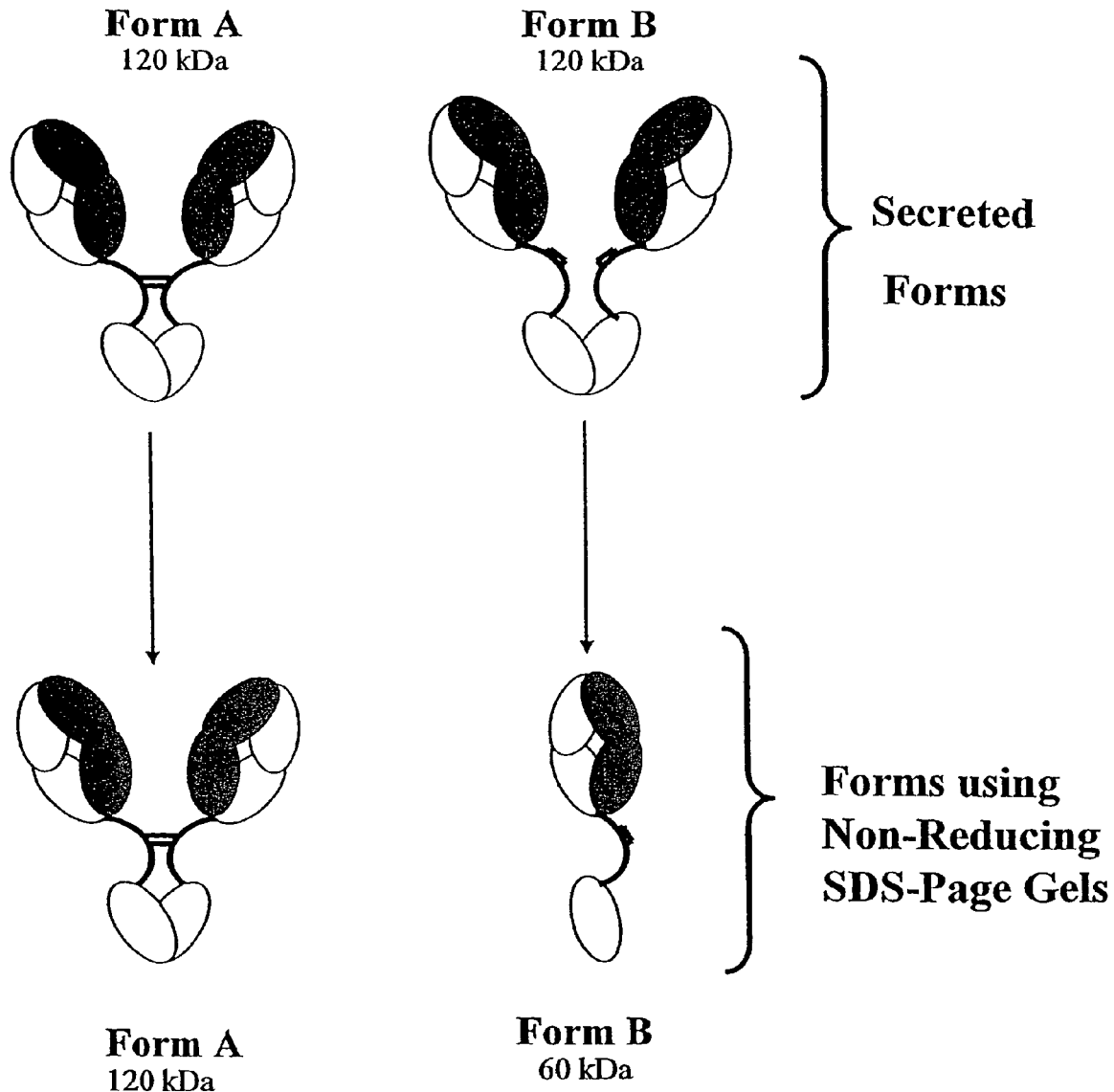
FIG. 1 shows Form A which appears as a 120 kDa dimer and Form B which appears as a 60 kDa monomer in domain deleted antibodies.

Human immunoglobulins (Igs), including monoclonal antibodies (MAbs), can exist in two forms that are associated with hinge heterogeneity. In native solutions, both of these forms are present as dimeric proteins (each monomer comprising one heavy chain and one light chain). One immunoglobulin molecule comprises a stable four chain construct of approximately 150-160 kDa in which the dimers are held together by an interchain heavy chain disulfide bond (Form A) and one comprises a form in which the dimers are not linked via interchain disulfide bonds (Form B). Form B also forms a stable dimer under native conditions, but can be identified under denaturing, non-reducing conditions, in which the heavy chains dissociate yielding a 75-80 kDa molecule. These forms have been extremely difficult to separate, even after MAb affinity purification.

The frequency of appearance of the B form in various intact IgG isotypes is due to, but not limited to, structural differences associated with the hinge region isotype of the MAb molecule. In fact, a single amino acid substitution in the hinge region of the human IgG4 hinge can significantly reduce the appearance of the B form (Angal et al. 1993. Molecular Immunology 30:105) to levels typically observed using a human IgG1 hinge. However, applying this same amino acid substitution to MAb fragments in which the CH3 domain was retained did not eliminate Form B from preparations. Typically, all recombinant CH2 domain deleted antibodies produced in cell cultures often result in hinge heterogeneity which is not corrected via similar molecular mutations in the hinge.

The instant invention advances the state of the art by providing methods of, e.g., separating a first dimeric polypeptide having from a second dimeric polypeptide wherein the first and second polypeptides comprise at least two polypeptide chains and at least two of the polypeptide chains comprise at least one heavy chain portion. In one embodiment, the polypeptides of the invention lack all or part of a CH2 domain. The monomers are linked via at least one interchain disulfide linkage (referred to herein as "Form A") and the monomers of the second polypeptide are not linked via at least one interchain disulfide linkage (referred to herein as "Form B"). These forms can be separated from each other using hydrophobic interaction chromatography. In addition, the invention pertains to polypeptides that comprise connecting peptides. The inclusion of certain connecting peptides results in the preferential biosynthesis of polypeptide dimers that are linked via at least one interchain disulfide linkage or that are not linked via at least one interchain disulfide linkage.

Before further description of the invention, for convenience, certain terms are described below:

I. DEFINITIONS

The polypeptides of the invention are binding molecules, i.e., polypeptide molecules or the nucleic acid molecules that encode them, that comprise at least one binding domain which comprises a binding site that specifically binds to a target molecule (such as an antigen or binding partner). For example, in one embodiment, a binding molecule of the invention comprises an immunoglobulin antigen binding site or the portion of a receptor molecule responsible for ligand binding or the portion of a ligand molecule that is responsible for receptor binding. The binding molecules of the invention are polypeptides or the nucleic acid molecules which encode them.

In one embodiment, the binding molecules comprise at least two binding sites. In one embodiment, the binding molecules comprise two binding sites. In one embodiment, the binding molecules comprise three binding sites. In another embodiment, the binding molecules comprise four binding sites.

The polypeptides of the invention are multimers. For example, in one embodiment, the polypeptides of the invention are dimers. In one embodiment, the dimers of the invention are homodimers, comprising two identical monomeric subunits. In another embodiment, the dimers of the invention are heterodimers, comprising two non-identical monomeric subunits. The subunits of the dimer may comprise one or more polypeptide chains. For example, in one embodiment, the dimers comprise at least two polypeptide chains. In one embodiment, the dimers comprise two polypeptide chains. In another embodiment, the dimers comprise four polypeptide chains (e.g., as in the case of antibody molecules).

The polypeptides of the invention comprise at least one amino acid sequence derived from an immunoglobulin domain. A polypeptide or amino acid sequence "derived from" a designated protein refers to the origin of the polypeptide. Preferably, the polypeptide or amino acid sequence which is derived from a particular starting polypeptide or amino acid sequence has an amino acid sequence that is essentially identical to that of the starting sequence, or a portion thereof wherein the portion consists of at least 10-20 amino acids, preferably at least 20-30 amino acids, more preferably at least 30-50 amino acids, or which is otherwise identifiable to one of ordinary skill in the art as having its origin in the starting sequence.

Preferred binding polypeptides comprise an amino acid sequence derived from a human amino acid sequence. However, binding polypeptides may comprise one or more amino acids from another mammalian species. For example, a primate heavy chain portion, hinge portion, or binding site may be included in the subject binding polypeptides and/or connecting polypeptides. Alternatively, one or more murine amino acids may be present in a binding polypeptide, e.g., in an antigen binding site of a binding molecule. Preferred binding molecules of the invention are not immunogenic.

It will also be understood by one of ordinary skill in the art that the binding molecules of the invention (e.g., the heavy chain or light chain portions or binding portions of the subject polypeptides) may be modified such that they vary in amino acid sequence from the naturally occurring immunoglobulin molecule from which they were derived. For example, nucleotide or amino acid substitutions leading to conservative substitutions or changes at "non-essential" amino acid residues may be made.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into polypeptides of the invention and screened for their ability to bind to the desired antigen.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, a polypeptide of the invention comprises a polypeptide chain comprising a CH1 domain, at least a portion of a hinge domain, and a CH2 domain. In another embodiment, a polypeptide of the invention comprises a polypeptide chain comprising a CH1 domain and a CH3 domain. In another embodiment, a polypeptide of the invention comprises a polypeptide chain comprising a CH1 domain, at least a portion of a hinge domain, and a CH3 domain. In another embodiment, a polypeptide of the invention comprises a polypeptide chain comprising a CH3 domain. In one embodiment, a polypeptide of the invention lacks at least a portion of a CH2 domain (e.g., all or part of a CH2 domain). In another embodiment, a polypeptide of the invention comprises a complete Ig heavy chain. As set forth above, it will be understood by one of ordinary skill in the art that these domains (e.g., the heavy chain portions) may be modified such that they vary in amino acid sequence from the naturally occurring immunoglobulin molecule.

In one embodiment, at least two of the polypeptide chains of a binding molecule of the invention comprise at least one heavy chain portion derived from an antibody or immunoglobulin molecule. In one embodiment, at least two heavy chain portions of a polypeptide of the invention are present on different polypeptide chains and interact, e.g., via at least one disulfide linkage (Form A) or via non-covalent interactions (Form B) to form a dimeric polypeptide, each monomer of the dimer comprising at least one heavy chain portion.

In one embodiment, the heavy chain portions of one polypeptide chain of a dimer are identical to those on a second polypeptide chain of the dimer. In one embodiment, the monomers (or half-mers) of a dimer of the invention are identical to each other. In another embodiment, they are not identical. For example, each monomer may comprise a different target binding site.

In one embodiment, a dimer of the invention is held together by covalent interactions, e.g., disulfide bonds. In one embodiment, a dimer of the invention is held together by one or more disulfide bonds. In another embodiment, a dimer of the invention is held together by one or more, preferably two disulfide bonds. In another embodiment, a dimer of the invention is held together by one or more, preferably three disulfide bonds. In another embodiment, a dimer of the invention is held together by one or more, preferably four disulfide bonds. In another embodiment, a dimer of the invention is held together by one or more, preferably five disulfide bonds. In another embodiment a dimer of the invention is held together by one or more, preferably six disulfide bonds. In another embodiment, a dimer of the invention is held together by one or more, preferably seven disulfide bonds. In another embodiment, a dimer of the invention is held together by one or more, preferably eight disulfide bonds. In another embodiment, a dimer of the invention is held together by one or more, preferably nine disulfide bonds. In another embodiment, a dimer of the invention is held together by one or more, preferably ten disulfide bonds. In a further embodiment, a dimer of the invention is not held together by disulfide bonds, but is held together, e.g., by non-covalent interactions.

The heavy chain portions of a polypeptide may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule. As used herein, the term "light chain portion" includes amino acid sequences derived from an immunoglobulin light chain. Preferably, the light chain portion comprises at least one of a VL or CL domain.

In one embodiment a polypeptide of the invention comprises an amino acid sequence or one or more moieties not derived from an Ig molecule. Exemplary modifications are described in more detail below. For example, in one embodiment, a polypeptide of the invention may comprise a flexible linker sequence. In another embodiment, a polypeptide may be modified to add a functional moiety (e.g., PEG, a drug, or a label).

In one embodiment, a binding polypeptide of the invention is a fusion protein. Fusion proteins are chimeric molecules which comprise a binding domain comprising at least one target binding site and at least one heavy chain portion. In one embodiment, a fusion protein further comprises a synthetic connecting peptide.

A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric polypeptides include fusion proteins and the chimeric hinge connecting peptides of the invention.

The term "heterologous" as applied to a polynucleotide or a polypeptide, means that the polynucleotide or polypeptide is derived from a genotypically distinct entity from that of the rest of the entity to which it is being compared. For instance, a heterologous polynucleotide or antigen may be derived from a different species origin, different cell type, or the same type of cell of distinct individuals.

The term "ligand binding domain" or "ligand binding portion" as used herein refers to any native receptor (e.g., cell surface receptor) or any region or derivative thereof retaining at least a qualitative ligand binding ability, and preferably the biological activity of a corresponding native receptor.

The term "receptor binding domain" or "receptor binding portion" as used herein refers to any native ligand or any region or derivative thereof retaining at least a qualitative receptor binding ability, and preferably the biological activity of a corresponding native ligand.

In one embodiment, a binding molecule of the invention is a fusion protein. A fusion proteins of the invention is a chimeric molecule that comprises a binding domain (which comprises at least one binding site) and a dimerization domain (which comprises at least one heavy chain portion). The heavy chain portion may be from any immunoglobulin, such as IgG1, IgG2, IgG3, or IgG4 subtypes, IgA, IgE, IgD or IgM.

In another embodiment of the invention, a binding molecule is an "antibody-fusion protein chimera." Such molecules comprise a molecule which combines at least one binding domain of an antibody with at least one fusion protein. Preferably, the interface between the two polypeptides is a CH3 domain of an immunoglobulin molecule.

In one embodiment, the binding molecules of the invention are "antibody" or "immunoglobulin" molecules, e.g., naturally occurring antibody or immunoglobulin molecules or genetically engineered antibody molecules that bind antigen in a manner similar to antibody molecules. As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "immunoglobulin" comprises five distinct classes of antibody that can be distinguished biochemically. All five classes of antibodies are clearly within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains.

As used herein, the term "binding site" or "binding domain" comprises a region of a polypeptide which is responsible for selectively binding to a target molecule of interest (e.g. an antigen, ligand, receptor, substrate or inhibitor) Exemplary binding domains include an antibody variable domain, a receptor binding domain of a ligand, a ligand binding domain of a receptor or an enzymatic domain.

In one embodiment, the binding molecules have at least one binding site specific for a molecule targeted for reduction or elimination, e.g., a cell surface antigen or a soluble antigen.

In preferred embodiments, the binding domain is an antigen binding site. An antigen binding site is formed by variable regions that vary from one polypeptide to another. The polypeptides of the invention comprise at least two antigen binding sites. As used herein, the term "antigen binding site" includes a site that specifically binds (immunoreacts with) an antigen (e.g., a cell surface or soluble antigen). The antigen binding site includes an immunoglobulin heavy chain and light chain variable region and the binding site formed by these variable regions determines the specificity of the antibody. In one embodiment, an antigen binding molecule of the invention comprises at least one heavy or light chain CDR of an antibody molecule (e.g., the sequence of which is known in the art or described herein). In another embodiment, an antigen binding molecule of the invention comprises at least two CDRs from one or more antibody molecules. In another embodiment, an antigen binding molecule of the invention comprises at least three CDRs from one or more antibody molecules. In another embodiment, an antigen binding molecule of the invention comprises at least four CDRs from one or more antibody molecules. In another embodiment, an antigen binding molecule of the invention comprises at least five CDRs from one or more antibody molecules. In another embodiment, an antigen binding molecule of the invention comprises at least six CDRs from one or more antibody molecules. Exemplary antibody molecules comprising at least one CDR that can be included in the subject antigen binding molecules are known in the art and exemplary molecules are described herein.

The polypeptides comprising two heavy chain portions disclosed herein may be linked to form two associated Ys so there will be four binding sites forming a "tetravalent" molecule (see e.g., WO02/096948A2)). In another embodiment, tetravalent minibodies or domain deleted antibodies can be made.

The term "specificity" includes the number of potential binding sites which specifically bind (e.g., immunoreact with) a given target. A polypeptide may be monospecific and contain one or more binding sites which specifically bind a target or a polypeptide may be multispecific and contain two or more binding sites which specifically bind the same or different targets.

In one embodiment, a binding molecule of the invention is a bispecific molecule (e.g., antibody, minibody, domain deleted antibody, or fusion protein having binding specificity for more than one molecule, e.g., more than one antigen or more than one epitope on the same antigen. In one embodiment, the bispecific molecules have at least one target binding site specific for a molecule targeted for reduction or elimination and a targeting molecule on a cell. In another embodiment, the bispecific molecules have at least one target binding site specific for a molecule targeted for reduction or elimination and at least one target binding site specific for a drug. In yet another embodiment, the bispecific molecules have at least one target binding site specific for a molecule targeted for reduction or elimination and at least one target binding site specific for a prodrug. In a preferred embodiment, the bispecific molecules are tetravalent antibodies that have two target binding sites specific for one target and two target binding sites specific for the second target. A tetravalent bispecific molecule may be bivalent for each specificity. Further description of bispecific molecules is provided below.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen).

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; and Kabat E A et al. Sequences of Proteins of Immunological Interest. Bethesda, US Department of Health and Human Services, NIH. 1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083).

In one embodiment, a binding molecule of the invention comprises a connecting peptide. The connecting peptides of the invention are synthetic. As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

Connecting peptides of the invention connect two domains (e.g., a binding domain and a dimerization domain) of a binding molecule of the invention. For example, connecting peptides connect a heavy chain portion to a binding domain comprising a binding site. In one embodiment, a connecting peptide connects two heavy chain constant region domains, such as CH1 and CH2 domains; CH1 and CH3 domains; hinge and CH1 domains; hinge and CH3 domains; VH and hinge domains, or a CH3 domain and a non-immunoglobulin polypeptide) in a linear amino acid sequence of a polypeptide chain. Preferably, such connecting peptides provide flexibility to the polypeptide molecule and facilitate dimerization via disulfide bonding. In one embodiment, the connecting peptides of the invention are used to replace one or more heavy chain domains (e.g., at least a portion of a constant region domain (e.g., at least a portion of a CH2 domain) and/or at least a portion of the hinge region (e.g., at least a portion of the lower hinge region domain) in a domain deleted construct). For example, in one embodiment, a VH domain is fused to a CH3 domain via a connecting peptide (the C-terminus of the connecting peptide is attached to the N-terminus of the CH3 domain and the N-terminus of the connecting peptide is attached to the C-terminus of the VH domain). In another embodiment, a VL domain is fused to a CH3 domain via a connecting peptide (the C-terminus of the connecting peptide is attached to the N-terminus of the CH3 domain and the N-terminus of the connecting peptide is attached to the C-terminus of the VL domain. In another embodiment, a CH1 domain is fused to a CH3 domain via a connecting peptide (the C-terminus of the connecting peptide is attached to the N-terminus of the CH3 domain and the N-terminus of the connecting peptide is attached to the C-terminus of the CH1 domain).

In one embodiment, a synthetic connecting peptide comprises a portion of a constant region domain. For example, in one embodiment, a connecting peptide that replaces a CH2 domain can comprise a portion of the CH2 domain.

In one embodiment, a connecting peptide comprises or consists of a gly-ser linker. As used herein, the term "gly-ser linker" refers to a peptide that consists of glycine and serine residues An exemplary gly/ser linker comprises the amino acid sequence GGGSSGGGSG (SEQ ID NO:1). In one embodiment, a connecting peptide of the invention comprises at least a portion of an upper hinge region (e.g., derived from an IgG1, IgG3, or IgG4 molecule), at least a portion of a middle hinge region (e.g., derived from an IgG1, IgG3, or IgG4 molecule) and a series of gly/ser amino acid residues (e.g., a gly/ser linker such as GGGSSGGGSG (SEQ ID NO:1)). In one embodiment, the connecting peptide comprises a substitution of one or more amino acids as compared to naturally occurring IgG1 or IgG3 hinge regions. In another embodiment, a connecting peptide comprises an amino acid sequence such as described in WO 02/060955. Connecting peptides are described in more detail below.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

It is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In one embodiment, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate compliment binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. More generally, those skilled in the art will realize that antibodies modified as described herein may exert a number of subtle effects that may or may not be readily appreciated. However the resulting physiological profile, bioavailability and other biochemical effects of the modifications, such as tumor localization, biodistribution and serum half-life, may easily be measured and quantified using well know immunological techniques without undue experimentation.

In one embodiment, modified forms of antibodies can be made from a whole precursor or parent antibody using techniques known in the art. Exemplary techniques are discussed in more detail below. In particularly preferred embodiments both the variable and constant regions of polypeptides of the invention are human. In one embodiment, fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make antibodies are described in U.S. Pat. Nos. 6,150,584; 6,458,592; 6,420,140. Other techniques are known in the art.

A polypeptide comprising a heavy chain portion may or may not comprise other amino acid sequences or moieties not derived from an immunoglobulin molecule. Such modifications are described in more detail below. For example, in one embodiment, a polypeptide of the invention may comprise a flexible linker sequence. In another embodiment, a polypeptide may be modified to add a functional moiety such as PEG.

The polypeptides of the instant invention comprise at least two binding sites that provide for the association of the polypeptide with the selected target molecule.

In one embodiment, a binding molecule of the invention comprises an antibody molecule, e.g., an intact antibody molecule, or a fragment of an antibody molecule. In another embodiment, binding molecule of the invention is a modified or synthetic antibody molecule. In one embodiment, a binding molecule of the invention comprises all or a portion of (e.g., at least one antigen binding site from, at least one CDR from, or at least one heavy chain portion from) a monoclonal antibody, a humanized antibody, a chimeric antibody, or a recombinantly produced antibody.

In embodiments where the binding molecule is an antibody or modified antibody, the antigen binding site and the heavy chain portions need not be derived from the same immunoglobulin molecule. In this regard, the variable region may or be derived from any type of animal that can be induced to mount a humoral response and generate immunoglobulins against the desired antigen. As such, the variable region of the polypeptides may be, for example, of mammalian origin e.g., may be human, murine, non-human primate (such as cynomolgus monkeys, macaques, etc.), lupine, camelid (e.g., from camels, llamas and related species). In another embodiment, the variable region may be condricthoid in origin (e.g., from sharks).

Polypeptides of the invention can be made using techniques that are known in the art. In one embodiment, the polypeptides of the invention are antibody molecules that have been "recombinantly produced," i.e., are produced using recombinant DNA technology. Exemplary techniques for making antibody molecules are discussed in more detail below.

In one embodiment, the polypeptides of the invention are modified antibodies. As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a binding molecule of the invention is a fusion protein comprising at least one heavy chain portion lacking a CH2 domain and comprising a binding domain of a polypeptide comprising the binding portion of one member of a receptor ligand pair.

In one embodiment, the term, "modified antibody" according to the present invention includes immunoglobulins, antibodies, or immunoreactive fragments or recombinants thereof, in which at least a fraction of one or more of the constant region domains has been deleted or otherwise altered so as to provide desired biochemical characteristics such as the ability to non-covalently dimerize, increased ability to localize at the site of a tumor, or reduced serum half-life when compared with a whole, unaltered antibody of approximately the same immunogenicity. In a preferred embodiment, the polypeptides of the present invention are domain deleted antibodies which comprise a polypeptide chain similar to an immunoglobulin heavy chain, but which lack at least a portion of one or more heavy chain domains. More preferably, one entire domain of the constant region of the modified antibody will be deleted and even more preferably all or part of the CH2 domain will be deleted.

In preferred embodiments, a polypeptide of the invention will not elicit a deleterious immune response in a human. Modifications to the constant region compatible with the instant invention comprise additions, deletions or substitutions of one or more amino acids in one or more domains. That is, the polypeptides of the invention disclosed herein may comprise alterations or modifications to one or more of the three heavy chain constant domains (CH1, CH2 or CH3) and/or to the light chain constant region domain (CL).

For example, in one embodiment, the invention pertains to a humanized form of CC49 (huCC49 version 2 (V2)) having certain amino acid differences as compared to previously known humanized forms of CC49. FIGS. 19A and B show respective alignments of the light and heavy chain variable regions of murine CC49, the human antibodies LEN or 21/28' CL, humanized CC49, and humanized CC49 V2 (which comprises one amino acid substitution in the light chain and two amino acid substitutions in the heavy chain as compared to humanized CC49, see underlined amino acids at position 43 of the light chain and positions 69 and 93 of the heavy chain, Kabat numbering system).

In one embodiment, the invention pertains to a humanized form of CC49 comprising a novel connecting peptide of the invention. For example, FIG. 13A (SEQ ID NO: 24) shows the DNA sequence of heavy chain CH2 domain-deleted huCC49 V2 containing G1/G3/Pro243Ala244Pro245-+[Gly/Ser] hinge connecting peptide. FIG. 13B (SEQ ID NO: 25) shows the DNA sequence of light chain CH2 domain-deleted huCC49 V2. FIG. 14A (SEQ ID NO: 26) shows the amino acid sequence of heavy chain CH2 domain-deleted huCC49 V2 containing G1/G3/Pro243Ala244Pro245+[Gly/Ser] hinge connecting peptide. FIG. 14B (SEQ ID NO: 27) shows the amino acid sequence of light chain CH2 domain-deleted huCC49 V2.

In one embodiment, the polypeptides of the invention may be modified to reduce their immunogenicity using art-recognized techniques. For example, antibodies or polypeptides of the invention can be humanized, deimmunized, or chimeric antibodies can be made. These types of antibodies are derived from a non-human antibody, typically a murine antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81: 6851-5 (1984); Morrison et al., *Adv. Immunol.* 44: 65-92 (1988); Verhoeyen et al., *Science* 239: 1534-1536 (1988); Padlan, *Molec. Immun.* 28: 489-498 (1991); Padlan, *Molec. Immun.* 31: 169-217 (1994), and U.S. Pat. Nos. 5,585,089, 5,693,761 and 5,693,762 all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of polypeptides of the invention that are tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified. In one embodiment, the binding molecule comprises a chimeric antibody. In the context of the present application the term "chimeric antibodies" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse) and the constant region is human. Preferably, the variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

As used herein the term "properly folded polypeptide" includes polypeptides (e.g., antigen binding molecules such as antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein, the term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

In one embodiment, a binding molecule of the invention binds to a tumor cell. Exemplary antibodies which comprise antigen binding sites that bind to antigens expressed on tumor cells are known in the art and one or more CDRs from such antibodies can be included in a binding molecule of the invention. Exemplary antibodies include: 2B8, Lym 1, Lym 2, LL2, Her2, B1, MB1, BH3, B4, B72.3, 5E8, B3F6 and 5E10. In a preferred embodiment, a polypeptide of the invention is a C2B8 antibody which binds to CD20. In another preferred embodiment, a polypeptide of the invention is a CC49 antibody which recognizes TAG72.

In one embodiment, a binding molecule of the invention binds to a molecule which is useful in treating an autoimmune or inflammatory disease or disorder.

As used herein, the term "autoimmune disease or disorder" refers to disorders or conditions in a subject wherein the immune system attacks the body's own cells, causing tissue destruction. Autoimmune diseases include general autoimmune diseases, i.e., in which the autoimmune reaction takes place simultaneously in a number of tissues, or organ specific autoimmune diseases, i.e., in which the autoimmune reaction targets a single organ. Examples of autoimmune diseases that can be diagnosed, prevented or treated by the methods and compositions of the present invention include, but are not limited to, Crohn's disease; Inflammatory bowel disease (IBD); systemic lupus erythematosus; ulcerative colitis; rheumatoid arthritis; goodpasture's syndrome; Grave's disease; Hashimoto's thyroiditis; pemphigus vulgaris; myasthenia gravis; scleroderma; autoimmune hemolytic anemia; autoimmune thrombocytopenic purpura; polymyositis and dermatomyositis; pernicious anemia; Sjögren's syndrome; ankylosing spondylitis; vasculitis; type I diabetes mellitus; neurological disorders, multiple sclerosis, and secondary diseases caused as a result of autoimmune diseases.

As used herein the term "inflammatory disease or disorder" includes diseases or disorders which are caused, at least in part, or exacerbated by inflammation, e.g., increased blood flow, edema, activation of immune cells (e.g., proliferation, cytokine production, or enhanced phagocytosis). Exemplary disorders include those in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, mitochondria, apoptosis, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories.

Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, osteoarthritis, rheumatoid arthritis, acute and chronic infections (bacterial, viral and fungal); acute and chronic bronchitis, sinusitis, and other respiratory infections, including the common cold; acute and chronic gastroenteritis and colitis; acute and chronic cystitis and urethritis; acute respiratory distress syndrome; cystic fibrosis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; and burns (thermal, chemical, and electrical).

As used herein the term "medium that separates polypeptides based on hydrophobic interaction" includes a medium comprising hydrophobic ligands (e.g., alkyl or aryl groups) covalently attached to a matrix. Such a medium can be used to separate polypeptides based on interaction between a solvent and accessible non-polar groups on the surface of the polypeptides and the hydrophobic ligands of the medium. An exemplary medium is Phenyl 5PW-HR available from Tosoh Bioscience.

As used herein, the term "conductivity" includes electrical conductivity of a solution as measured in microSiemens/cm (formerly micromhos/cm). The greater the ion content of a solution, the greater the conductivity of the solution. Conductivity can be readily measured using techniques that are well known in the art (e.g., by measuring the current passing between two electrodes).

The separation methods of the invention can be used with solutions having a pH ranging from acid to neutral, e.g., from about pH 3.5 to approximately neutral. As used herein, the term "approximately neutral pH" includes pH values of approximately 7. For example, in one embodiment, a separation method of the invention can be performed using a solution (e.g., a buffer) having a pH of about 3, about 4, about 5, about 6, about 7, or about 8. Preferably, the pH of the solution is about 6 or about 7. In one embodiment, the pH of the solution is about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0.

As used herein the term "affinity matrix" includes a matrix, such as agarose, controlled pore glass, or poly(styrenedivinyl)benzene to which an affinity ligand is attached. The affinity ligand binds to the desired polypeptide and the contaminating polypeptides are not bound to the affinity ligand. The desired polypeptide can be eluted from the affinity matrix using known protocols.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the binding molecules of the invention are engineered, e.g., to express a connecting peptide of the invention.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

As used herein, the phrase "subject that would benefit from administration of a binding molecule" includes subjects, such as mammalian subjects, that would benefit from administration of a binding molecule used, e.g., for detection of an antigen recognized by a binding molecule (e.g., for a diagnostic procedure) and/or from treatment with a binding molecule to reduce or eliminate the target recognized by the binding molecule. For example, in one embodiment, the subject may benefit from reduction or elimination of a soluble or particulate molecule from the circulation or serum (e.g., a toxin or pathogen) or from reduction or elimination of a population of cells expressing the target (e.g., tumor cells). As described in more detail herein, the binding molecule can be used in unconjugated form or can be conjugated, e.g., to a drug, prodrug, or an isotope.

II. SYNTHETIC CONNECTING PEPTIDES

At least one polypeptide chain of a dimer of the invention can comprise a synthetic connecting peptide of the invention. In one embodiment, at least two chains of a dimer of the invention comprise a connecting peptide. In a preferred embodiment, two chains of a dimer of the invention comprise a connecting peptide.

In one embodiment, connecting peptides can be used to join two heavy chain portions in frame in a single polypeptide chain. For example, in one embodiment, a connecting peptide of the invention can be used to fuse a CH3 domain (or synthetic CH3 domain) to a hinge region (or synthetic hinge region). In another embodiment, a connecting peptide of the invention can be used to fuse a CH3 domain (or synthetic CH3 domain) to a CH1 domain (or synthetic CH1 domain). In still another embodiment, a connecting peptide can act as a peptide spacer between the hinge region (or synthetic hinge region) and a CH2 domain (or a synthetic CH2 domain).

In another embodiment, a CH3 domain can be fused to an extracellular protein domain (e.g., a VL domain (or synthetic domain), a VH domain (or synthetic domain), a CH1 domain (or synthetic domain), a hinge domain (or synthetic hinge), or to the ligand binding portion of a receptor or the receptor binding portion of a ligand). For example, in one embodiment, a VH or VL domain is fused to a CH3 domain via a connecting peptide (the C-terminus of the connecting peptide is attached to the N-terminus of the CH3 domain and the N-terminus of the connecting peptide is attached to the C-terminus of the VH or VL domain). In another embodiment, a CH1 domain is fused to a CH3 domain via a connecting peptide (the C-terminus of the connecting peptide is attached to the N-terminus of the CH3 domain and the N-terminus of the connecting peptide is attached to the C-terminus of the CH1 domain). In another embodiment, a connecting peptide of the invention can be used to fuse a CH3 domain (or synthetic CH3 domain) to a hinge region (or synthetic hinge region) or portion thereof. In still another embodiment, a connecting peptide can act as a peptide spacer between the hinge region (or synthetic hinge region) and a CH2 domain (or a synthetic CH2 domain).

In one embodiment, a connecting peptide can comprise or consist of a gly/ser spacer. For example, a domain deleted CC49 construct having a short amino acid spacer GGSSGGGGSG (SEQ. ID No. 1) substituted for the CH2 domain and the lower hinge region (CC49.ΔCH2 [gly/ser]) can be used. In another embodiment, a connecting peptide comprises the amino acid sequence IGKTISKKAK (SEQ ID NO:36).

In another embodiment, connecting peptide can comprise at least a portion of an immunoglobulin hinge region. For example, chimeric hinge domains can be constructed which combine hinge elements derived from different antibody isotypes. In one embodiment, a connecting peptide comprises at least a portion of an IgG1 hinge region. In another embodiment, a connecting peptide can comprise at least a portion of an IgG3 hinge region. In another embodiment, a connecting peptide can comprise at least a portion of an IgG1 hinge region and at least a portion of an IgG3 hinge region. In one embodiment, a connecting peptide can comprise an IgG1 upper and middle hinge and a single IgG3 middle hinge repeat motif.

Because the numbering of individual amino acids in such connecting peptides comprising an amino acid sequence derived from an immunoglobulin hinge region may vary depending upon the length of the connecting peptide, the numbering of amino acid positions in these molecules is given using Kabat numbering see, e.g., Table 2). Table 1 shows naturally occurring hinge sequence for IgG1, IgG3, and IgG4 molecules. Table 2 shows Kabat numbering for portions of these hinge molecules and also shows Kabat numbering for connecting peptide amino acid residues presented in that table.

In one embodiment, a connecting peptide of the invention comprises a non-naturally occurring immunoglobulin hinge region domain, e.g., a hinge region domain that is not naturally found in the polypeptide comprising the hinge region domain and/or a hinge region domain that has been altered so that it differs in amino acid sequence from a naturally occurring immunoglobulin hinge region domain. In one embodiment, mutations can be made to hinge region domains to make a connecting peptide of the invention. In one embodiment, a connecting peptide of the invention comprises a hinge domain which does not comprise a naturally occurring number of cysteines, i.e., the connecting peptide comprises either fewer cysteines or a greater number of cysteines than a naturally occurring hinge molecule. In a preferred embodiment, incorporation of the connecting peptide into a polypeptide results in a composition in which greater than 50%, 60%, 70%, 80% or 90% of the dimeric molecules present in a form in which the two heavy chain portions are linked via at least one interchain disulfide linkage.

In one embodiment of the invention, a connecting peptide comprises hinge region domain comprising a proline residue at an amino acid position corresponding to amino acid position 243 in the Kabat numbering system (position 230, EU numbering system). In one embodiment, a connecting peptide comprises an alanine residue at an amino acid position corresponding to position 244, Kabat numbering system (position 246, EU numbering system). In another embodiment, a connecting peptide of the invention comprises a proline residue at an amino acid position corresponding to position 245 (Kabat numbering system; position 247, EU numbering system)). In one embodiment, a connecting peptide comprises a cysteine residue at an amino acid position corresponding to position 239, Kabat numbering system (position 226, EU numbering system). In one embodiment, a connecting peptide comprises a serine residue at an amino acid position corresponding to position 239, Kabat numbering system (position 226, EU numbering system). In one embodiment, a connecting peptide comprises a cysteine residue at an amino acid position corresponding to position 242, Kabat numbering system (position 229, EU numbering system). In one embodiment, a connecting peptide comprises a serine residue at an amino acid position corresponding to position 242, Kabat numbering system (position 229, EU numbering system).

In one embodiment, the connecting peptide can be chosen to result in the preferential synthesis of a particular isoform of polypeptide, e.g., in which the two heavy chain portions are linked via disulfide bonds or are not linked via disulfide bonds. For example, as described in the instant examples, the G1/G3/Pro243+[gly/ser] linker (SEQ ID NO: 8), G1/G3/Pro243Ala244Pro245+[gly/ser] linker (SEQ ID NO: 9), Pro243+[gly/ser] linker (SEQ ID NO:15), and Pro243Ala244Pro245+[gly/ser] linker (SEQ ID NO: 14), connecting peptides resulted in the production of only Form A CH2 domain-deleted antibody with no detectable Form B. In contrast, CH2 domain-deleted Cys242Ser:Pro243 (SEQ ID NO: 12), and CH2 domain-deleted Cys242Ser:Pro243Ala244Pro245 (SEQ ID NO: 13), both resulted in a preference for the Form B form. These synthetic hinge region connecting peptides would thus be useful for favoring synthesis of Form A or B form. This is true for any isotype of antibody, (e.g., IgG1, IgG2, IgG3, or IgG4) based on the high degree of homology among the CH3 domains for all four human isotypes. (Including identical and conserved amino acid residues, IgG1 CH3 domain is 98.13% homologous to IgG2 CH3, 97.20% homologous to IgG3 CH3, and 96.26% homologous to IgG4 CH3). The parentheticals referring to connecting peptides and various binding molecules of the invention represent equivalent terminology unless otherwise indicated.

In one embodiment, a connecting peptide of the invention comprises a hinge region domain followed by a flexible gly/ser linker. Exemplary connecting peptides are shown in Table 2 and in SEQ ID NOs: 8-15, 37 and 53. It will be understood that variant forms of these exemplary connecting peptides can be created by introducing one or more nucleotide substitutions, additions or deletions into the nucleotide sequence encoding a connecting peptide such that one or more amino acid substitutions, additions or deletions are introduced into the connecting peptide. For example, mutations may be introduced by standard techniques, such as site-directed mutagenesis and PCR-mediated mutagenesis. Preferably, conservative amino acid substitutions are made at one or more nonessential amino acid residues such that the ability of the connecting peptide to preferentially enhance synthesis of Form A or Form B is not altered. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Connecting peptides of the invention can be of varying lengths. In one embodiment, a connecting peptide of the invention is from about 15 to about 50 amino acids in length. In another embodiment, a connecting peptide of the invention is from about 20 to about 45 amino acids in length. In another embodiment, a connecting peptide of the invention is from about 25 to about 40 amino acids in length. In another embodiment, a connecting peptide of the invention is from about 30 to about 35 amino acids in length. In another embodiment, a connecting peptide of the invention is from about 24 to about 27 amino acids in length. In another embodiment, a connecting peptide of the invention is from about 40 to about 42 amino acids in length.

Connecting peptides can be introduced into polypeptide sequences using techniques known in the art. For example, in one embodiment, the Splicing by Overlap Extension (SOE)

method (Horton, R. M. 1993 Methods in Molecular Biology, Vol 15: PCR Protocols: Current Methods and applications. Ed. B. A. White) can be used. Modifications can be confirmed by DNA sequence analysis. Plasmid DNA can be used to transform host cells for stable production of the polypeptides produced.

In one embodiment, incorporation of one of the subject connecting peptides into a polypeptide yields a composition comprising polypeptide molecules having at least two binding sites and at least two polypeptide chains, wherein at least two of the polypeptide chains comprise a synthetic connecting peptide and wherein greater than 50% of the molecules are present in a form in which the two heavy chain portions are linked via at least one interchain disulfide linkage. In another embodiment, greater than 60% of the molecules are present in a form in which the two heavy chain portions are linked via at least one interchain disulfide linkage. In another embodiment, greater than 70% of the molecules are present in a form in which the two heavy chain portions are linked via at least one interchain disulfide linkage. In another embodiment, greater than 80% of the molecules are present in a form in which the two heavy chain portions are linked via at least one interchain disulfide linkage. In another embodiment, greater than 90% of the molecules are present in a form in which the two heavy chain portions are linked via at least one interchain disulfide linkage.

III. BINDING MOLECULES

A. Antibodies or Portions Thereof

In one embodiment, a binding molecule of the invention is an antibody molecule. Using art recognized protocols, for example, antibodies are preferably raised in mammals by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature*, 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, DNA encoding a desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments (e.g., antigen binding sites) may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. *Immunol. Today* 21:371; Nagy et al. 2002. *Nat. Med.* 8:801; Huie et al. 2001. *Proc. Natl. Acad. Sci. USA* 98:2682; Lui et al. 2002. *J. Mol. Biol.* 315:1063, each of which is incorporated herein by reference. Several publications (e.g., Marks et al. *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. *Nat. Biotechnol.* 18:1287; Wilson et al. 2001. *Proc. Natl. Acad. Sci. USA* 98:3750; or Irving et al. 2001 *J. Immunol. Methods* 248:31. In yet another embodiment, cell surface libraries can be screened for antibodies (Boder et al. 2000. Proc. Natl. Acad. Sci. USA 97:10701; Daugherty et al. 2000 *J. Immunol. Methods* 243:211. Such procedures provide alternatives to traditional hybridoma techniques for the isolation and subsequent cloning of monoclonal antibodies.

Yet other embodiments of the present invention comprise the generation of human or substantially human antibodies in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the polypeptides of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or synthetic to provide obtain polypeptides of the present invention.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

B. Modified Antibodies

In one embodiment, a binding molecule or antigen binding molecule of the invention comprise synthetic constant regions wherein one or more domains are partially or entirely deleted ("domain-deleted antibodies"). In especially preferred embodiments compatible modified antibodies will comprise domain deleted constructs or variants wherein the entire CH2 domain has been removed (ΔCH2 constructs). For other preferred embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody.

In one embodiment, the modified antibodies of the invention are minibodies. Minibodies can be made using methods described in the art (see, e.g., see e.g., U.S. Pat. No. 5,837,821 or WO 94/09817A1).

In another embodiment, the modified antibodies of the invention are CH2 domain deleted antibodies which are known in the art. Domain deleted constructs can be derived using a vector (e.g., from IDEC Pharmaceuticals, San Diego) encoding an $IgG_1$ human constant domain (see, e.g., WO 02/060955A2 and WO02/096948A2). This exemplary vector was engineered to delete the CH2 domain and provide a synthetic vector expressing a domain deleted $IgG_1$ constant region. Genes encoding the murine variable region of the C2B8 antibody, 5E8 antibody, B3F6 antibody, or the variable region of the humanized CC49 antibody were then inserted in the synthetic vector and cloned. When expressed in transformed cells, these vectors provided C2B8.ΔCH2, 5E8.ΔCH2, B3F6.ΔCH2 or huCC49.ΔCH2 or respectively.

These constructs exhibit a number of properties that make them particularly attractive candidates for monomeric subunits.

It will be noted that these exemplary constructs were engineered to fuse the CH3 domain directly to a hinge region of the respective polypeptides of the invention. In other constructs it may be desirable to provide a peptide spacer between the hinge region and the synthetic CH2 and/or CH3 domains. For example, compatible constructs could be expressed wherein the CH2 domain has been deleted and the remaining CH3 domain (synthetic or unsynthetic) is joined to the hinge region with a 5-20 amino acid spacer. Such a spacer may be added, for instance, to ensure that the regulatory elements of the constant domain remain free and accessible or that the hinge region remains flexible. For example, a domain deleted CC49 construct having a short amino acid spacer GGSSGGGGSG (SEQ. ID No. 1) substituted for the CH2 domain and the lower hinge region (CC49.ΔCH2 [gly/ser]) can be used. Other exemplary connecting peptides are shown in Table 2. These connecting peptides can be used with any of the polypeptides of the invention. Preferably, the connecting peptides are used with a polypeptide lacking a CH2 heavy chain domain. Preferably, any linker compatible with the instant invention will be relatively non-immunogenic and not inhibit the non-covalent association of the polypeptides of the invention.

In one embodiment, a polypeptide of the invention comprises an immunoglobulin heavy chain having deletion or substitution of a few or even a single amino acid as long as it permits the desired covalent or non-covalent association between the monomeric subunits. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other preferred embodiments may comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

C. Fusion Proteins

The invention also pertains to binding molecules which comprise one or more immunoglobulin domains. The fusion proteins of the invention comprise a binding domain (which comprises at least one binding site) and a dimerization domain (which comprises at least one heavy chain portion). The subject fusion proteins may be bispecific (with one binding site for a first target and a second binding site for a second target) or may be multivalent (with two binding sites for the same target).

Exemplary fusion proteins reported in the literature include fusions of the T cell receptor (Gascoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin (homing receptor) (Watson et al., J. Cell. Biol. 110:2221-2229 (1990); and Watson et al., Nature 349: 164-167 (1991)); CD44 (Aruffo et al., Cell 61:1303-1313 (1990)); CD28 and B7 (Linsley et al., J. Exp. Med. 173:721-730 (1991)); CTLA-4 (Lisley et al., J. Exp. Med. 174:561-569 (1991)); CD22 (Stamenkovic et al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); and IgE receptor a (Ridgway and Gorman, J. Cell. Biol. Vol. 115, Abstract No. 1448 (1991)).

In one embodiment a fusion protein combines the binding domain(s) of the ligand or receptor (e.g. the extracellular domain (ECD) of a receptor) with at least one heavy chain domain and a synthetic connecting peptide. In one embodiment, when preparing the fusion proteins of the present invention, nucleic acid encoding the binding domain of the ligand or receptor domain will be fused C-terminally to nucleic acid encoding the N-terminus of an immunoglobulin constant domain sequence. N-terminal fusions are also possible. In one embodiment, a fusion protein includes a CH2 and a CH3 domains. Fusions may also be made to the C-terminus of the Fc portion of a constant domain, or immediately N-terminal to the CH1 of the heavy chain or the corresponding region of the light chain.

In one embodiment, the sequence of the ligand or receptor binding domain is fused to the N-terminus of the Fc domain of an immunoglobulin molecule. It is also possible to fuse the entire heavy chain constant region to the ligand or receptor binding domain sequence. In one embodiment, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. The precise site at which the fusion is made is not critical; particular sites are well known and may be selected in order to optimize the biological activity, secretion, or binding characteristics of the molecule. Methods for making fusion proteins are known in the art.

For bispecific fusion proteins, the fusion proteins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Additional exemplary ligands and their receptors that may be included in the subject fusion proteins include the following:

Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, and interferons such as interferon-α, β, or γ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IFNγ (EP0240975), and the TNF family of receptors (e.g., TNFα (e.g. TNFR-1 (EP 417, 563), TNFR-2 (EP 417,014) lymphotoxin beta receptor).

Adhesion Proteins

Adhesion molecules are membrane-bound proteins that allow cells to interact with one another. Various adhesion proteins, including leukocyte homing receptors and cellular adhesion molecules, of receptor binding portions thereof, can be incorporated in a fusion protein of the invention. Leucocyte homing receptors are expressed on leucocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules. (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

Chemokines

Chemokines, chemotactic proteins which stimulate the migration of leucocytes towards a site of infection, can also be incorporated into a fusion protein of the invention. Exemplary chemokines include Macrophage inflammatory proteins (MIP-1-α and MIP-1-β), neutrophil chemotactic factor, and RANTES (regulated on activation normally T-cell expressed and secreted).

Growth Factors and Growth Factor Receptors

Growth factors or their receptors (or receptor binding or ligand binding portions thereof) may be incorporated in the fusion proteins of the invention. Exemplary growth factors include Vascular Endothelial Growth Factor (VEGF) and its isoforms (U.S. Pat. No. 5,194,596); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); stem-cell factor (SCF), thrombopoietin (c-Mpl ligand), and the Wnt polypeptides (U.S. Pat. No. 6,159,462).

e) Hormones

Exemplary growth hormones for use as targeting agents in the fusion proteins of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH), calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

Clotting Factors

Exemplary blood coagulation factors for use as targeting agents in the fusion proteins of the invention include the clotting factors (e.g., factors V, VII, VIII, X, IX, XI, XII and XIII, von Willebrand factor); tissue factor (U.S. Pat. Nos. 5,346,991, 5,349,991, 5,726,147, and 6,596,845); thrombin and prothrombin; fibrin and fibrinogen; plasmin and plasminogen; plasminogen activators, such as urokinase or human urine or tissue-type plasminogen activator (t-PA).

Other exemplary fusion proteins are taught, e.g., in WO0069913A1 and WO0040615A2. Another exemplary molecule that may be included in a fusion protein of the invention is IGSF9.

Fusion proteins can be prepared using methods that are well known in the art (see for example U.S. Pat. Nos. 5,116,964 and 5,225,538). Ordinarily, the ligand or ligand binding partner is fused C-terminally to the N-terminus of the constant region of the heavy chain (or heavy chain portion) and in place of the variable region. Any transmembrane regions or lipid or phospholipids anchor recognition sequences of ligand binding receptor are preferably inactivated or deleted prior to fusion. DNA encoding the ligand or ligand binding partner is cleaved by a restriction enzyme at or proximal to the 5' and 3'ends of the DNA encoding the desired ORF segment. The resultant DNA fragment is then readily inserted into DNA encoding a heavy chain constant region. The precise site at which the fusion is made may be selected empirically to optimize the secretion or binding characteristics of the soluble fusion protein. DNA encoding the fusion protein is then transfected into a host cell for expression.

In one embodiment, a nucleic acid molecule of the invention comprises a nucleotide sequence shown in FIG. 4A (SEQ ID NO 16). In another embodiment, a nucleic acid molecule of the invention comprises a nucleotide sequence shown in FIG. 4B (SEQ ID NO:17). In one embodiment, a polypeptide molecule of the invention comprises a polypeptide sequence encoded by a nucleic acid molecule comprising a nucleic acid sequence shown in FIG. 4A (SEQ ID NO: 16). In another embodiment, a polypeptide molecule of the invention comprises a polypeptide sequence encoded by a nucleic acid molecule having a nucleotide sequence shown in FIG. 4B (SEQ ID NO: 17).

In one embodiment, a polypeptide molecule of the invention comprises an amino acid sequence shown in FIG. 8A (SEQ ID NO: 18). In another embodiment, a polypeptide molecule of the invention comprises an amino acid sequence shown in FIG. 8B (SEQ ID NO: 19).

In another embodiment, a polypeptide of the invention comprises an amino acid sequence encoded by a nucleotide sequence shown in FIG. 9 (SEQ ID NO:20). In another embodiment, a nucleic acid molecule of the invention comprises a nucleotide sequence shown in FIG. 9 (SEQ ID NO:20).

In another embodiment, a polypeptide of the invention comprises an amino acid sequence encoded by a nucleotide sequence shown in FIG. 10 (SEQ ID NO: 21). In another embodiment, a nucleic acid molecule of the invention comprises a nucleotide sequence shown in FIG. 10 (SEQ ID NO: 21).

In another embodiment, a polypeptide of the invention comprises an amino acid sequence encoded by a nucleotide sequence shown in FIG. 28A (SEQ ID NO: 38). In another embodiment, a nucleic acid molecule of the invention comprises a nucleotide sequence shown in FIG. 28A (SEQ ID NO: 38).

In another embodiment, a polypeptide of the invention comprises an amino acid sequence encoded by a nucleotide sequence shown in FIG. 28B (SEQ ID NO: 39). In one embodiment, a nucleic acid molecule of the invention comprises a nucleotide sequence shown in FIG. 28B (SEQ ID NO: 39).

In another embodiment, a polypeptide of the invention comprises an amino acid sequence shown in FIG. 11 (SEQ ID NO: 22).

In another embodiment, a polypeptide of the invention comprises an amino acid sequence shown in FIG. 12 (SEQ ID NO: 23).

In another embodiment, a polypeptide of the invention comprises an amino acid sequence shown in FIG. 29A (SEQ ID NO: 40). In another embodiment, a polypeptide of the invention comprises an amino acid sequence shown in FIG. 29B (SEQ ID NO: 41).

In another embodiment, a polypeptide of the invention comprises an amino acid sequence encoded by a nucleotide sequence shown in FIG. 32A (SEQ ID NO: 42). In another embodiment, a nucleic acid molecule of the invention comprises a nucleotide sequence shown in FIG. 32A (SEQ ID NO: 42). In another embodiment, a polypeptide of the invention comprises an amino acid sequence encoded by a nucleotide sequence shown in FIG. 32B (SEQ ID NO: 43). In one embodiment, a nucleic acid molecule of the invention comprises a nucleotide sequence shown in FIG. 32B (SEQ ID NO: 43).

In another embodiment, a polypeptide of the invention comprises an amino acid sequence encoded by a nucleotide sequence shown in FIG. 13A (SEQ ID NO: 24). In one embodiment, a nucleic acid molecule of the invention comprises a nucleotide sequence shown in FIG. 13A (SEQ ID NO: 24). In another embodiment, a polypeptide of the invention comprises an amino acid sequence encoded by a nucleotide sequence shown in FIG. 13B (SEQ ID NO: 25). In one embodiment, a nucleic acid molecule of the invention comprises a nucleotide sequence shown in FIG. 13B (SEQ ID NO: 25).

In another embodiment, a polypeptide of the invention comprises an amino acid sequence shown in FIG. 14A (SEQ ID NO: 26). In another embodiment, a polypeptide of the invention comprises an amino acid sequence shown in FIG. 14B (SEQ ID NO: 27).

In another embodiment, a polypeptide of the invention comprises an amino acid sequence shown in FIG. 33A (SEQ ID NO: 44). In another embodiment, a polypeptide of the invention comprises an amino acid sequence shown in FIG. 33B (SEQ ID NO: 45).

In another embodiment, a nucleic acid molecule of the invention comprises a nucleotide sequence shown in FIG. 25A (SEQ ID NO: 46). In another embodiment, a polypeptide of the invention comprises an amino acid sequence shown in FIG. 25B (SEQ ID NO: 47).

In another embodiment, a nucleic acid molecule of the invention comprises a nucleotide sequence shown in FIG. 26A (SEQ ID NO: 48). In another embodiment, a polypeptide of the invention comprises an amino acid sequence shown in FIG. 26B (SEQ ID NO: 49).

In another embodiment, a polypeptide of the invention comprises an amino acid sequence shown in FIG. 12 (SEQ ID NO: 31).

In another embodiment, a polypeptide of the invention comprises an amino acid sequence shown in FIG. 12 (SEQ ID NO: 35).

The other nucleic acid and amino acid sequences disclosed herein in the sequence listing and Figures are also embraced by the invention.

D. Expression of Polypeptides

Following manipulation of the isolated genetic material to provide polypeptides of the invention as set forth above, the genes are typically inserted in an expression vector for introduction into host cells that may be used to produce the desired quantity of polypeptide that, in turn, provides the claimed polypeptides.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals. In particularly preferred embodiments the cloned variable region genes are inserted into an expression vector along with the heavy and light chain constant region genes (preferably human) synthetic as discussed above. Preferably, this is effected using a proprietary expression vector of IDEC, Inc., referred to as NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. As seen in the examples below, this vector has been found to result in very high level expression of antibodies upon incorporation of variable and constant region genes, transfection in CHO cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the polypeptides of the invention of the instant invention may be expressed using polycistronic constructs such as those disclosed in copending U.S. provisional application No. 60/331,481 filed Nov. 16, 2001 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a monomeric subunit of the polypeptide (e.g. a modified antibody) has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to any introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding the polypeptide of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules. Where tetravalent forms of antibodies are desired, the subunits will then self-assemble into tetravalent antibodies (WO02/096948A2).

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

IV. SEPARATION OF POLYPEPTIDES COMPRISING AT LEAST ONE INTERCHAIN DISULFIDE Linkage from Those Lacking Interchain Disulfide Linkages In one aspect, the invention pertains to separation of molecules having two heavy chain portions from a mixture, where a fraction of the molecules are present in a form in which the two heavy chain portions are linked via at least one interchain disulfide linkage and a fraction of the molecules comprise heavy chain portions that are not linked via at least one disulfide linkage by hydrophobic interaction chromatography.

Hydrophobic interaction chromatography was first developed following the observation that proteins could be retained on affinity gels which comprised hydrocarbon spacer arms but lacked the affinity ligand. Elution from HIC supports can be effected by alterations in solvent, pH, ionic strength, or by the addition of chaotropic agents or organic modifiers, such as ethylene or propylene glycol. A description of the general principles of hydrophobic interaction chromatography can be found e.g., in U.S. Pat. No. 3,917,527 and in U.S. Pat. No. 4,000,098. HIC in the context of high performance liquid chromatography (HPLC) has been used to separate antibody fragments lacking heavy chain portions (e.g., F(ab')$_2$) from intact antibody molecules in a single step protocol. (Morimoto, K. et al., L Biochem. Biophvs. Meth. 24: 107 (1992)).

The separation method of the invention can be performed on an unpurified population of polypeptides (e.g., culture supernatants or preparations or preparations of polypeptides isolated from prokaryotic inclusion bodies). Alternatively, the instant separation methods can be used on polypeptide mixtures obtained after one or more initial purification steps, e.g., after a preparation comprising forms A and B has been eluted from an affinity matrix.

In one embodiment, the binding molecules subjected to HIC chromatography comprise a connecting peptide of the invention.

In a preferred embodiment, HIC can be applied to mixtures that have been partially purified by other protein purification procedures. The term "partially purified" as used herein includes a protein preparation in which the protein of interest is present in at least 5% by weight, more preferably at least 10% and most preferably at least 45%. Initial or subsequent purification steps can be used to remove, e.g., immunoglobulin aggregates, misfolded species, host cell protein, residue material from preceding chromatographic steps (such as Protein A when employed). In one embodiment, HIC can be performed on polypeptides comprising a connecting peptide of the invention. Accordingly, the application of HIC can also be appreciated in the context of an overall purification protocol. Exemplary purification steps that can be used prior to or subsequent to HIC include: affinity chromatography (for example, PROSEP-A® (BioProcessing Ltd., U.K.) which consists of Protein A covalently coupled to controlled pore glass or Protein A SEPHAROSE® Fast Flow (Pharmacia) or TOYOPEARL 650M Protein A (Toso Haas)). Protein A is preferred for human γ1, γ2, or γ4 heavy chains and protein G for mouse isotypes. Bakerbond ABX™ resin can be used if the molecule comprises a CH3 domain. In addition or alternatively, ion exchange chromatography may be employed. In this regard various anionic or cationic substituents. may be attached to matrices in order to form anionic or cationic supports for chromatography. Anionic exchange substituents include diethylaminoethyl (DEAE), quaternary aminoethyl (QAE) and quaternary amine (Q) groups. Cationic exchange substituents. include carboxymethyl (CM), sulfoethyl (SE), sulfopropyl (SP), phosphate (P) and sulfonate (S). Cellulose ion exchange resins such as DE23, DE32, DE52, CM-23, CM-32 and CM-52 are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow are all available from Pharmacia AB. Further, both DEAE and CM derivitized ethylene glycol-methacrylate copolymer such as TOYOPEARL DEAE-650S or M and TOYOPEARL CM-650S or M are available from Toso Haas Co., Philadelphia, Pa. Because elution from ion exchange supports usually involves addition of salt and because HIC is enhanced under increased salt concentrations, the introduction of a HIC step following an ionic exchange chromatographic step or other salt mediated purification step is preferred. Additional purification protocols may be added including but not necessarily limited to: further ionic exchange chromatography, size exclusion chromatography, viral inactivation, concentration and freeze drying, hydroxylapatite chromatography, gel electrophoresis, dialysis, ethanol precipitation, reverse phase HPLC, chromatography on silica, chromatography on heparin SEQHAROSE™, chromatofocusing, or ammonium sulfate precipitation.

Prior to purification using the subject methods, the composition comprising the mixture of polypeptides to be separated will preferably be placed in a buffer of acidic or approximately neutral pH. This can be done, for example, by adding concentrated buffer, resuspending the sample in the buffer, exchanging the buffer (e.g., using dialysis or ultrafiltration). Alternatively, the pH of the sample buffer can simply be adjusted to be within the desired range.

Hydrophobic interactions are strongest at high ionic strength, therefore, this form of separation is conveniently performed following salt precipitations or ion exchange procedures. Adsorption of the proteins to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++}<; Ca^{++}<; Mg^{++}<; Li^+<; Cs^+<; Na^+<; K^+<; Rb^+<; NH_4^+$, while anions may be ranked in terms of increasing chaotropic effect as $PO^{---}<; SO_4^{--}<; CH_3COOO^-<; Cl^-<; Br^-<; NO_3^-<; ClO_4^-<; I^-<; SCN^-$.

In general, Na, K or $NH_4$ sulfates effectively promote ligand-protein interaction in HIC. Salts may be formulated that influence the strength of the interaction as given by the following relationship: $(NH_4)_2SO_4>; Na_2SO_4>; NaCl>; NH_4Cl>; NaBr>; NaSCN$. In general, salt concentrations of between about 0.75 and about 2M ammonium sulfate or between about 1 and 4M NaCl are useful.

A number of chromatographic supports may be employed in the preparation of HIC columns, the most extensively used are agarose, silica and organic polymer or co-polymer resins. The hydrophobic interaction material is generally a base matrix (e.g., a hydrophilic carbohydrate (such as cross-linked agarose) or synthetic copolymer material) to which hydrophobic ligands (e.g., alkyl or aryl groups) are coupled. The preferred HIC material comprises an agarose resin substituted with phenyl groups. Exemplary HIC material includes: phenyl SEPHAROSE™, FAST FLOW with low or high substitution (Pharmacia LKB Biotechnology, AB, Sweden); phenyl SEPHAROSE™ High Performance column; phenyl or butyl-SEPHAROSE® CL-4B, butyl-SEPHAROSE® FF, octyl-SEPHAROSE® FF and phenyl-SEPHAROSE® FF (Pharmacia LKB Biotechnology AB, Sweden); Fractogel™ EMD Propyl or FRACTOGEL™ EMC Phenyl columns (E. Merck, Germany); MACROPREP™ Methyl or MACROPREP™ t-Butyl Supports (Bio-Rad, California); WP HI-Propyl (C3)™ column (J.T. Baker, New Jersey). Exemplary HIC materials are also available from Tosoh Corporation, Tokyo, Japan under the product names TOYOPEARL ether 650, phenyl 650, butyl 650 (Fractogel), ether-5PW-HR, or phenyl-5PW-HR; Miles-Yeda, Rehovot, Israel under the product name alkyl-agarose, wherein the alkyl group contains from 2-10 carbon atoms, and J.T. Baker, Phillipsburg, N.J. under the product name Bakerbond WP-HI-propyl. It is also possible to prepare the desired HIC column using conventional chemistry. (Sa: for example, Er-el. Z. gl all, Biochem. Biophys. Res. Comm. 49:383 (1972) or Ulbrich, V. rd gL Coll. Czech. Chem. Commum. 9:1466 (1964)).

The choice of a particular gel can be determined by the skilled artisan. In general the strength of the interaction of the protein and the HIC ligand increases with the chain length of the alkyl ligands but ligands having from about 4 to about 8 carbon atoms are suitable for most separations. A phenyl group has about the same hydrophobicity as a pentyl group, although the selectivity can be different owing to the possibility of pi-pi orbital interaction with aromatic groups on the protein. Selectively may also be affected by the chemistry of the supporting resin.

Ligand density is an important parameter in that it influences not only the strength of the interaction but the capacity of the column as well. The ligand density of the commercially available phenyl or octyl phenyl gels is on the order of 40 pmoles/ml gel bed. Gel capacity is a function of the particular protein in question as well as pH, temperature and salt type and concentration but generally can be expected to fall in the range of 3-20 mg/ml of gel.

In general, a decrease in temperature decreases the interaction with HIC material. However, any benefit that would accrue by increasing the temperature must also be weighed against adverse effects such an increase may have on the stability of the protein.

In one embodiment, the polypeptides of the invention can be eluted isocratically. In isocratic elution, all compounds begin migration through the column at onset. However, each migrates at a different rate, resulting in faster or slower elution rate. For example, as described in the instant examples, form A can be eluted with the flow through of the column.

In another embodiment, one or more polypeptides of the invention can be bound to the column and eluted, e.g., using stepwise elution or gradient elution. Elution, whether stepwise or in the form of a gradient, can be accomplished in a variety of ways: (a) by changing the salt concentration, (b) by changing the polarity of the solvent or (c) by adding detergents. By decreasing salt concentration adsorbed proteins are eluted in order of increasing hydrophobicity. Changes in polarity may be affected by additions of solvents such as ethylene or propylene glycol or (iso)propanol, thereby decreasing the strength of the hydrophobic interactions. Detergents function as displacers of proteins and have been used primarily in connection with the purification of membrane proteins.

In performing the separation, the polypeptide mixture can be contacted with the HIC material e.g., using a batch purification technique or using a column. Prior to HIC purification it may be desirable to remove any chaotropic agents or very hydrophobic substances, e.g., by passing the mixture through a precolumn.

For example, for batch purification, HIC material is prepared in or equilibrated to the desired starting buffer. A slurry of the HIC material is obtained. The polypeptide solution is contacted with the slurry to adsorb at least one of the polypeptides to be separated to the HIC material. The solution containing the polypeptides that do not bind to the HIC material is separated from the slurry, e.g., by allowing the slurry to settle and removing the supernatant. The slurry can be subjected to one or more washing steps. If desired, the slurry can be contacted with a solution of lower conductivity to desorb polypeptides that have bound to the HIC material. In order to elute bound polypeptides, the salt concentration can be decreased.

In one embodiment, the HIC material can be packed in a column. A mixture comprising the polypeptides to be separated can be applied to the column allowing at least one of the polypeptides to be separated to adsorb to the column. The polypeptides that do not adsorb to the column pass through and can be collected. In order to elute bound polypeptides, the salt concentration can be decreased, e.g., in a step-wise fashion or using a salt gradient.

Since form B is more hydrophobic than form A, it adsorbs irreversibly to the stationary phase using approximately 0.7 M (e.g., 0.73M) Ammonium Sulfate/20 mM Sodium Phosphate, pH 4.0 to pH 8.0 as the mobile phase. Form A binds to a lesser extent to the stationary phase under these conditions and is therefore eluted isocratically, i.e. it leaves the column with the flowthrough fraction. Subsequent to the isocratic elution of form A, omitting Ammonium sulfate from the mobile phase desorbs form B.

In an exemplary purification scheme, the HIC material is equilibrated in a buffer comprising a salt concentration yielding a conductivity of from between about 160 to about 110, preferably from between about 140 to about 115, even more preferably from between about 130 or about 120 to about 117 mS/cm. For example, an exemplary starting solution comprises a salt concentration of approximately 1M to 0.7M, e.g., 1M to 0.7M ammonium sulfate. In a preferred embodiment, the solution comprising the mixture of polypeptides to be separated is also brought to the same, or approximately the same conductivity (e.g., using a concentrated stock solution of salt). Under these conditions, Form A is eluted from the column at a conductivity of about 120 mS/cm. In order to elute Form B, a stepwise or linear gradient of reducing ammonium sulfate content can be applied to the column. Form B elutes at a conductivity of approximately 115 to approximately 100 mS/cm.

In one embodiment, the subject purification method yields a composition comprising polypeptide molecules having at least two binding sites and two heavy chain portions, wherein the heavy chain portions lack CH2 domains and wherein greater than 50% of the molecules are present in a form in which the two heavy chain portions are linked via at least one interchain disulfide linkage. In another embodiment, greater than 60% of the molecules are present in a form in which the two heavy chain portions are linked via at least one interchain disulfide linkage. In another embodiment, greater than 70% of the molecules are present in a form in which the two heavy chain portions are linked via at least one interchain disulfide linkage. In another embodiment, greater than 80% of the molecules are present in a form in which the two heavy chain portions are linked via at least one interchain disulfide linkage. In another embodiment, greater than 90% of the molecules are present in a form in which the two heavy chain portions are linked via at least one interchain disulfide linkage.

In one embodiment, the subject purification method yields a composition comprising recombinant polypeptide molecules having at least two binding sites and two heavy chain portions, wherein greater than 99% of the molecules are present in a form in which the two heavy chain portions are linked via at least one interchain disulfide linkage.

In one embodiment, the subject purification method yields a composition comprising polypeptide molecules having at least two binding sites and two heavy chain portions, wherein greater than 95% of the molecules are present in a form in which the two heavy chain portions are linked via at least one interchain disulfide linkage, and wherein the heavy chain portions of the polypeptides are derived from an antibody of the IgG4 isotype.

In one embodiment, the subject purification method yields a composition comprising polypeptide molecules having two light chain portions and two heavy chain portions, wherein the heavy chain portions lack CH2 domains and wherein greater than 80% of the molecules are present in a form in which the two heavy chain portions are not linked via at least one interchain disulfide linkage.

In another aspect, the instant invention also provides methods for monitoring the results of purification and/or preferential biosynthesis comprising measuring the relative amounts of Form A and Form B in a composition. Form A and Form B can be measured, e.g., as described herein using non-reducing SDS polyacrylamide gel electrophoresis or mass spectrometry.

V. LABELING OR CONJUGATION OF POLYPEPTIDES

The polypeptide molecules of the present invention may be used in non-conjugated form or may be conjugated to at least one of a variety of molecules, e.g., to facilitate target detection or for imaging or therapy of the patient. The polypeptides of the invention can be labeled or conjugated either before or after purification, when purification is performed. In particular, the polypeptides of the present invention may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG. In another embodiment, a polypeptide of the invention can be conjugated to a molecule that decreases vascularization of tumors. In other embodiments, the disclosed compositions may comprise polypeptides of the invention coupled to drugs or prodrugs. Still other embodiments of the present invention comprise the use of polypeptides of the invention conjugated to specific biotoxins or their cytotoxic fragments such as ricin, gelonin, pseudomonas exotoxin or diphtheria toxin. The selection of which conjugated or unconjugated polypeptide to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy cells in solid tumors as well as lymphomas/leukemias in animal models, and in some cases in humans. Exemplary radioisotopes include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

With respect to the use of radiolabeled conjugates in conjunction with the present invention, polypeptides of the invention may be directly labeled (such as through iodination) or may be labeled indirectly through the use of a chelating agent. As used herein, the phrases "indirect labeling" and "indirect labeling approach" both mean that a chelating agent is covalently attached to a binding molecule and at least one radionuclide is associated with the chelating agent. Such chelating agents are typically referred to as bifunctional chelating agents as they bind both the polypeptide and the radioisotope. Particularly preferred chelating agents comprise 1-isothiocycmatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

As used herein, the phrases "direct labeling" and "direct labeling approach" both mean that a radionuclide is covalently attached directly to a polypeptide (typically via an amino acid residue). More specifically, these linking technologies include random labeling and site-directed labeling. In the latter case, the labeling is directed at specific sites on the polypeptide, such as the N-linked sugar residues present only on the Fc portion of the conjugates. Further, various direct labeling techniques and protocols are compatible with the instant invention. For example, Technetium-99m labeled polypeptides may be prepared by ligand exchange processes, by reducing pertechnate ($TcO_4^-$) with stannous ion solution, chelating the reduced technetium onto a Sephadex column and applying the polypeptides to this column, or by batch labeling techniques, e.g. by incubating pertechnate, a reducing agent such as $SnCl_2$, a buffer solution such as a sodium-potassium phthalate-solution, and the antibodies. In any event, preferred radionuclides for directly labeling antibodies are well known in the art and a particularly preferred radionuclide for direct labeling is $^{131}$I covalently attached via tyrosine residues. Polypeptides according to the invention may be derived, for example, with radioactive sodium or potassium iodide and a chemical oxidizing agent, such as sodium hypochlorite, chloramine T or the like, or an enzymatic oxidizing agent, such as lactoperoxidase, glucose oxidase and glucose. However, for the purposes of the present invention, the indirect labeling approach is particularly preferred.

Patents relating to chelators and chelator conjugates are known in the art. For instance, U.S. Pat. No. 4,831,175 of Gansow is directed to polysubstituted diethylenetriamine-pentaacetic acid chelates and protein conjugates containing the same, and methods for their preparation. U.S. Pat. Nos. 5,099,069, 5,246,692, 5,286,850, 5,434,287 and 5,124,471 of Gansow also relate to polysubstituted DTPA chelates. These patents are incorporated herein in their entirety. Other examples of compatible metal chelators are ethylenediamine-tetraacetic acid (EDTA), diethylenetriaminepentaacetic acid (DPTA), 1,4,8,11-tetraazatetradecane, 1,4,8,11-tetraazatet-radecane-1,4,8,11-tetraacetic acid, 1-oxa-4,7,12,15-tetraaza-heptadecane-4,7,12,15-tetraacetic acid, or the like. Cyclohexyl-DTPA or CHX-DTPA is particularly preferred and is exemplified extensively below. Still other compatible chelators, including those yet to be discovered, may easily be discerned by a skilled artisan and are clearly within the scope of the present invention.

Compatible chelators, including the specific bifunctional chelator used to facilitate chelation in co-pending application Ser. Nos. 08/475,813, 08/475,815 and 08/478,967, are preferably selected to provide high affinity for trivalent metals, exhibit increased tumor-to-non-tumor ratios and decreased bone uptake as well as greater in vivo retention of radionuclide at target sites, i.e., B-cell lymphoma tumor sites. However, other bifunctional chelators that may or may not possess all of these characteristics are known in the art and may also be beneficial in tumor therapy. It will also be appreciated that, in accordance with the teachings herein, polypeptides may be conjugated to different radiolabels for diagnostic and therapeutic purposes. To this end the aforementioned co-pending applications, herein incorporated by reference in their entirety, disclose radiolabeled therapeutic conjugates for diagnostic "imaging" of tumors before administration of therapeutic antibody. "In2B8" conjugate comprises a murine monoclonal antibody, 2B8, specific to human CD20 antigen, that is attached to $^{111}$In via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}$In is particularly preferred as a diagnostic radionuclide because between about 1 to about 10 mCi can be safely administered without detectable toxicity; and the imaging data is generally predictive of subsequent $^{90}$Y-labeled antibody distribution. Most imaging studies utilize 5 mCi $^{111}$In-labeled antibody, because this dose is both safe and has increased imaging efficiency compared with lower doses, with optimal imaging occurring at three to six days after antibody administration. See, for example, Murray, *J. Nuc. Med.* 26: 3328 (1985) and Carraguillo et al., *J. Nuc. Med.* 26: 67 (1985).

As indicated above, a variety of radionuclides are applicable to the present invention and those skilled in the can readily determine which radionuclide is most appropriate under various circumstances. For example, $^{131}$I is a well known radionuclide used for targeted immunotherapy. However, the clinical usefulness of $^{131}$I can be limited by several factors including: eight-day physical half-life; dehalogenation of iodinated antibody both in the blood and at tumor sites; and emission characteristics (e.g., large gamma component) which can be suboptimal for localized dose deposition in tumor. With the advent of superior chelating agents, the opportunity for attaching metal chelating groups to proteins has increased the opportunities to utilize other radionuclides such as $^{111}$In and $^{90}$Y. $^{90}$Y provides several benefits for utilization in radioimmunotherapeutic applications: the 64 hour half-life of $^{90}$Y is long enough to allow antibody accumulation by tumor and, unlike e.g., $^{131}$I, $^{90}$Y is a pure beta emitter of high energy with no accompanying gamma irradiation in its decay, with a range in tissue of 100 to 1,000 cell diameters. Furthermore, the minimal amount of penetrating radiation allows for outpatient administration of $^{90}$Y-labeled antibodies. Additionally, internalization of labeled antibody is not required for cell killing, and the local emission of ionizing radiation should be lethal for adjacent tumor cells lacking the target molecule.

Those skilled in the art will appreciate that these non-radioactive conjugates may also be assembled using a variety of techniques depending on the selected agent to be conjugated. For example, conjugates with biotin are prepared e.g. by reacting the polypeptides with an activated ester of biotin such as the biotin N-hydroxysuccinimide ester. Similarly, conjugates with a fluorescent marker may be prepared in the presence of a coupling agent, e.g. those listed above, or by reaction with an isothiocyanate, preferably fluorescein-isothiocyanate. Conjugates of the polypeptides of the invention with cytostatic/cytotoxic substances and metal chelates are prepared in an analogous manner.

Preferred agents for use in the present invention are cytotoxic drugs, particularly those which are used for cancer therapy. As used herein, "a cytotoxin or cytotoxic agent" means any agent that is detrimental to the growth and proliferation of cells and may act to reduce, inhibit or destroy a cell or malignancy. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. Any cytotoxin that acts to retard or slow the growth of immunoreactive cells or malignant cells is within the scope of the present invention.

Exemplary cytotoxins include, in general, cytostatic agents, alkylating agents, antimetabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. Other preferred classes of cytotoxic agents include, for example, the maytansinoid family of drugs. Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. As noted previously, one skilled in the art may make chemical modifications to the desired compound in order to make reactions of that compound more convenient for purposes of preparing conjugates of the invention.

One example of particularly preferred cytotoxins comprise members or derivatives of the enediyne family of anti-tumor antibiotics, including calicheamicin, esperamicins or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present only on the Fc portion of the constructs. Such site-directed linking methods have the advantage of reducing the possible effects of linkage on the binding properties of the constructs.

As previously alluded to, compatible cytotoxins may comprise a prodrug. As used herein, the term "prodrug" refers to a precursor or derivative form of a pharmaceutically active substance that is less cytotoxic to tumor cells compared to the parent drug and is capable of being enzymatically activated or converted into the more active parent form. Prodrugs compatible with the invention include, but are not limited to, phosphate-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. Further examples of cytotoxic drugs that can be derivatized into a prodrug form for use in the present invention comprise those chemotherapeutic agents described above.

Among other cytotoxins, it will be appreciated that polypeptides can also be associated with a biotoxin such as ricin subunit A, abrin, diptheria toxin, botulinum, cyanginosins, saxitoxin, shigatoxin, tetanus, tetrodotoxin, trichothecene, verrucologen or a toxic enzyme. Preferably, such constructs will be made using genetic engineering techniques that allow for direct expression of the antibody-toxin construct. Other biological response modifiers that may be associated with the polypeptides of the invention of the present invention comprise cytokines such as lymphokines and interferons. In view of the instant disclosure it is submitted that one skilled in the art could readily form such constructs using conventional techniques.

Another class of compatible cytotoxins that may be used in conjunction with the disclosed polypeptides are radiosensitizing drugs that may be effectively directed to tumor or immunoreactive cells. Such drugs enhance the sensitivity to ionizing radiation, thereby increasing the efficacy of radiotherapy. An antibody conjugate internalized by the tumor cell would deliver the radiosensitizer nearer the nucleus where radiosensitization would be maximal. The unbound radiosensitizer linked polypeptides of the invention would be cleared quickly from the blood, localizing the remaining radiosensitization agent n the target tumor and providing minimal uptake in normal tissues. After rapid clearance from the blood, adjunct radiotherapy would be administered in one of three ways: 1.) external beam radiation directed specifically to the tumor, 2.) radioactivity directly implanted in the tumor or 3.) systemic radioimmunotherapy with the same targeting antibody. A potentially attractive variation of this approach would be the attachment of a therapeutic radioisotope to the radiosensitized immunoconjugate, thereby providing the convenience of administering to the patient a single drug.

In one embodiment, a moiety that enhances the stability or efficacy of the polypeptide can be conjugated. For example, in one embodiment, PEG can be conjugated to the polypeptides of the invention to increase their half-life in vivo. Leong, S. R., et al. 2001. *Cytokine* 16:106; 2002; *Adv. in Drug Deliv. Rev.* 54:531; or Weir et al. 2002. Biochem. Soc. Transactions 30:512.

VI. ADMINISTRATION OF POLYPEPTIDES

Methods of preparing and administering polypeptides of the invention to a subject are well known to or are readily determined by those skilled in the art. The route of administration of the polypeptide of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders. Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy. For passive immunization with an antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Polypeptides of the invention can be administered on multiple occasions. Intervals between single dosages can be weekly, monthly or yearly. Intervals can also be irregular as indicated by measuring blood levels of polypeptide or target molecule in the patient. In some methods, dosage is adjusted to achieve a plasma polypeptide concentration of 1-1000 µg/ml and in some methods 25-300 µg/ml. Alternatively, binding molecules can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies. In one embodiment, the binding molecules of the invention can be administered in unconjugated form, In another embodiment, the polypeptides of the invention can be administered multiple times in conjugated form. In still another embodiment, the binding molecules of the invention can be administered in unconjugated form, then in conjugated form, or vise versa.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of binding molecule, e.g., antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a polypeptide of the invention (e.g., in a vector). Doses for nucleic acids encoding polypeptides range from about 10 ng to 1 g, 100 ng to 100 mg, 1 µg to 10 mg, or 30-300 µg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are effective in treating the disorder or condition in need of treatment (e.g., prophylactic or therapeutic).

Effective single treatment dosages (i.e., therapeutically effective amounts) of $^{90}$Y-labeled polypeptides of the invention range from between about 5 and about 75 mCi, more preferably between about 10 and about 40 mCi. Effective single treatment non-marrow ablative dosages of $^{131}$I-labeled antibodies range from between about 5 and about 70 mCi, more preferably between about 5 and about 40 mCi. Effective single treatment ablative dosages (i.e., may require autologous bone marrow transplantation) of $^{131}$I-labeled antibodies range from between about 30 and about 600 mCi, more preferably between about 50 and less than about 500 mCi. In conjunction with a chimeric antibody, owing to the longer circulating half life vis-á-vis murine antibodies, an effective single treatment non-marrow ablative dosages of iodine-131 labeled chimeric antibodies range from between about 5 and about 40 mCi, more preferably less than about 30 mCi. Imaging criteria for, e.g., the $^{111}$In label, are typically less than about 5 mCi.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$Cu, $^{77}$Br, $^{81}$Rb, $^{81}$Kr, $^{87}$Sr, $^{113}$In, $^{127}$Cs, $^{129}$Cs, $^{132}$I, $^{197}$Hg, $^{203}$Pb, $^{206}$Bi, $^{177}$Lu, $^{186}$Re, $^{212}$Pb, $^{212}$Bi, $^{47}$Sc, $^{105}$Rh, $^{109}$Pd, $^{153}$Sm, $^{188}$Re, $^{199}$Au, $^{225}$Ac $^{211}$At, and $^{213}$Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{123}$I, $^{99}$Tc, $^{43}$K, $^{52}$Fe, $^{67}$Ga, $^{68}$Ga, as well as $^{111}$In. Antibodies have also been labeled with a variety of radionuclides for potential use in targeted immunotherapy (Peirersz et al. *Immunol. Cell Biol.* 65: 111-125 (1987)). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

Whether or not the polypeptides of the invention are used in a conjugated or unconjugated form, it will be appreciated that a major advantage of the present invention is the ability to use these polypeptides in myelosuppressed patients, especially those who are undergoing, or have undergone, adjunct therapies such as radiotherapy or chemotherapy. That is, the beneficial delivery profile (i.e. relatively short serum dwell time, high binding affinity and enhanced localization) of the polypeptides makes them particularly useful for treating patients that have reduced red marrow reserves and are sensitive to myelotoxicity. In this regard, the unique delivery profile of the polypeptides make them very effective for the administration of radiolabeled conjugates to myelosuppressed cancer patients. As such, the polypeptides of the invention are useful in a conjugated or unconjugated form in patients that have previously undergone adjunct therapies such as external beam radiation or chemotherapy. In other preferred embodiments, the polypeptides (again in a conjugated or unconjugated form) may be used in a combined therapeutic regimen with chemotherapeutic agents. Those skilled in the art will appreciate that such therapeutic regimens may comprise the sequential, simultaneous, concurrent or coextensive administration of the disclosed antibodies and one or more chemotherapeutic agents. Particularly preferred embodiments of this aspect of the invention will comprise the administration of a radiolabeled polypeptide.

While the polypeptides may be administered as described immediately above, it must be emphasized that in other embodiments conjugated and unconjugated polypeptides may be administered to otherwise healthy patients as a first line therapeutic agent. In such embodiments the polypeptides may be administered to patients having normal or average red marrow reserves and/or to patients that have not, and are not, undergoing adjunct therapies such as external beam radiation or chemotherapy.

However, as discussed above, selected embodiments of the invention comprise the administration of polypeptides to myelosuppressed patients or in combination or conjunction with one or more adjunct therapies such as radiotherapy or chemotherapy (i.e. a combined therapeutic regimen). As used herein, the administration of polypeptides in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the present invention. Conversely, cytotoxin associated polypeptides could be administered intravenously followed by tumor localized external beam radiation. In yet other embodiments, the polypeptide may be administered concurrently with one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard it will be appreciated that the combination of the polypeptide (with or without cytotoxin) and the chemotherapeutic agent may be administered in any order and within any time frame that provides a therapeutic benefit to the patient. That is, the chemotherapeutic agent and polypeptide may be administered in any order or concurrently. In selected embodiments the polypeptides of the present invention will be administered to patients that have previously undergone chemotherapy. In yet other embodiments, the polypeptides and the chemotherapeutic treatment will be administered substantially simultaneously or concurrently. For example, the patient may be given the binding molecule while undergoing a course of chemotherapy. In preferred embodiments the binding molecule will be administered within 1 year of any chemotherapeutic agent or treatment. In other preferred embodiments the polypeptide will be administered within 10, 8, 6, 4, or 2 months of any chemotherapeutic agent or treatment. In still other preferred embodiments the polypeptide will be administered within 4, 3, 2 or 1 week of any chemotherapeutic agent or treatment. In yet other embodiments the polypeptide will be administered within 5, 4, 3, 2 or 1 days of the selected chemotherapeutic agent or treatment. It will further be appreciated that the two agents or treatments may be administered to the 30' patient within a matter of hours or minutes (i.e. substantially simultaneously).

Moreover, in accordance with the present invention a myelosuppressed patient shall be held to mean any patient exhibiting lowered blood counts. Those skilled in the art will appreciate that there are several blood count parameters conventionally used as clinical indicators of myelosuppresion and one can easily measure the extent to which myelosuppresion is occurring in a patient. Examples of art accepted myelosuppression measurements are the Absolute Neutrophil Count (ANC) or platelet count. Such myelosuppression or partial myeloablation may be a result of various biochemical disorders or diseases or, more likely, as the result of prior chemotherapy or radiotherapy. In this respect, those skilled in the art will appreciate that patients who have undergone traditional chemotherapy typically exhibit reduced red marrow reserves. As discussed above, such subjects often cannot be treated using optimal levels of cytotoxin (i.e. radionuclides) due to unacceptable side effects such as anemia or immunosuppression that result in increased mortality or morbidity.

More specifically conjugated or unconjugated polypeptides of the present invention may be used to effectively treat patients having ANCs lower than about 2000/mm$^3$ or platelet counts lower than about 150,000/mm$^3$. More preferably the polypeptides of the present invention may be used to treat patients having ANCs of less than about 1500/mm$^3$, less than about 1000/mm$^3$ or even more preferably less than about 500/mm$^3$. Similarly, the polypeptides of the present invention may be used to treat patients having a platelet count of less than about 75,000/mm$^3$, less than about 50,000/mm$^3$ or even less than about 10,000/mm$^3$. In a more general sense, those skilled in the art will easily be able to determine when a patient is myelosuppressed using government implemented guidelines and procedures.

As indicated above, many myelosuppressed patients have undergone courses of treatment including chemotherapy, implant radiotherapy or external beam radiotherapy. In the case of the latter, an external radiation source is for local irradiation of a malignancy. For radiotherapy implantation methods, radioactive reagents are surgically located within the malignancy, thereby selectively irradiating the site of the disease. In any event, the disclosed polypeptides may be used to treat disorders in patients exhibiting myelosuppression regardless of the cause.

In this regard it will further be appreciated that the polypeptides of the instant invention may be used in conjunction or combination with any chemotherapeutic agent or agents (e.g. to provide a combined therapeutic regimen) that eliminates, reduces, inhibits or controls the growth of neoplastic cells in vivo. As discussed, such agents often result in the reduction of red marrow reserves. This reduction may be offset, in whole or in part, by the diminished myelotoxicity of the compounds of the present invention that advantageously allow for the aggressive treatment of neoplasias in such patients. In other preferred embodiments the radiolabeled immunoconjugates disclosed herein may be effectively used with radiosensitizers that increase the susceptibility of the neoplastic cells to radionuclides. For example, radiosensitizing compounds may be administered after the radiolabeled binding molecule has been largely cleared from the bloodstream but still remains at therapeutically effective levels at the site of the tumor or tumors.

With respect to these aspects of the invention, exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), ChlVPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas*, in HARRISON'S PRINCIPLES OF INTERNAL MEDICINE 1774-1788 (Kurt J. Isselbacher et al., eds., 13$^{th}$ ed. 1994) and V. T. DeVita et al., (1997) and the references cited therein for standard dosing and scheduling. These therapies can be used unchanged, or altered as needed for a particular patient, in combination with one or more polypeptides of the invention as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), Pro-MACE-MOPP (prednisone, methotrexate, doxorubicin, cyclophosphamide, etoposide and leucovonn plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, cisplatin, etoposide and ifosfamide given alone or in combination. In relapsed or aggressive forms of certain neoplastic disorders the following protocols are often used: IMVP-16 (ifosfamide, methotrexate and etoposide), MIME (methylgag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9$^{th}$ ed. 1996).

As previously discussed, the polypeptides of the present invention, immunoreactive fragments or recombinants thereof may be administered in a pharmaceutically effective amount for the in vivo treatment of mammalian disorders. In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of the polypeptide, immunoreactive fragment or recombinant thereof, conjugated or unconjugated to a therapeutic agent, shall be held to mean an amount sufficient to achieve effective binding to a target and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the polypeptides of the invention may be administered to a human or other animal in accordance with the aforementioned methods of treatment in an amount sufficient to produce a therapeutic or prophylactic effect. The polypeptides of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

VI. METHODS OF USE

The molecules of the invention can be used for diagnostic or therapeutic purposes. Preferred embodiments of the present invention provide compounds, compositions, kits and methods for the diagnosis and/or treatment of disorders, e.g., neoplastic disorders in a mammalian subject in need of such treatment. Preferably, the subject is a human.

The polypeptides of the instant invention will be useful in a number of different applications. For example, in one embodiment, the subject binding molecules should be useful for reducing or eliminating cells bearing target (e.g., an epitope) recognized by a binding molecule of the invention. In another embodiment, the subject binding molecules are effective in reducing the concentration of or eliminating soluble target molecules in the circulation.

In one embodiment, tumor size, inhibiting tumor growth and/or prolonging the survival time of tumor-bearing animals. Accordingly, this invention also relates to a method of treating tumors in a human or other animal by administering to such human or animal an effective, non-toxic amount of polypeptide. One skilled in the art would be able, by routine experimentation, to determine what an effective, non-toxic amount of polypeptide would be for the purpose of treating malignancies. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

For purposes of clarification "mammal" refers to any animal classified as a mammal, including humans, domestic and farm animals, and zoo, sports, or pet animals, such as dogs, horses, cats, cows, etc. Preferably, the mammal is human. "Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

As discussed above, the polypeptides of the present invention may bind to one or more tumor molecules or molecules associated with immune disorders. In one embodiment, for neoplastic disorders, an antigen binding site (i.e. the variable region or immunoreactive fragment or recombinant thereof) of the disclosed polypeptides binds to a selected tumor associated molecule at the site of the malignancy. Similarly, in immune (including autoimmune) disorders the disclosed polypeptides will bind to selected markers on the offending cells. Given the number of reported molecules associated with neoplasias and immune disorders, and the number of related antibodies, those skilled in the art will appreciate that the presently disclosed polypeptides may therefore be derived from any one of a number of whole antibodies. More generally, polypeptides useful in the present invention may be obtained or derived from any antibody (including those previously reported in the literature) that reacts with a target or marker associated with the selected condition. Further, the parent or precursor antibody, or fragment thereof, used to generate the disclosed polypeptides may be murine, human, chimeric, humanized, non-human primate or primatized. In other preferred embodiments the polypeptides of the present invention may comprise single chain antibody constructs (such as that disclosed in U.S. Pat. No. 5,892,019 which is incorporated herein by reference) having altered constant domains as described herein. Consequently, any of these types of antibodies synthetic in accordance with the teachings herein is compatible with the instant invention.

As used herein, "tumor associated molecules" means any antigen or target molecule which is generally associated with tumor cells, i.e., occurring at the same or to a greater extent as compared with normal cells. More generally, tumor associated molecules comprise any molecule that provides for the localization of immunoreactive antibodies at a neoplastic cell irrespective of its expression on non-malignant cells. Such molecules may be relatively tumor specific and limited in their expression to the surface of malignant cells. Alternatively, such molecules may be found on both malignant and non-malignant cells. For example, CD20 is a pan B antigen that is found on the surface of both malignant and non-malignant B cells that has proved to be an extremely effective target for immunotherapeutic antibodies for the treatment of non-Hodgkin's lymphoma. In this respect, pan T cell antigens such as CD2, CD3, CD5, CD6 and CD7 also comprise tumor associated molecules within the meaning of the present invention. Still other exemplary tumor associated molecules comprise but not limited to MAGE-1, MAGE-3, MUC-1, HPV 16, HPV E6 & E7, TAG-72, CEA, L6-Antigen, CD19, CD22, CD37, CD52, HLA-DR, EGF Receptor and HER2 Receptor. In many cases immunoreative antibodies for each of these antigens have been reported in the literature. Those skilled in the art will appreciate that each of these antibodies may serve as a precursor for polypeptides of the invention in accordance with the present invention.

The polypeptides of the present invention preferably associate with, and bind to, tumor or immune associated molecules as described above. Accordingly, as will be discussed in some detail below the polypeptides of the present invention may be derived, generated or fabricated from any one of a number of antibodies that react with tumor associated molecules. In preferred embodiments the polypeptides are synthetic or domain deleted antibodies that are derived using common genetic engineering techniques whereby at least a portion of one or more constant region domains are deleted or altered so as to provide the desired biochemical characteristics such as reduced serum half-life. More particularly, as will be exemplified below, one skilled in the art may readily isolate the genetic sequence corresponding to the variable and/or constant regions of the subject antibody and delete or alter the appropriate nucleotides to provide polypeptides of the invention for use as monomeric subunits in accordance with the instant invention. It will further be appreciated that compatible polypeptides of the invention may be expressed and produced on a clinical or commercial scale using well-established protocols.

Previously reported antibodies that react with tumor associated molecules may be altered as described herein to provide the polypeptides of the present invention. Exemplary antibodies that may be used to provide antigen binding regions for, generate or derive the disclosed polypeptides include, but are not limited to 2B8 and C2B8 (Zevalin® and Rituxan®, IDEC Pharmaceuticals Corp., San Diego), Lym 1 and Lym 2 (Techniclone), LL2 (Immunomedics Corp., New Jersey), HER2 (Herceptin®, Genentech Inc., South San Francisco), B1 (Bexxar®, Coulter Pharm., San Francisco), Campath® (Millennium Pharmaceuticals, Cambridge) MB1, BH3, B4, B72.3 (Cytogen Corp.), CC49 (National Cancer Institute) and 5E10 (University of Iowa). In preferred embodiments, the polypeptides of the present invention will bind to the same tumor associated antigens as the antibodies enumerated immediately above. In particularly preferred embodiments, the polypeptides will be derived from or bind the same antigens as 2B8, C2B8, CC49 and C5E10 and, even more preferably, will comprise domain deleted antibodies (i.e., ΔCH2 antibodies).

In a first preferred embodiment, the polypeptide will bind to the same tumor associated antigen as Rituxan®. Rituxan® (also known as, rituximab, IDEC-C2B8 and C2B8) was the first FDA-approved monoclonal antibody for treatment of human B-cell lymphoma (see U.S. Pat. Nos. 5,843,439; 5,776,456 and 5,736,137 each of which is incorporated herein by reference). Y2B8 (90Y labeled 2B8; Zevalin®; ibritumomab tiuxetan) is the murine parent of C2B8. Rituxan® is a chimeric, anti-CD20 monoclonal antibody which is growth inhibitory and reportedly sensitizes certain lymphoma cell lines for apoptosis by chemotherapeutic agents in vitro. The antibody efficiently binds human complement, has strong FcR binding, and can effectively kill human lymphocytes in vitro via both complement dependent (CDC) and antibody-dependent (ADCC) mechanisms (Reff et al., *Blood* 83: 435-445 (1994)). Those skilled in the art will appreciate that dimeric variants (homodimers or heterodimers) of C2B8 or 2B8, synthetic according to the instant disclosure, may be used in conjugated or unconjugated forms to effectively treat patients presenting with CD20+ malignancies. More generally, it must be reiterated that the polypeptides disclosed herein may be used in either a "naked" or unconjugated state or conjugated to a cytotoxic agent to effectively treat any one of a number of disorders.

In other preferred embodiments of the present invention, the polypeptide of the invention will be derived from, or bind to, the same tumor associated antigen as CC49. As previously alluded to, CC49 binds human tumor associated antigen TAG-72 which is associated with the surface of certain tumor cells of human origin, specifically the LS174T tumor cell line. LS174T [American Type Culture Collection (herein ATCC) No. CL 188] is a variant of the LS180 (ATCC No. CL 187) colon adenocarcinoma line.

It will further be appreciated that numerous murine monoclonal antibodies have been developed which have binding specificity for TAG-72. One of these monoclonal antibodies, designated B72.3, is a murine IgG1 produced by hybridoma B72.3 (ATCC No. HB-8108). B72.3 is a first generation monoclonal antibody developed using a human breast carcinoma extract as the immunogen (see Colcher et al., Proc. Natl. Acad. Sci. (USA), 78:3199-3203 (1981); and U.S. Pat. Nos. 4,522,918 and 4,612,282 each of which is incorporated herein by reference). Other monoclonal antibodies directed against TAG-72 are designated "CC" (for colon cancer). As described by Schlom et al. (U.S. Pat. No. 5,512,443 which is incorporated herein by reference) CC monoclonal antibodies are a family of second generation murine monoclonal antibodies that were prepared using TAG-72 purified with B72.3. Because of their relatively good binding affinities to TAG-72, the following CC antibodies have been deposited at the ATCC, with restricted access having been requested: CC49 (ATCC No. HB 9459); CC 83 (ATCC No. HB 9453); CC46 (ATCC No. HB 9458); CC92 (ATTCC No. HB 9454); CC30 (ATCC No. HB 9457); CC11 (ATCC No. 9455); and CC15 (ATCC No. HB 9460). U.S. Pat. No. 5,512,443 further teaches that the disclosed antibodies may be altered into their chimeric form by substituting, e.g., human constant regions (Fc) domains for mouse constant regions by recombinant DNA techniques known in the art. Besides disclosing murine and chimeric anti-TAG-72 antibodies, Schlom et al. have also produced variants of a humanized CC49 antibody as disclosed in PCT/US99/25552 and single chain constructs as disclosed in U.S. Pat. No. 5,892,019 each of which is also incorporated herein by reference. Those skilled in the art will appreciate that each of the foregoing antibodies, constructs or recombinants, and variations thereof, may be synthetic and used to provide polypeptides in accordance with the present invention.

In addition to the anti-TAG-72 antibodies discussed above, various groups have also reported the construction and partial characterization of domain-deleted CC49 and B72.3 antibodies (e.g., Calvo et al. *Cancer Biotherapy*, 8(1):95-109 (1993), Slavin-Chiorini et al. *Int. J. Cancer* 53:97-103 (1993) and Slavin-Chiorini et al. *Cancer. Res.* 55:5957-5967 (1995).

In one embodiment, a binding molecule of the invention binds to the CD23 (U.S. Pat. No. 6,011,138). In a preferred embodiment, a binding molecule of the invention binds to the same epitope as the 5E8 antibody. In another embodiment, a binding molecule of the invention comprises at least one CDR from an anti-CD23 antibody, e.g., the 5E8 antibody.

In one embodiment, a binding molecule of the invention binds to the CRIPTO-I antigen (WO02/088170A2 or WO03/083041A2). In a preferred embodiment, a binding molecule of the invention binds to the same epitope as the B3F6 antibody. In another embodiment, a binding molecule of the invention comprises at least one CDR from an anti-CRIPTO-I antibody, e.g., the B3F6 antibody.

Still other preferred embodiments of the present invention comprise modified antibodies that are derived from or bind to the same tumor associated antigen as C5E10. As set forth in co-pending application Ser. No. 09/104,717, C5E10 is an antibody that recognizes a glycoprotein determinant of approximately 115 kDa that appears to be specific to prostate tumor cell lines (e.g. DU145, PC3, or ND1). Thus, in conjunction with the present invention, polypeptides (e.g. CH2 domain-deleted antibodies) that specifically bind to the same tumor associated antigen recognized by C5E10 antibodies could be produced and used in a conjugated or unconjugated form for the treatment of neoplastic disorders. In particularly preferred embodiments, the binding molecule will be derived or comprise all or part of the antigen binding region of the C5E10 antibody as secreted from the hybridoma cell line having ATCC accession No. PTA-865. The resulting binding molecule could then be conjugated to a radionuclide as described below and administered to a patient suffering from prostate cancer in accordance with the methods herein.

In general, the disclosed invention may be used to prophylactically or therapeutically treat any neoplasm comprising a marker that allows for the targeting of the cancerous cells by the binding molecule. Exemplary cancers that may be treated include, but are not limited to, prostate, gastric carcinomas such as colon, skin, breast, ovarian, lung and pancreatic. More particularly, the antibodies of the instant invention may be used to treat Kaposi's sarcoma, CNS neoplasias (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the ovary, Wilm's tumor or small cell lung carcinoma. It will be appreciated that appropriate polypeptides may be derived for tumor associated molecules related to each of the forgoing neoplasias without undue experimentation in view of the instant disclosure.

Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the compounds and methods of the present invention are particularly effective in treating a variety of B-cell lymphomas, including low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies bearing compatible tumor associated molecules.

Besides neoplastic disorders, the polypeptides of the instant invention are particularly effective in the treatment of autoimmune disorders or abnormal immune responses. In this regard, it will be appreciated that the polypeptide of the present invention may be used to control, suppress, modulate or eliminate unwanted immune responses to both external and autoantigens. For example, in one embodiment, the antigen is an autoantigen. In another embodiment, the antigen is an allergen. In yet other embodiments, the antigen is an alloantigen or xenoantigen. Use of the disclosed polypeptides to reduce an immune response to alloantigens and xenoantigens is of particular use in transplantation, for example to inhibit rejection by a transplant recipient of a donor graft, e.g. a tissue or organ graft or bone marrow transplant. Additionally, suppression or elimination of donor T cells within a bone marrow graft is useful for inhibiting graft versus host disease.

In yet other embodiments the polypeptides of the present invention may be used to treat immune disorders that include, but are not limited to, allergic bronchopulmonary aspergillosis; Allergic rhinitis Autoimmune hemolytic anemia; Acanthosis nigricans; Allergic contact dermatitis; Addison's disease; Atopic dermatitis; Alopecia greata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus; Pemphigus foliaceus; Pemphigus vulgaris; Pigeon breeder's disease; Pneumonitis, hypersensitivity; Polyarteritis nodosa; Polymyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Serum sickness; Sezary syndrome; Sjogren's syndrome; Stevens-Johnson syndrome; Still's disease; Subacute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis and Wiskott-Aldrich syndrome.

This invention is further illustrated by the following examples which should not be construed as limiting. The contents of all references, patents and published patent applications cited throughout this application are incorporated herein by reference.

EXAMPLES

Example 1

Identification of A and B Forms

Figure 2:
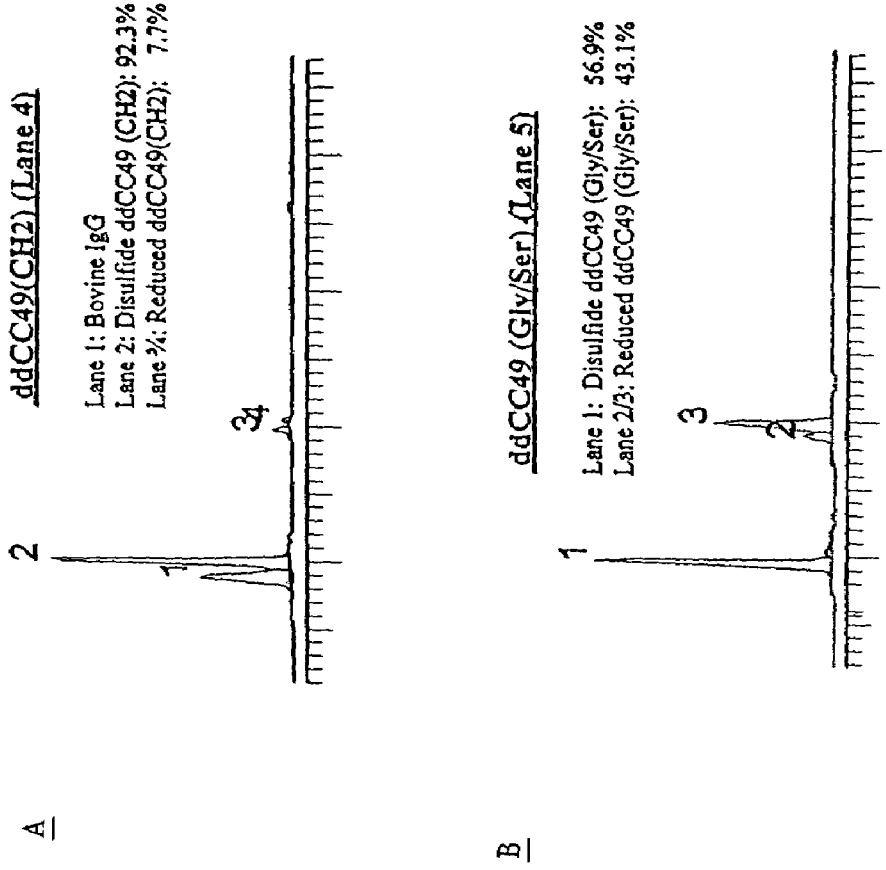
FIGS. 2A and B show densitometer plots of non-reducing SDS-PAGE gels for ddCC49 (with a CH2 spacer) and ddCC49 (with a Gly/Ser spacer), respectively.

Solutions of antibody molecules comprise two different isoforms. One form, Form A comprises heavy chain molecules that are linked via at least one disulfide linkage. The other form, Form B, comprises heavy chain molecules that are not linked via at least one disulfide linkage. Form B does not appear or appears at a very low frequency in with intact gamma 1 MAbs, such as Rituxan®. However with domain deleted (dd) constructs having a similar hinge, the frequency of Form B is much higher. These forms can be distinguished using denaturing, non-reducing SDS page. In domain deleted antibody preparations, Form A appears as a 120 kDa dimer while Form B appears as a 60 kDa monomer (FIG. 1). FIGS. 2A and 2B show densitometer plots of non-reducing SDS-PAGE gels for ddCC49 (CH2) and ddCC49 (Gly/Ser), respectively.

Example 2

Identification of Hinge Region Heterogeneity in CH2 Domain Deleted MAb Fragments Hinge domains can be subdivided into three distinct regions: upper, middle, and lower hinge regions (Roux et al. J. Immunol. 1998 161:4083). Polypeptide sequences encompassing these regions for IgG1 and IgG3 hinges are shown in Table 1. The IgG3 hinge middle region contains, in addition to the two conserved cysteine residues, a 15 amino acid motif that repeats three times. Amino acid sequences from these regions were used to design synthetic IgG1/IgG3 connecting peptides. These consisted of IgG1 upper hinge residues corresponding to positions 226 through 238, an IgG1 middle hinge corresponding to positions 239 through 241, and a single IgG3 middle hinge repeat motif corresponding to positions 241EE through 242 combined with either an added proline at position 243 or an added proline, alanine, proline at positions 243, 244, and 245, respectively (Kabat numbering system), followed by a flexible Gly/Ser spacer (Table 2). In addition, novel connecting peptides were designed consisting of a serine amino acid residue substituted for the cysteine at positions 239 or 242 combined with either an added proline at position 243 or an added proline, alanine, proline at positions 243, 244, and 245, respectively (Kabat numbering system). Pro243Ala244Pro245 and Pro 243 connecting peptides were also made. The amino acid sequence of the parent CH2 domain deleted humanized CC49 connecting peptide beginning at the first residue of the IgG1 hinge (position 226, Kabat numbering system) to the last residue of the hinge/GlySer connecting peptide is shown in Table 2. Also shown are the various connecting peptide designs by alignment to CC49 with positions of the cysteine residues indicated in Kabat numbering system.

TABLE 1

IgG1, IgG3 and IgG4 Hinge Regions

| IgG | Upper Hinge | Middle Hinge | Lower Hinge |
|---|---|---|---|
| IgG1 | EPKSCDKTHT (SEQ ID NO: 2) | CPPCP (SEQ ID NO: 3) | APELLGGP (SEQ ID NO: 4) |
| IgG3 | ELKTPLGDTTHT (SEQ ID NO: 5) | CPRCP (EPKSCDTPPPCPRCP)$_3$ (SEQ ID NO: 6) | APELLGGP (SEQ ID NO: 4) |
| IgG4 | ESKYGPP (SEQ ID NO: 50) | CPSCP (SEQ ID NO: 51) | APEFLGGP (SEQ ID NO: 52) |

TABLE 2

Hinge Region Connecting Peptide Sequences

| Kabat hinge position: | 226 | 227 | 228 | 229 | 230 | 232 | 235 | 236 | 237 | 238 | 239 | 240 | 241 |
|---|---|---|---|---|---|---|---|---|---|---|---|---|---|
| IgG1 hinge sequence | E | P | K | S | C | D | K | T | H | T | C | P | P |
| IgG4 hinge sequence | E | S | K | Y | G | | | | | P | P | C | P | S |
| IgG3 middle hinge sequence | | | | | | | | | | | | | |
| Connecting peptide: | | | | | Connecting peptide sequences | | | | | | | | |
| G1 | E | P | K | S | C | D | K | T | H | T | C | P | P |
| G1/G3/Pro243 (Seq. ID NO: 7) | E | P | K | S | C | D | K | T | H | T | C | P | P |
| G1/G3/Pro243Ala244Pro245 (Seq. ID NO: 8) | E | P | K | S | C | D | K | T | H | T | C | P | P |
| G1/Cys239Ser:Pro243 (Seq. ID NO: 9) | E | P | K | S | C | D | K | T | H | T | C | P | P |
| G1/Cys239Ser:Pro243Ala244Pro245 (Seq. ID NO: 10) | E | P | K | S | C | D | K | T | H | T | S | P | P |
| G1/Cys242Ser:Pro243 (Seq. ID NO: 11) | E | P | K | S | C | D | K | T | H | T | S | P | P |
| G1/Cys242Ser:Pro243Ala244Pro245 (Seq. ID NO: 12) | E | P | K | S | C | D | K | T | H | T | C | P | P |
| G1/Pro243Ala244Pro245 (Seq. ID NO: 13) | E | P | K | S | C | D | K | T | H | T | C | P | P |
| G1/Pro243 (Seq. ID NO: 14) | E | P | K | S | C | D | K | T | H | T | C | P | P |
| G4/G3/Pro243Ala244Pro245 (Seq. ID NO: 15) | E | P | K | S | C | D | K | T | H | T | C | P | P |
| | E | S | K | Y | G | | | | | P | P | C | P | S |
| (Seq. ID NO: 53) | | | | | | | | | | | | | |

| Kabat hinge position: | 241EE | 241FF | 241GG | 241HH | 241II | 241JJ | 241KK | 241LL | 241MM | 241NN |
|---|---|---|---|---|---|---|---|---|---|---|
| IgG1 hinge sequence | | | | | | | | | | |
| IgG4 hinge sequence | | | | | | | | | | |
| IgG3 middle hinge sequence | C | P | E | P | K | S | C | D | T | P |
| Connecting peptide: | | | | Connecting peptide sequences | | | | | | |
| G1 | | | | | | | | | | |
| G1/G3/Pro243 | C | P | E | P | K | S | C | D | T | P |
| G1/G3/Pro243Ala244Pro245 | C | P | E | P | K | S | C | D | T | P |
| G1/Cys239Ser:Pro243 | | | | | | | | | | |
| G1/Cys239Ser:Pro243Ala244Pro245 | | | | | | | | | | |
| G1/Cys242Ser:Pro243 | | | | | | | | | | |
| G1/Cys242Ser:Pro243Ala244Pro245 | | | | | | | | | | |
| G1/Pro243Ala244Pro245 | | | | | | | | | | |
| G1/Pro243 | | | | | | | | | | |
| G4/G3/Pro243Ala244Pro245 | C | P | E | P | K | S | C | D | T | P |

TABLE 2-continued

| | Hinge Region Connecting Peptide Sequences | | | | | | | | |
|---|---|---|---|---|---|---|---|---|---|
| Kabat hinge position: | 241OO | 241PP | 241OO | 241RR | 241SS | 242 | 243 | 244 | 245 |
| IgG1 hinge sequence | | | | | | C | P | A | P |
| IgG4 hinge sequence | | | | | | C | P | A | P |
| IgG3 middle hinge sequence | P | P | C | P | R | | | | |
| Connecting peptide: | | | | | Connecting peptide sequences | | | | |
| G1 | | | | | | C | | | GGGSSGGGSG |
| G1/G3/Pro243 | P | P | C | P | R | C | P | | GGGSSGGGSG |
| G1/G3/Pro243Ala244Pro245 | P | P | C | P | R | C | P | A | P | GGGSSGGGSG |
| G1/Cys239Ser:Pro243 | | | | | | C | P | | GGGSSGGGSG |
| G1/Cys239Ser:Pro243Ala244Pro245 | | | | | | C | P | A | P | GGGSSGGGSG |
| G1/Cys242Ser:Pro243 | | | | | | S | P | | GGGSSGGGSG |
| G1/Cys242Ser:Pro243Ala244Pro245 | | | | | | S | P | A | P | GGGSSGGGSG |
| G1/Pro243Ala244Pro245 | | | | | | C | P | A | P | GGGSSGGGSG |
| G1/Pro243 | | | | | | C | P | | GGGSSGGGSG |
| G4/G3/Pro243Ala244Pro245 | P | P | C | P | R | C | P | A | P | |

Example 3

Construction of Connecting Polypeptides and Preferential Synthesis of Isoforms Nucleic acid sequences encoding the hinge region connecting peptides shown in Table 2 were introduced into CH2 domain deleted huCC49 gene sequences using the Splicing by Overlap Extension (SOE) method (Horton, R. M. 1993 Methods in Molecular Biology, Vol 15: PCR Protocols: Current Methods and applications. Ed. B. A. White). Correct modifications to the hinge region were confirmed by DNA sequence analysis. Plasmid DNA was used to transform CHO DG44 cells for stable production of antibody protein.

Figure 3:
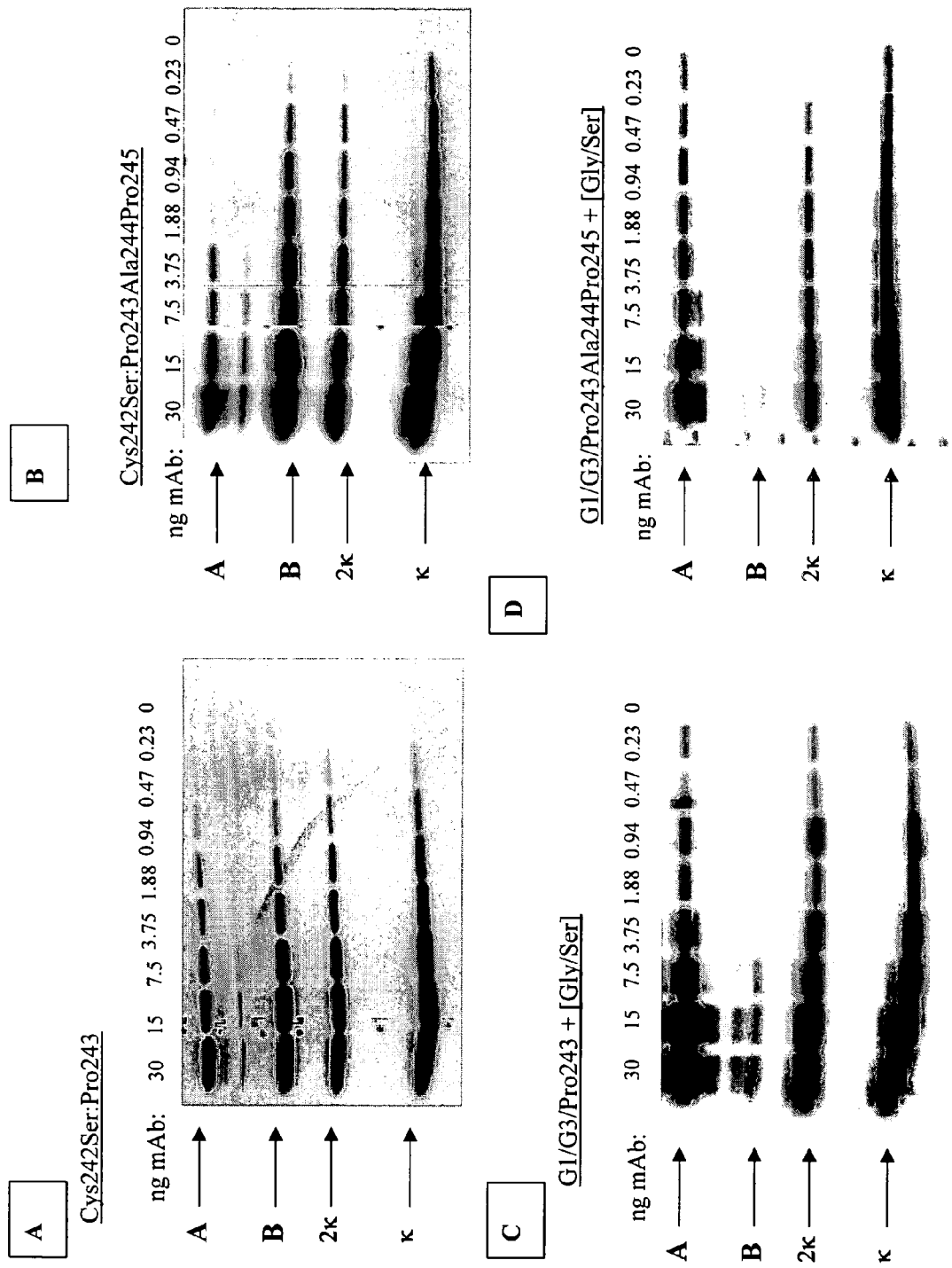
FIGS. 3A-D shows that the G1/G3/Pro243Ala244Pro245+ [Gly/Ser] (FIG. 3D) and G1/G3/Pro243+[Gly/Ser] (FIG. 3C) hinges resulted in the production of primarily Form A CH2 domain-deleted huCC49 antibody with low or essentially no detectable Form B. In contrast, CH2 domain-deleted huCC49 Cys242Ser:Pro243 (FIG. 3A) and CH2 domain-deleted huCC49 Cys242Ser:Pro243Ala244Pro245 (FIG. 3B) resulted in a moderate to significant preference of the Form B isoform, respectively.

CH2 domain deleted huCC49 antibodies containing the eight designed synthetic connecting peptides indicated in Table 2 were constructed and antibody produced in CHO DG44 cells. Supernatants were collected from isolated cell lines and concentration of antibody in the culture supernatants determined by immunoassay. Supernatants containing antibody ranging from 0 to 30 ng of total antibody protein from each cell line was analyzed by non-reducing SDS-PAGE electrophoresis followed by Western Blot with anti-human kappa HRP conjugated antibody to detect CH2 domain deleted huCC49 Form A and Form B forms. Under these conditions, Form A migrates as a single 120 kDa homodimer and Form B as a 60 kDa doublet. Also visible are kappa chain monomer and dimers. Connecting peptides shown in SEQ ID NOs: 8, 9, 14, and 15 were all found to increase the proportion of form A produced. Exemplary results are shown in FIG. 3. These results show that both the G1/G3/Pro243Ala244Pro245+[Gly/Ser] (SEQ ID NO:9) (FIG. 3D) and G1/G3/Pro243+[Gly/Ser] (SEQ ID NO:8) (FIG. 3C) hinges resulted primarily if not entirely in the production of Form A CH2 domain-deleted huCC49 antibody with little or no detectable Form B. In contrast CH2 domain-deleted huCC49 Cys242Ser:Pro243 (SEQ ID NO:12) (FIG. 3A) and CH2 domain-deleted huCC49 Cys242Ser:Pro243Ala244Pro245 (SEQ ID NO:13) (FIG. 3B) resulted in a moderate to significant preference of the Form B form, respectively.

Figure 5:
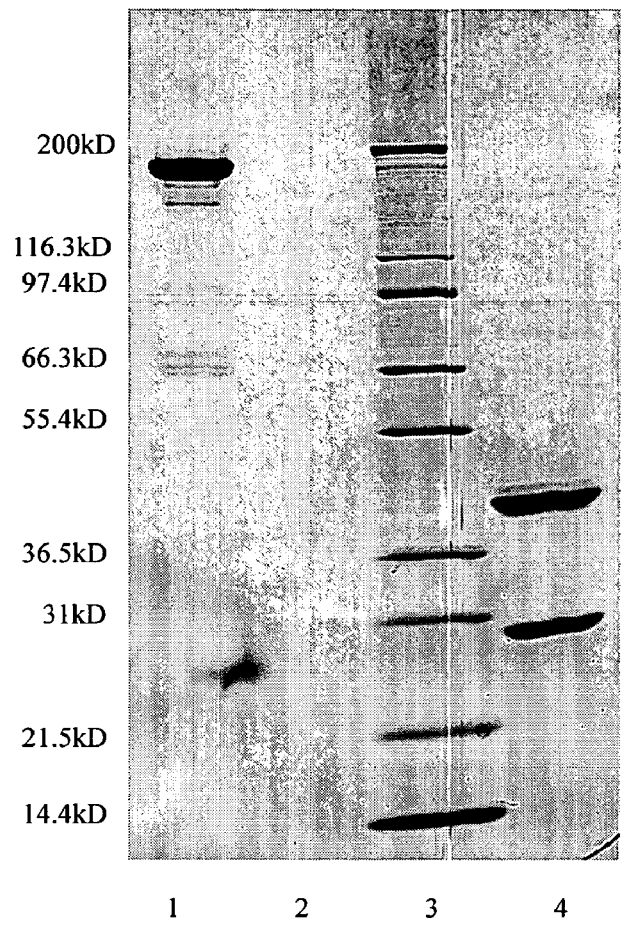
FIG. 5 shows SDS-PAGE gel of huCC49 G1/G3/PAP purified using only a Protein G column, showing that the antibody eluted essentially as a single peak at ≧96% purity without further HIC purification.
Figure 6:
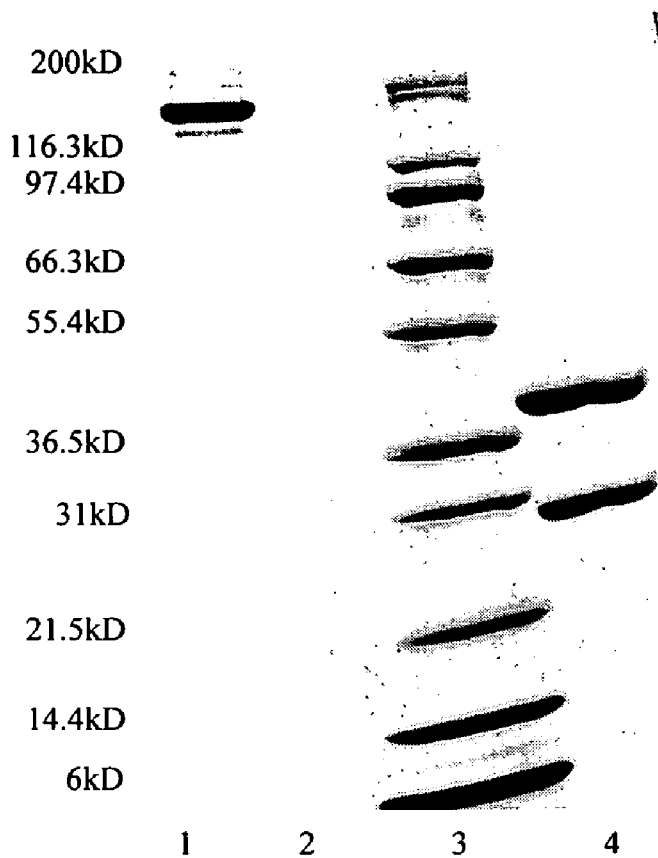
FIG. 6 shows SDS-PAGE gel of huCC49 V2 G1/G3/PAP purified using only a Protein G column, showing that the antibody eluted essentially as a single peak at ≧96% purity without further HIC purification.

Cell lines containing the Pro243Ala244Pro245+[Gly/Ser] (SEQ ID NO:14) and G1/G3/Pro243Ala244Pro245+[Gly/Ser] (SEQ ID NO:9) connecting peptides introduced into the huCC49 antibody sequence were used for antibody production. The Pro243Ala244Pro245+[Gly/Ser] and G1/G3/Pro243Ala244Pro245+[Gly/Ser] connecting peptides were also introduced into the huCC49 V2 antibody sequence and cell lines generated (The humanized CC49 version 2 sequence is described in Example 8; see FIGS. 19A and B for alignments of huCC49 and huCC49 V2 sequences for the light and heavy chains, respectively). Antibody was produced from CHO DG44 cells and purified using methods described in Example 4 below. Yields of the Form A isoform following the Protein G and HIC steps are reported in Table 3. From these results it is clear that the modifications introduced to the hinge region in the CH2 domain deleted antibodies led to the preferential synthesis of the A isoform. Following the HIC purification technique described in Example 4, purified HuCC49 Pro230Ala23 Pro232 and HuCC49 V2 Pro230Ala231Pro232 Form A material was achieved at values greater than 98%. HuCC49 G1/G3/Pro243Ala244Pro245 and HuCC49 V2 G1/G3/Pro243Ala244Pro245 Form A materials, purified using only the Protein G column, both eluted essentially as single peaks at ≧96% purity without further HIC purification (FIG. 5 and FIG. 6). All antibodies were examined by size exclusion chromatography and were found to elute as single peaks indicating that there was no significant aggregation or decomposition of antibody product.

Peptide mapping was used to determine the integrity of disulfide bond formation in the heavy chain hinge regions of CH2 domain deleted HuCC49, HuCC49 PAP, and HuCC49 G1/G3/PAP antibodies. Samples of the CH2 domain deleted CC49 antibodies were denatured, reduced and digested with trypsin as follows: aliquots of 150 ug were diluted to 100 ml in HPLC water and denatured in 6M guanidine hydrochloride, 50 mM Tris pH 8.0. The samples were reduced by the addition of 20 mM DTT and incubated for 30 minutes at 37° C. The reduced samples were alkylated with 50 mM iodoacetic acid for 30 minutes at 37° C. The alkylation reaction was quenched by the addition of excess DTT. The reduced and alkylated samples were buffer exchanged into 25 mM TRIS, 20 mM $CaCl_2$, pH 7.5 using PD-10 columns. Trypsin was added to each sample in a 1:15 (w/w) ratio and incubated for 4 hours at 37° C. The digestion was stopped by the addition of trifluoroacetic acid (TFA) to a final concentration of 0.1%. Trypsin digested samples (15 ug) were then analyzed according to chromatographic conditions described below.

Samples of the CH2 domain deleted CC49 antibodies were analyzed by endoproteinase Lys-C digestion. Denatured and reduced samples were prepared by adding a final concentration of 4 M guanidine HCl and 25 mM DTT to 1.5 mg/mL of sample. Non-reduced samples were prepared by adding a final concentration of 4 M guanidine HCl to 1.5 mg/mL of sample. Samples were incubated for 2 hours at 37° C. Digestion buffer (50 mM Tris, pH 7.0 and 0.062 AU/ml endoproteinase Lys-C) was then added to the samples at 1:1 (v/v) and samples were incubated for 15 hours at 37° C. At 15 hours, a second aliquot of enzyme (0.29 mAU: ug Antibody) was added and samples were incubated for an additional 6 hours at 37° C. To quench the reaction, TFA was added at 0.1% final concentration. Non-reduced and reduced endoproteinase Lys-C digested samples (12 ug) were then analyzed according to the procedure described below.

HPLC/mass spectrometry analysis. Samples were analyzed on an Agilent 1100 HPLC system connected to an Agilent MSD single quadrupole mass spectrometer. A reverse phase C18 column (Vydac catalog number 218TP52) was used with an eluant system of water/0.1% TFA (v/v) (Buffer A) and acetonitrile/0.1% TFA (v/v) (Buffer B), at a flow rate of 0.2 mL/minute. A post column "TFA fixative" solution of acetonitrile and acetic acid (1:1 v/v) at 0.1 mL/minute was added to enhance ionization. The column temperature was controlled at 45° C. and the elution profile was monitored at 215 and 280 nm. The total ion chromatogram was monitored in positive ion mode. Samples were injected onto the column and the gradient was held at 0% Buffer B for five minutes. Elution was accomplished with a linear gradient of 0 to 50% Buffer B over 125 minutes, followed by a 75% Buffer B wash over 10 minutes and a 0% Buffer B re-equilibration over 30 minutes.

In the endo Lys-C reduced analysis, fragment (L52-109) was undetected for all samples (FIG. 7B). This fragment is very hydrophobic and may have not eluted from the column matrix due to strong interactions. The corresponding tryptic fragment (L68-109) was also undetected in all samples (FIG. 7C). Since these fragments contain a large number of amino acids, the percent amino acid identity was lowered to ~89% identity. In addition, fragment (L68-119) was undetected in the endo Lys-C analysis of G1/G3/PAP bringing the identity down to ~79%.

The endo Lys-C non-reduced analysis provided much better results (FIG. 7A). Fragment (L52-109) was detected as a disulfide linkage with fragment (L1-24) in all samples. All other disulfide linkages were detected and the total % amino acid identity was ~99% for all samples. The G1/G3/PAP sample showed an additional heavy chain-heavy chain disulfide linkage in fragment (H232-275), below the original (H224-227) CPPC hinge region. The theoretical and observed mass values for the engineered hinge region peptides are shown in Table 4. The HuCC49ΔCH2 hinge endo Lys-C non-reduced peptide (residues H221-257) had an observed MW of 7419.4, in good agreement with the calculated mass of 7419.4 g/mol for a linked hinge containing two interchain disulfide bridges. The HuCC49ΔCH2 PAP hinge endo Lys-C non-reduced peptide (residues H221-260) had an observed MW of 7949.7 also in good agreement with the calculated mass of 7949.8 g/mol for a linked hinge containing two interchain disulfide bridges. Two hinge non-reduced peptide fragments resulted from digestion of HuCC49ΔCH2 G1/G3/PAP by endo Lys-C due to the presence of the lysine residue at Kabat position 241II in the 15 amino acid γ3 motif. Peptide fragments THTCPPCPEPK (residues H221-231) and SCDTPPPCPRCPAPGGGSSGGGSG-GQPREPQVYTLPPSRDELTK (residues H232-275) had observed MWs of 2414.3 and 8782.6 in excellent agreement with the calculated masses of 2413.0 and 8782.0 g/mol, respectively. The mass data supports the assertion that the THTCPPCPEPK peptide (residues H221-231) derived from HuCC49ΔCH2 G1/G3/PAP contains two interchain disulfide bridges. Importantly, the SCDTPPPCPRCPA-PGGGSSGGGSGGQPREPQVYTLPPSRDELTK peptide (residues H232-275) contains at least one interchain disulfide bridge consistent with the notion that the chimeric G1/G3/PAP hinge is participating in the formation of more than two disulfide bridges. These analyses show that HuCC49ΔCH2 PAP hinge forms two heavy chain interchain disulfide bonds. HuCC49ΔCH2 G1/G3/PAP hinge forms at least three heavy chain interchain disulfide bonds but possibly five. It is certain that fragment HuCC49ΔCH2 G1/G3/PAP residues H232-275 contains minimally one interchain disulfide bond, however it is not possible to discriminate mass differences in a hinge region containing three interchain disulfide bonds from one containing a single interchain and two intrachain disulfide bonds.

TABLE 3

The percentage of Form A antibody after affinity chromatography (Protein G) and after HIC purification

| CH2 domain deleted Antibody | % Form A Antibody | |
|---|---|---|
| | After Protein G | After HIC purification |
| HuCC49 (connecting peptide SEQ ID NO: 7) | 60 | 98 |
| HuCC49 PAP (connecting peptide SEQ ID NO: 14) | 83 | 98 |
| HuCC49 V2 PAP (connecting peptide SEQ ID NO: 14) | 90 | 99 |
| HuCC49 G1/G3/PAP (connecting peptide SEQ ID NO: 9) | 98 | Not done |
| HuCC49 V2 G1/G3/PAP (connecting peptide SEQ ID NO: 9) | 96 | Not done |

TABLE 4

Peptide mapping of engineered HuCC49ΔCH2 antibody hinge region peptides.

| Sample | Fragment # | A.A # | Theoretical MW | Theoretical Linked MW | Ob. Mass Reduced | Ob. Mass Non-reduced |
|---|---|---|---|---|---|---|
| HuCC49ΔCH2 | Endo Lys-C fragment 29 THTCPPCGGGSSGGGSGGQPREPQVYTLPPSRDELTK | (H221-257) | 3711.7 | 7419.4 | 3711.5 | 7419.1 |
| PAP | Endo Lys-C fragment 29 THTCPPCPAPGGGSSGGGSGGQPREPQVYTLPPSRDELTK | (H221-260) | 3976.9 | 7949.8 | 3976.8 | 7949.7 |

TABLE 4-continued

Peptide mapping of engineered HuCC49ΔCH2 antibody hinge region peptides.

| Sample | Fragment # | A.A # | Theoretical MW | Theoretical Linked MW | Ob. Mass Reduced | Ob. Mass Non-reduced |
|---|---|---|---|---|---|---|
| G1/G3:PAP | Endo Lys-C fragment 29 THTCPPCPEPK | (H221-231) | 1208.5 | 2413.0 | 1208.9 | 2414.3 |
|  | Endo Lys-C fragment 30 SCDTPPPCPRCPAPGGGSSGGGSGGQPREPQVYTLPPSRDELTK | (H232-275) | 4394.0 | 8782.0 | 4394.4 | 8782.6 |
| HuCC49ΔCH2 | Trypsin fragment 39 THTCPPCGGGSSGGGSGGQPR | (H221-241) | 1971.8 | NA | 1972.6 | NA |
| PAP | Trypsin fragment 39 THTCPPCPAPGGGSSGGGSGGQPR | (H221-244) | 2237.9 | NA | 2237.8 | NA |
| G1/G3:PAP | Trypsin fragment 39 THTCPPCPEPK | (H221-231) | 1324.5 | NA | 1325.1 | NA |
|  | Trypsin fragment 40 SCDTPPPCPR | (H232-241) | 1187.5 | NA | 1187.5 | NA |
|  | Trypsin fragment 41 CPAPGGGSSGGGSGGQPR | (H242-259) | 1542.6 | NA | 1542.9 | NA |

These data show that novel, engineered synthetic hinge region connecting peptides can be used to preferentially favor the formation of the A or B form. These studies also reveal the importance of the cysteine residues at position 242 (Kabat numbering system) in synthesizing the CH2 domain-deleted antibody Form A isoform. Accordingly, in one embodiment, a connecting peptide of the invention comprises a cysteine at at least one of position 239 or 242. Substituting the cysteine at either position 239 or 242 with serine (e.g., using connecting peptides shown in SEQ ID NOs:10, 11, 12, or 13) shifts CH2 domain-deleted antibody biosynthesis to the Form B form. The use of connecting peptides which increase the proportion of Form A produced will lead to a beneficial improvement in process, yield and/or stability. These synthetic hinge region connecting peptides are useful for favoring synthesis of CH2 domain deleted antibody Form A isoform for any antibody isotype, e.g., IgG1, IgG2, IgG3, or IgG4, based on the extremely high degree of homology among the CH3 domains for all four human isotypes. Including identical and conserved amino acid residues, IgG1 CH3 domain is 98.13% homologous to IgG2 CH3, 97.20% homologous to IgG3 CH3, and 96.26% homologous to IgG4 CH3.

Example 4

Purification of Form A and Form B from a Monoclonal Antibody Mixture Containing Both Isoforms 10 mL of ddCC49 supernatant was titrated with 1M Tris pH 9.0 to a final pH of 7.5. This material was filtered through a series of Sol-Vac 0.8μ and 0.4μ membranes. A 100 mL XK50 Protein G column was pre-equilibrated with 1×PBS at a flow rate of 80 ml/min. The titrated, filtered supernatant was loaded onto the column at 80 ml/min. Bound protein was washed with the equilibrium buffer for 2 column volumes and then eluted with 100 mM Glycine at pH 3.0. The fractions containing the ddCC49 peak were collected and immediately titrated with 1 M Tris pH 9.0 to a final pH of 7.0.

Figure 15:
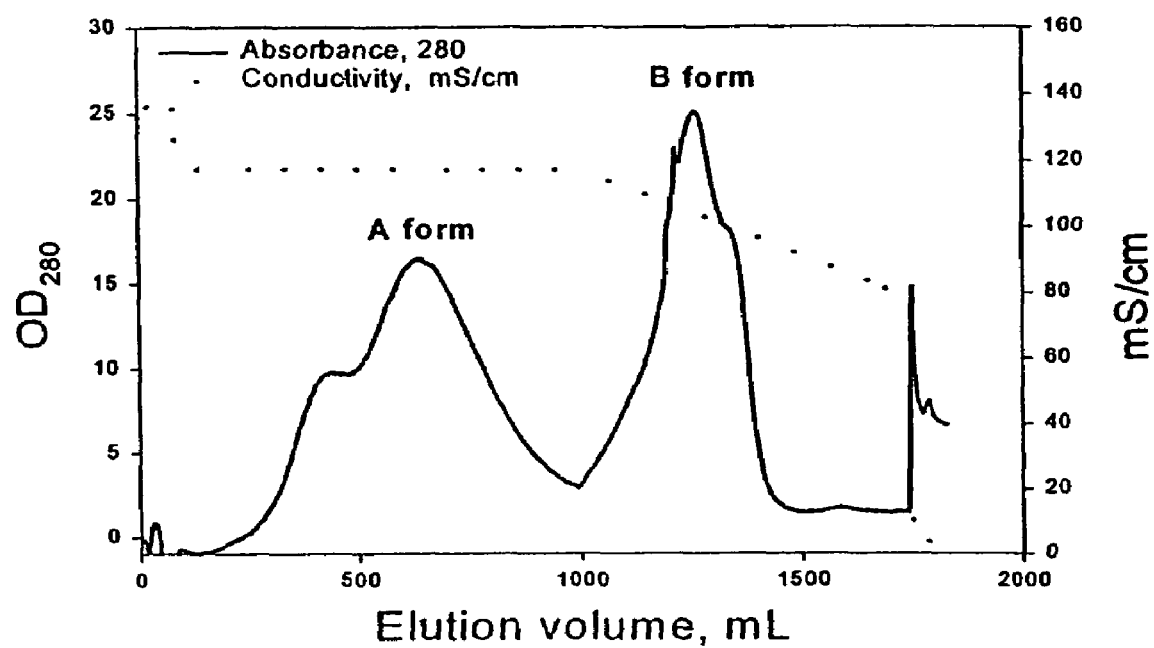
FIG. 15 shows a chromatogram of the HIC purification of CH2 domain-deleted huCC49 A and B forms.
Figure 16:
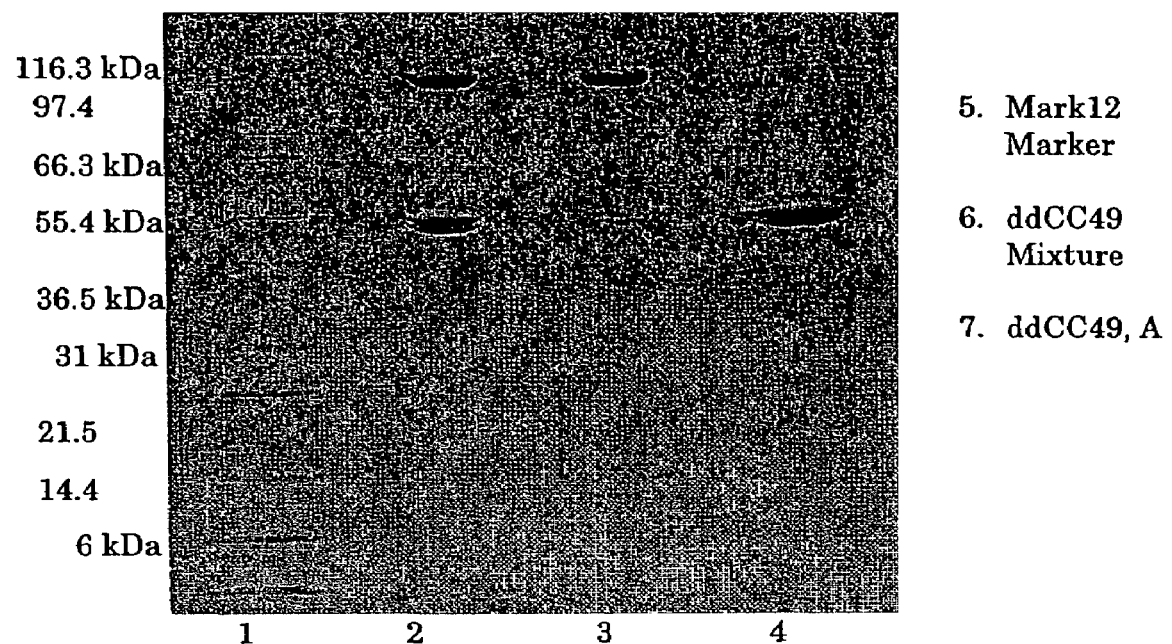
FIG. 16 shows purified CH2 domain-deleted huCC49 Forms A and B shown in lanes 3 and 4, respectively.

A Toso Biosep Phenyl 5PW-HR column was pre-equilibrated with 20 mM Phosphate pH 7.2; 1 M Ammonium Sulfate. The Protein G eluate was titrated to 1 M Ammonium Sulfate using a 3.5 M Ammonium Sulfate pH 7.2 stock and loaded at a concentration of 2 mg/ml of gel bed. Bound protein was washed with a 20 mM Phosphate pH 4 or 7.2 Ammonium Sulfate to adjust the conductivity to 116.4 mS/cm. The material eluted from this condition has an apparent molecular weight about 120 kD (Form A) on a non-reducing SDS-PAGE. The remaining bound antibody was further eluted with a linear gradient of reducing Ammonium Sulfate content in the Phosphate buffer. The latter eluted antibody apparently lacks the disulfide linkage between the heavy chains and its molecular weight is about 60 kDa (form B). FIG. 15 shows a chromatogram of the HIC purification. Purified A and B Forms are shown in lanes 3 and 4 of FIG. 16, respectively.

Both of the above purified materials can be recaptured by bringing the ammonium sulfate concentration to 1M and reloading it onto the cleaned Phenyl 5PW-HR column. Bound protein is eluted with 20 mM Phosphate pH 7.2 and dialyzed into 1×PBS.

Example 5

Comparison of Stability of Form A and Form B

The biologic activity of Forms A and B (as measured in preliminary experiments e.g., using direct binding or competition studies) revealed that Forms A and B have similar biologic activity.

The stability of Forms A and B was also compared. Purified ddCC49 molecules were concentrated to about 5 mg/ml by Amicon concentrator fitted with YM30 membrane (Millipore). The concentrated materials were equally divided into four portions for each isoforms and each fraction was put into 10K dialysis cassette (Pierce, cat#66410) for 16 h dialysis in the following buffers: 1) 10 mM Sodium Phosphate, pH3; 2) 10 mM Sodium acetate, pH 5; 3) 10 mM Sodium Phosphate, pH 7; and 4) 10 mM Sodium Borate, pH 9. After dialysis, the protein concentration of each solution was adjusted to 3 mg/ml. In addition to the pure A and B form solution, a portion of A and B solutions from each pH were mixed to create a mixture containing 50% each isoform. Total of 12 formulations were created (four pH levels times 3 antibody solutions). The solutions were filtered and filled in 3 ml Type-1 glass serum vials (West Pharmaceuticals) with gray butyl stopper.

Three temperatures, 2-8° C., 20-25° C., and 38-42° C. were chosen to store the protein solutions for stability testing. Prior to storage, 500 µl samples were drawn from each formulation for physical and chemical analyses, these zero-time point data were referred to as control. Once in storage, samples were drawn at the following schedule, 2 weeks, 1 month, 2 months and 3 months and submitted for testing immediately.

To evaluate the physical and chemical stability of the two isoforms, the following methods were used: turbidity measured at $OD_{320}$, non-reducing SDS-PAGE, and size-exclusion chromatography.

Non-reducing SDS-PAGE was performed on for samples stored at 2-8° C., 20-25° C. and 38-42° C. for various time points. Both A and B form are relatively stable at pH 5 when stored at 2-8° C. However, when formulated at pH 7 and 9, both A and B forms showed degradation as indicated by increasing in number of bands that were smaller than the original major bands (120 kDa for form A and 60 kDa for form B). It was noticed that, particularly for pH 7 and 9 samples stored at low and intermediate temperatures, the intensity and number of bands that were less than 55 kDa were higher in B-isoform than A. This indicated that under these conditions the A-isoform is more stable than B-isoform. However, this seems not to be the case for A-isoform in pH 5 and stored at 20-25° C. This sample seemed to have more fragments than B-isoform. This appears to have been an artifact due to microbial contamination (discussed in more detail below). At high storage temperature, both forms at pH 9 were significantly degraded and there was almost no difference in gel patterns among the samples. Under this condition, trace amount of smear bands showed up at top of the gel which indicated the formation of aggregates. Because aggregates could be dissolved by SDS, the aggregation was investigated using the methods described in the following sections.

Table 5A through Table 5C list the turbidity data for ddCC49 stored at three different temperatures. The turbidity measures both the soluble and non-soluble aggregates and it is based on the amount of light scattered by these particles. When present, aggregates will scatter light and result in an increase in $A_{320}$. As showed in Table 5A-C, the turbidity of ddCC49 molecules stored at 2-8° C. increases as pH increased for both A and B isoforms, with the former being less turbid than the latter. This trend held true for samples stored for less than a month at higher temperatures (20-25° C. and 38-40° C.). As storage time reached 3 months, the turbidity increased significantly for samples at high pH and temperature, and the difference between A and B forms diminished. These results parallel those of SDS-PAGE and indicate that both isoforms are relatively stable (in terms of not forming aggregates) at pH 3 and 5, and that A-isoform is less susceptible to aggregation than the B form.

TABLE 5A

Turbidity measured at $A_{320}$ for ddCC49 samples stored at 2-8° C.

| Time | A-isoform | | | | B-isoform | | | | Mixture | | | |
|---|---|---|---|---|---|---|---|---|---|---|---|---|
| (month) | pH = 3 | 5 | 7 | 9 | 3 | 5 | 7 | 9 | 3 | 5 | 7 | 9 |
| 0 | 0.030 | 0.038 | 0.044 | 0.056 | 0.034 | 0.042 | 0.046 | 0.066 | 0.036 | 0.042 | 0.051 | 0.061 |
| ½ | 0.029 | 0.029 | 0.046 | 0.045 | 0.030 | 0.038 | 0.048 | 0.058 | 0.034 | 0.033 | 0.043 | 0.055 |
| 1 | 0.033 | 0.039 | 0.035 | 0.055 | 0.033 | 0.035 | 0.044 | 0.059 | 0.032 | 0.040 | 0.039 | 0.066 |
| 2 | 0.042 | 0.022 | 0.042 | 0.044 | 0.039 | 0.037 | 0.055 | 0.067 | 0.042 | 0.024 | 0.040 | 0.058 |
| 3 | 0.035 | 0.047 | 0.051 | 0.050 | 0.038 | 0.041 | 0.066 | 0.081 | 0.027 | 0.048 | 0.051 | 0.065 |

TABLE 5B

Turbidity measured at $A_{320}$ for ddCC49 samples stored at 20-25° C.

| Time | A-isoform | | | | B-isoform | | | | Mixture | | | |
|---|---|---|---|---|---|---|---|---|---|---|---|---|
| (month) | pH = 3 | 5 | 7 | 9 | 3 | 5 | 7 | 9 | 3 | 5 | 7 | 9 |
| ½ | 0.031 | 0.032 | 0.056 | 0.066 | 0.039 | 0.034 | 0.064 | 0.083 | 0.034 | 0.039 | 0.060 | 0.071 |
| 1 | 0.025 | 0.043 | 0.055 | 0.090 | 0.034 | 0.042 | 0.070 | 0.084 | 0.028 | 0.039 | 0.055 | 0.094 |
| 2 | 0.034 | 0.053 | 0.077 | 0.113 | 0.046 | 0.032 | 0.090 | 0.087 | 0.037 | 0.038 | 0.066 | 0.108 |
| 3 | 0.036 | 0.056 | 0.156 | 0.143 | 0.029 | 0.060 | 0.121 | 0.125 | 0.044 | 0.050 | 0.101 | 0.142 |

TABLE 5C

Turbidity measured at $A_{320}$ for ddCC49 samples stored at 38-42° C.

| Time | A-isoform | | | | B-isoform | | | | Mixture | | | |
|---|---|---|---|---|---|---|---|---|---|---|---|---|
| (month) | pH = 3 | 5 | 7 | 9 | 3 | 5 | 7 | 9 | 3 | 5 | 7 | 9 |
| ½ | 0.041 | 0.042 | 0.068 | 0.063 | 0.041 | 0.044 | 0.080 | 0.067 | 0.041 | 0.039 | 0.070 | 0.064 |
| 1 | 0.041 | 0.043 | 0.071 | 0.065 | 0.036 | 0.040 | 0.079 | 0.069 | 0.032 | 0.048 | 0.078 | 0.070 |
| 2 | 0.047 | 0.030 | 0.066 | 0.060 | 0.046 | 0.045 | 0.087 | 0.082 | 0.051 | 0.034 | 0.078 | 0.079 |
| 3 | 0.058 | 0.051 | 0.098 | 0.105 | 0.046 | 0.057 | 0.101 | 0.157 | 0.056 | 0.057 | 0.101 | 0.126 |

Size exclusion chromatography (SEC) is a powerful method for revealing the percent of intact molecules and the degraded products (both fragments and soluble aggregates) and is highly reproducible. In Table 5A-C the percent of intact monomer of A-isoform, B-isoform and the mixture stored at different temperatures are listed. For samples stored at 2-8° C., it is clear that Form A has a higher percentage of monomer as compared to Form B, and the mixture of Form A and Form B was somewhere in between. At this storage temperature, both forms were relatively stable at pH 3, 5 and 7 (with pH 5 being the most stable condition) for about three months. However, at pH 9 there was a significant decrease in percentage of monomer for Form B but only a slight decrease for Form A. At elevated temperatures, all samples showed a significant decrease in percent of monomer as storage time increased; the A-isoform outperformed the B-isoform. However there was an exception, the sample of A-isoform in pH 5 stored at room temperature exhibited much more degradation than the B-isoform or the mixture under similar storage conditions. A close examination of this particular A-isoform vial, the data from SDS-PAGE, and SEC of the sample suggested that microbial contamination might have caused this unexpected result. First, both the SEC and SDS-PAGE results indicated that the degradation for this sample was primarily accounted for by a increase in fragmentation, presumably resulting from microbial digestion, otherwise some degree of increase in aggregation would have been expected. Second, the fact that the mixture sample, which contained 50% each of A and B-isoform, showed a better stability profile than B-isoform indicating that a more stable A-isoform must have contributed to the higher percent of monomer. Finally, A-isoform in pH 5 stored at 2-8° C. and 38-42° C. both showed higher percent of monomer than B-isoform under similar conditions. Therefore, intermediate storage temperature should have yielded similar results. Due to the limited amount of sample, an assay for microbial contamination could not be performed.

It was also noted that for both isoforms of IDEC-159 stored in high pH (9) and at 40° C., the percent of monomer reduced to about 30%. Under these severe conditions, the stability differences between the two isoforms disappeared. This SEC result mirrors of the results found using SDS-PAGE. Both results indicate that, although some chemical and physical characteristics differ between the two isoforms, the mechanism and by-products of degradation for both isoforms are similar, if not identical.

In summary, the SEC results indicate that both A and B-isoforms have optimal pH at about 5, and that A-isoform is more stable than B-isoform in terms of retaining higher percent of intact monomer at similar storage conditions.

TABLE 6A

Percent of monomer for ddCC49 samples stored at 2-8° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| 0 | 98.81 | 99.13 | 98.16 | 97.93 | 97.02 | 97.70 | 96.88 | 93.51 | 97.83 | 98.27 | 97.44 | 95.81 |
| ½ | 98.98 | 99.16 | 98.25 | 98.00 | 97.15 | 97.87 | 96.96 | 91.95 | 98.15 | 98.49 | 97.68 | 95.59 |
| 1 | 98.80 | 99.20 | 97.99 | 97.11 | 97.02 | 97.81 | 96.62 | 88.99 | 98.04 | 98.45 | 97.41 | 94.45 |
| 2 | 98.74 | 99.01 | 98.00 | 95.67 | 97.15 | 97.69 | 95.50 | 84.84 | 98.06 | 98.34 | 96.81 | 92.17 |
| 3 | 98.28 | 98.89 | 97.88 | 95.31 | 96.69 | 98.14 | 95.37 | 85.98 | 97.61 | 98.15 | 96.65 | 89.90 |

TABLE 6B

Percent of monomer for ddCC49 samples stored at 20-25° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| ½ | 97.83 | 99.04 | 97.12 | 93.65 | 95.84 | 97.62 | 93.71 | 79.61 | 96.75 | 98.30 | 95.37 | 87.67 |
| 1 | 96.60 | 96.63 | 95.65 | 88.09 | 94.38 | 97.23 | 90.69 | 72.26 | 95.36 | 97.99 | 93.05 | 80.92 |
| 2 | 93.62 | 92.79 | 93.17 | 80.06 | 91.71 | 96.96 | 85.51 | 66.53 | 92.78 | 97.51 | 89.33 | 73.91 |
| 3 | 92.81 | 89.56 | x | 74.31 | 89.30 | 96.04 | 82.57 | 63.25 | 90.46 | 97.02 | 86.80 | 69.36 |

TABLE 6C

Percent of monomer for ddCC49 samples stored at 38-42° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| ½ | 86.31 | 97.50 | 85.06 | 66.42 | 79.85 | 94.29 | 69.68 | 63.64 | 82.09 | 95.70 | 76.24 | 63.95 |
| 1 | 78.71 | 95.19 | 73.77 | 51.55 | 66.73 | 89.37 | 54.70 | 50.10 | 68.53 | 92.02 | 62.93 | 49.28 |
| 2 | 66.64 | 91.63 | 60.45 | 38.43 | 60.29 | 81.08 | 42.98 | 37.09 | 61.33 | 85.81 | 51.08 | 36.68 |
| 3 | 57.87 | 86.99 | 52.82 | 30.81 | 43.61 | 74.23 | 36.68 | 29.73 | 46.75 | 80.93 | 44.35 | 30.18 |

Example 7

Preparative Purification of Forms A and B

IDEC-159 (ddCC49) is a CH2 domain deleted monoclonal antibody directed against TAG-72 antigen, which is expressed on the surface of tumors. IDEC-159 contains two isoforms of the antibody, called Form A and Form B. The current cell culture process for IDEC-159 produces an approximate 50:50 ratio of Form A to Form B. The form A isoform is an antibody with a deleted CH2 region in the Fc portion of the heavy chain. In addition to having a deleted CH2 region, Form B also lacks the disulfide bond linkage across the Fc region and is only held together by hydrophobic interactions and salt bridges.

The third and final chromatography step in the IDEC-159 purification process was developed to separate the two isoforms of IDEC-159. The separation is achieved by hydrophobic interaction chromatography (HIC), using a Phenyl TSK-gel 5PW-HR adsorbent. Since Form B is more hydrophobic than Form A, it adsorbs irreversibly to the stationary phase using approximately 0.73 M Ammonium Sulfate/20 mM Sodium Phosphate, pH 4.0-pH 7.0 as the mobile phase. Form A binds to a lesser extent to the stationary phase under these conditions and is therefore eluted isocratically, i.e. it leaves the column with the flowthrough fraction. Subsequent to the isocratic elution of Form A, omitting Ammonium sulfate from the mobile phase desorbs Form B. The following method was used to separate the two isoforms of IDEC-159:

- The column was sanitized using ≧3 CVs of 0.5 N NaOH, at ≦150 cm/hr.
- The column was equilibrated using ≧5 CVs of 0.73 M Ammonium Sulfate/20 mM Sodium Phosphate, pH 4.0, at ≦150 cm/hr.
- The column was loaded with room temperature TMAE Flowthrough that has been adjusted to include 0.43 volumes of 2.5 M Ammonium Sulfate/20 mM Sodium Phosphate, pH 4.0 liquid stock solution, at 5 mg per ml of resin. The antibody was loaded onto the column at pH 4.0, at ≦100 cm/hr. Collection of the antibody started when the outlet O.D. at 280 nm reaches 10 mAU.
- The column was washed using 15 CVs of 0.73 M Ammonium Sulfate/20 mM Sodium Phosphate, pH 4.0, at ≦100 cm/hr. Continue antibody collection throughout the 15 CV wash, then the outlet was diverted back to waste.
- The column was stripped using ≧5 CVs of 20 mM Sodium Phosphate, pH 4.0, at ≦100 cm/hr. 6. The column was cleaned with ≧3 CVs 0.5 N NaOH, at ≦150 cm/hr.
- The column was equilibrated with ≧3 CVs of 0.73 M Ammonium Sulfate/20 mM Sodium Phosphate, pH 4.0, at ≦150 cm/hr.
- The column was stored in ≧3 CVs of 20% Ethanol, at ≧150 cm/hr.

The separation of the two forms at a preparative scale (5 L column volume, total IDEC-159 load approximately 20 g) is shown in FIG. 17 (Panels A and B). The first two peaks comprise the isocratic elution of Form A, the second peak shows the eluted Form B, while the third peak contains impurities, which are removed from the stationary phase during cleaning.

Figure 18:
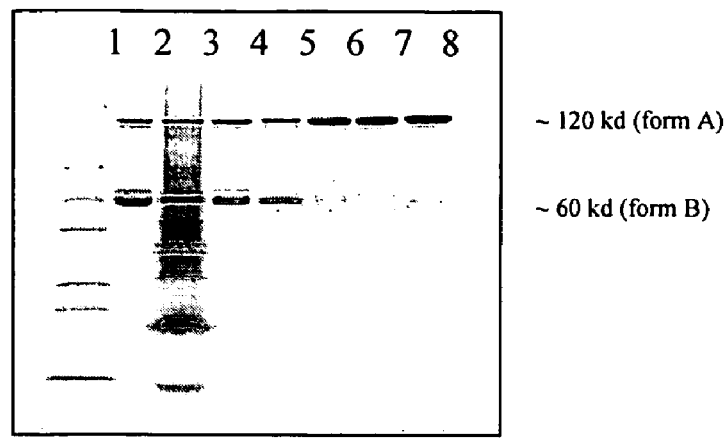
FIG. 18 shows that the CH2 domain-deleted huCC49 fractions eluted isocratically using 0.73 M Ammonium Sulfate/20 mM Sodium Phosphate, pH 4.0 (lanes 6 to 8) contain predominantly Form A (purity>90%).

The capability of this method to separate Forms A and B at preparative scale was also demonstrated by SDS PAGE. As shown in FIG. 18, the fractions eluted isocratically using 0.73 M Ammonium Sulfate/20 mM Sodium Phosphate, pH 4.0 (lanes 6 to 8) contain predominantly Form A (purity >90%).

Example 8

Humanization of Monoclonal Antibody CC49

Several changes to the CC49 antibody were made to create a humanized CC49 version 2 (huCC49 V2). FIG. 19 shows an alignment of the light (FIG. 19A) and heavy chain (FIG. 19B) variable regions of murine CC49, LEN or 21/28' CL, humanized CC49, and humanized CC49 V2 (which comprises one amino acid substitution in the light chain and two amino acid substitutions in the heavy chain as compared to humanized CC49, see underlined amino acids). To further reduce potential immunogenicity of the humanized CC49 MAb, murine residues present in the antibody were examined and considered for replacement with human framework residues derived from human acceptor sequences LEN for light chain substitutions and 21/28' CL for heavy chain substitutions. (Singer I I et al., 1993. Optimal Humanization of 1B4, an Anti-CD18 Murine Monoclonal Antibody, is Achieved by Correct Choice of Human V-Region Framework Sequences. J. Immunol. 150: 2844-2857. Padlan E A, 1991. Possible Procedure For Reducing the Immunogenicity of Antibody Variable Domains While Preserving Their Ligand-Binding Properties. Molecular Immunol. 28:489-498). Framework residues considered to be important for preserving the specificity and affinity of the combining site revealed only a few differences. In the heavy chain sequence, the predicted buried residues at positions 69 (leucine) and 93 (threonine) were both substituted with the human residues isoleucine and alanine, respectively. In the light chain sequence, one residue predicted to be mostly buried at position 43 (serine) was substituted with the human residue proline.

Domain deleted forms of the V2 CC49 antibody were made and connecting peptides were inserted into the huCC49 V2 sequence. FIG. 13A (SEQ ID NO: 28) shows the DNA sequence of heavy chain CH2 domain-deleted huCC49 V2 containing G1/G3/Pro243Ala244Pro245+[Gly/Ser] hinge connecting peptide. FIG. 13B (SEQ ID NO: 29) shows the DNA sequence of light chain CH2 domain-deleted huCC49 V2. FIG. 14A (SEQ ID NO: 30) shows the amino acid sequence of heavy chain CH2 domain-deleted huCC49 V2 containing G1/G3/Pro243Ala244Pro245+[Gly/Ser] hinge connecting peptide. FIG. 14B (SEQ ID NO: 31) shows the amino acid sequence of light chain CH2 domain-deleted huCC49 V2.

Example 9

Figure 20:
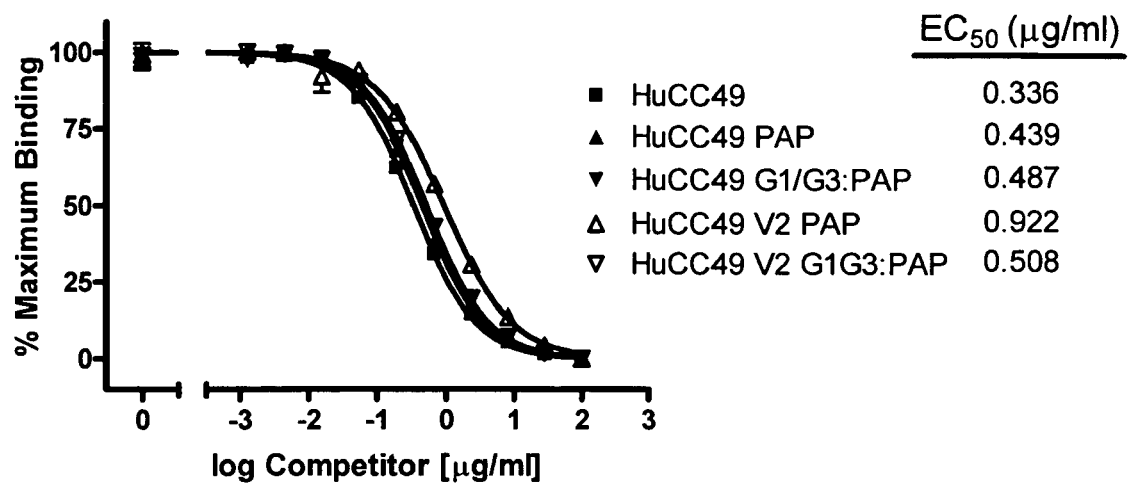
FIG. 20 shows the results of a competitive binding assay to bovine submaxillary mucine, a source of the TAG-72 antigen, by time-resolved fluorometric immunoassay.

Enhanced Biodistribution Profiles of Antibodies Comprising Novel Connecting Peptides Various forms of domain deleted antibodies (with and without connecting peptides) were tested in a competitive binding assay for their ability to bind to bovine submaxillary mucine, a source of the TAG-72 antigen, by time-resolved flourometric immunoassay using a Wallac 1420 Multilabel Counter Victor V (PerkinElmer). Competitive binding curves are shown in FIG. 20. HuCC49 PAP (containing the connecting peptide shown in SEQ ID NO: 14), HuCC49 V2 PAP (containing the connecting peptide shown in SEQ ID NO: 14), HuCC49 G1/G3:PAP (containing the connecting peptide shown in SEQ ID NO: 9), HuCC49 V2 G1/G3/PAP (containing the connecting peptide shown in SEQ ID NO: 9), and control parent HuCC49 antibodies were evaluated. Relative binding activities for all three hinge engineered antibodies are indistinguishable or within 2-3-fold of the control parent CC49 antibody.

Biodistribution of $^{90}$Y-2-(p-isothiocyanatobenzyl) (p-SCN-Bz)-cyclohexyldiethylenetriaminepentaacetic acid ligand (CHx-DTPA) conjugated HuCC49 V2 PAP (containing the connecting peptide shown in SEQ ID NO: 14) and control parent HuCC49 antibody were evaluated and compared in athymic mice bearing LS-174T human tumor xenografts. Percentage injected dose (% ID) of $^{90}$Y radiolabelled antibody per gram of tumor or normal tissue was determined at 3 and 24 hours and is shown in Table 7.

TABLE 7

7 mice/group

|  | Blood | Spleen | Kidney | Liver | Tumor |
|---|---|---|---|---|---|
| HuCC49 | | | | | |
| 3 hrs | 20.1 ± 3.5 | 6.1 ± 1.6 | 11.7 ± 1.7 | 10.1 ± 1.8 | 9.3 ± 2.0 |
| 24 hrs | 0.7 ± 0.2 | 9.5 ± 4.0 | 11.0 ± 2.0 | 12.0 ± 1.5 | 12.7 ± 7.1 |
| HuCC49 V2 PAP | | | | | |
| 3 hrs | 24.6 ± 3.0 | 4.6 ± 2.2 | 10.0 ± 1.4 | 8.4 ± 1.0 | 16.1 ± 5.0 |
| 24 hrs | 2.0 ± 0.6 | 7.7 ± 1.8 | 6.7 ± 0.4** | 11.2 ± 2.2 | 21.3 ± 4.8* |

Figure 21:
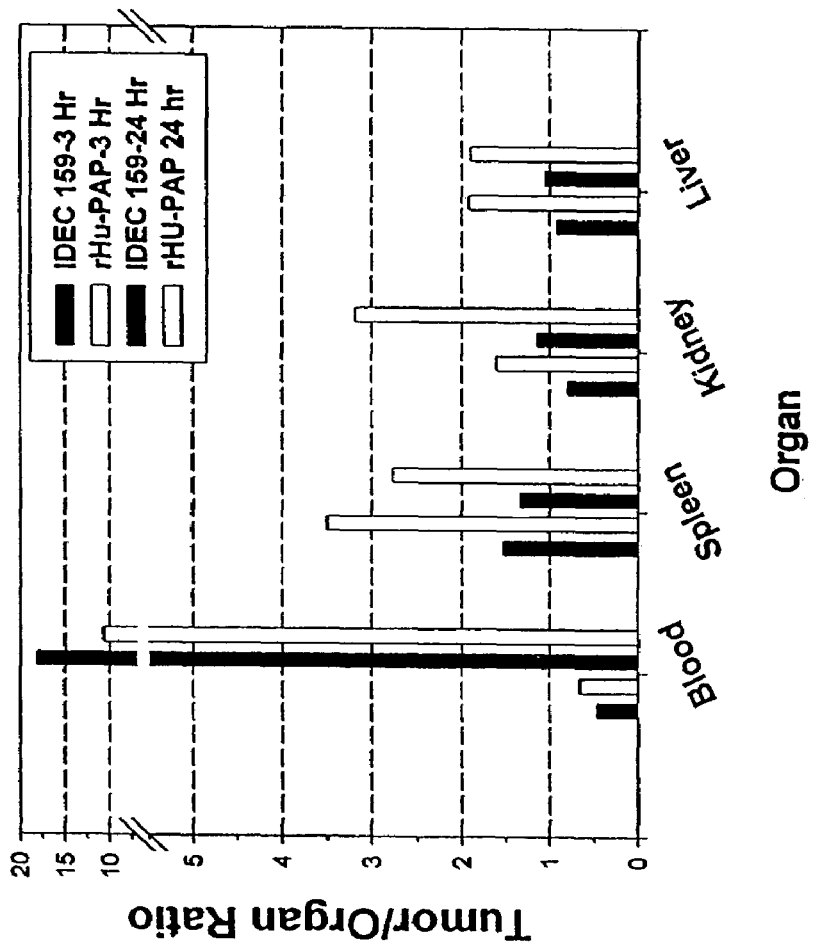
FIG. 21 shows the tumor to organ ratio comparing $^{90}$Y/CHx-DTPA conjugated domain deleted CC49 constructs in LS174T tumor xenografts.

Data represent mean values +/− standard deviations.
*p < 0.05 unpaired t test compared to 24 hr time point HuCC49 in tumor
**p < 0.001 unpaired t test compared to 24 hr time point HuCC49 in kidney Surprisingly, at the 24 hour time point HuCC49 V2 PAP uptake was significantly higher in the tumor (p<0.05 unpaired t Test) and, conversely, lower in the kidney (p<0.01) than control HuCC49 antibody. When the tumor to organ ratio for these antibodies was compared, the HuCC49 V2 PAP resulted in a higher tumor to organ ratio for all organs except blood (FIG. 21).

These results suggest that these novel hinges impart structural changes to antibodies that positively effect tumor localization and decrease uptake by normal organs, such as the kidney. Thus, these novel hinges are particularly useful when incorporated into therapeutic antibodies.

Example 10

Enhanced Biodistribution Profiles of Antibodies Comprising Novel Connecting Peptides: Detailed Time Course This example confirms and extends the results presented in Example 9. The antibodies Human CC49 V2 G1/G3/Pro243Ala244Pro245+[Gly/Ser] (SEQ ID NO: 9) and HuCC49 (gly/ser) were diafiltered and concentrated into low metal 5 mM sodium acetate buffer, pH 5 (LMB) using a pre-rinsed Amicon Centricon 30. Centrifugation of the centricon was performed in a fixed angle rotor at 5000×g held at a temperature of 2-8° C. Each antibody was recovered by adding 50 ill of LMB to the sample reservoir, vortexing briefly, and back-spinning for 10 minutes at 1000×g. The protein concentration was determined using UV Spec analysis at 280 nm using the extinction coefficient of 1.48. Each antibody was then adjusted down to 10.5 mg/ml using LMB.

The antibodies were adjusted to ~pH 8.6 using 1.0 M Boric Acid (pH 8.6, Chelex treated and 0.2 μm filtered). CHx-DTPA (dissolved in 1.0 M Boric Acid) was then added at a molar ratio of 3 chelates to 1 mole of antibody. The amount of Boric acid added was one-tenth the antibody volume. This mixture was then vortexed and incubated for 16 to 18 hours at room temperature. The reaction was stopped by adding the mixture to a new, pre-rinsed Centricon 30 and diafiltered into low metal 5 mM Sodium Acetate, 150 mM Sodium Chloride, pH 5 as per the previous diafiltration. The concentration of each antibody was adjusted to 3 mg/mL.

Female nude mice were inoculated s.c. with LS174T cells suspended in HBSS (Biowhittaker, Cat#10-547F) on the inside of the right thigh. Tumor sizes were measured one day prior to study start. Tumor volumes were calculated by multiplying the length times half of the squared width [L×((W$^2$)/2)]. The mice were grouped to give an average tumor volume of ~200 mm3.

Forty two nude mice were injected with $^{111}$In-labeled CH2 domain deleted antibody at time zero. The study tracked the distribution of the antibody over the course of seven timepoints with each timepoint consisting of six mice. Urine was collected from each mouse by holding the mouse over tared weigh paper and squeezing the bladder. Blood was taken via "eye bleed" (approximately 200 ul per mouse). For each individual mouse, any feces excreted during the blood and urine sampling was collected. Following the blood collection, the mice were sacrificed by cervical dislocation. Once each of the six mice had been sacrificed the other samples were collected via dissection. Each sample (except for the skin) was rinsed with 3% formalin, blotted dry on paper towel and then weighed. All samples were weighed using tared weigh paper.

Figure 22:
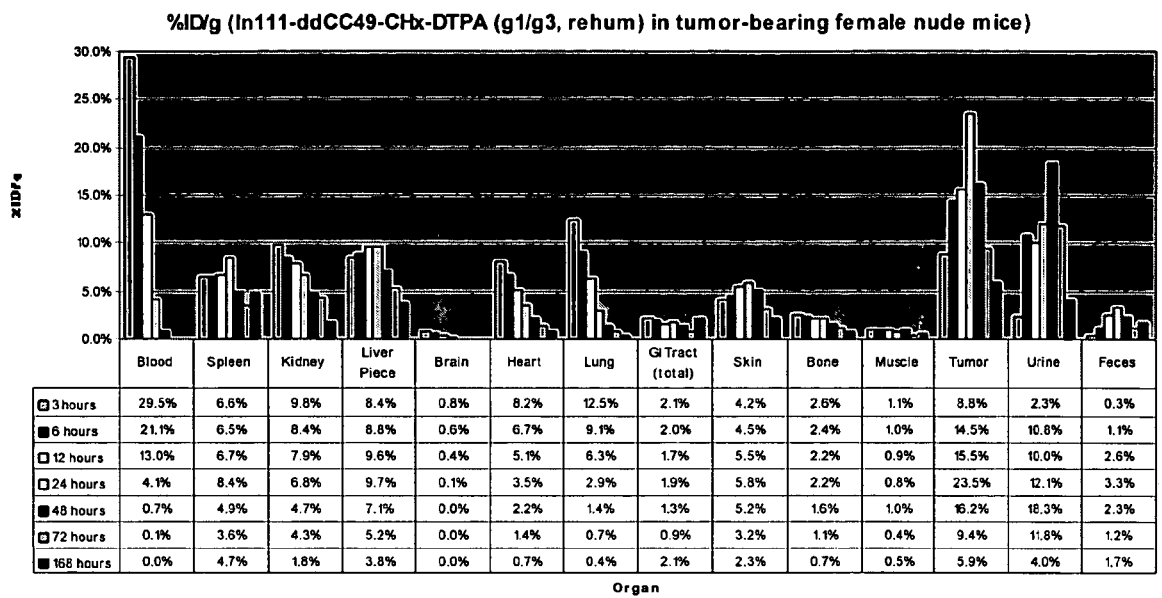
FIG. 22 shows the biodistribution of Human CC49 V2 comprising the G1/G3/Pro243Ala244Pro245+[Gly/Ser] connecting peptide.
Figure 23:
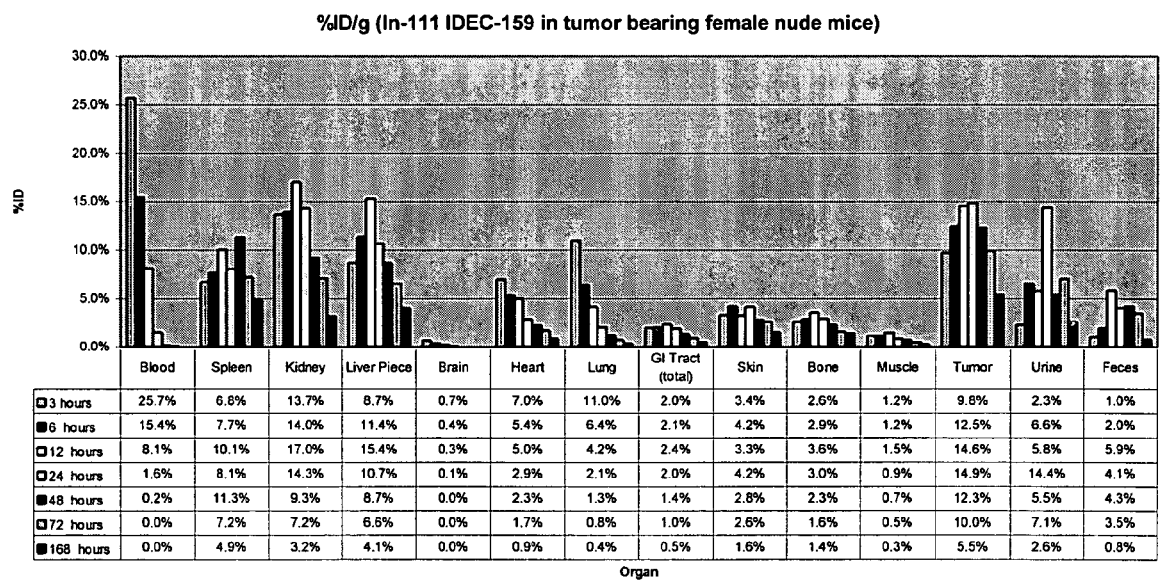
FIG. 23 shows the biodistribution of HuCC49 [gly/ser].

Following the sample collections, the samples were placed into borosilicate test tubes and counted on a gamma counter along with a decay control consisting of a 1:10 dilution of the labeled antibody. The percent radioactivity associated with each organ or tissue relative to the decay control (% injected dose/g tissue or organ) was calculated and those values are presented in the FIG. 22 (CC49 V2 G1/G3/Pro243Ala244Pro245+[Gly/Ser]) and 23 (HuCC49 [gly/ser]). The example shows that antibody molecules comprising this novel connecting peptide show decreased accumulation in the kidney, slightly increased accumulation in the blood and significantly increased accululation at tumor. This profile is consistent with these molecules having increased stability in vivo and enhanced efficacy and safety.

Example 11

Antibodies Comprising Connecting Peptides Have Decreased Sensitivity to Reducing Agents The example demonstrates that domain deleted CC49 G1/G3/Pro243Ala244Pro245+[Gly/Ser] (SEQ ID NO: 9) appears more stable toward glutathione (GSH) reduction, as is parent CC49, than domain deleted CC49 with a Gly-Ser hinge linker.

Briefly, 50 ug of ddCC49 (Gly-Ser), ddCC49 G1/G3/Pro243Ala244Pro245+[Gly/Ser] (SEQ ID NO: 9) or parent CC49 were incubated with 0, 1, 5 or 10 mM GSH for one hour at room temperature. Reaction buffers used include 100 mM PBS, pH 7.2 or 100 mM Sodium Acetate, 100 mM NaCl, pH 4.5. GSH-treated antibodies were heated with SDS and applied to a 4-20% gradient SDS-PAGE, non-reducing gel. Applied samples were allowed to migrate through the gel at a constant 120 Volts for 90 minutes at room temperature. Proteins were Coomassie stained and gels dried. Gels are shown in FIG. 24.

Figure 24:
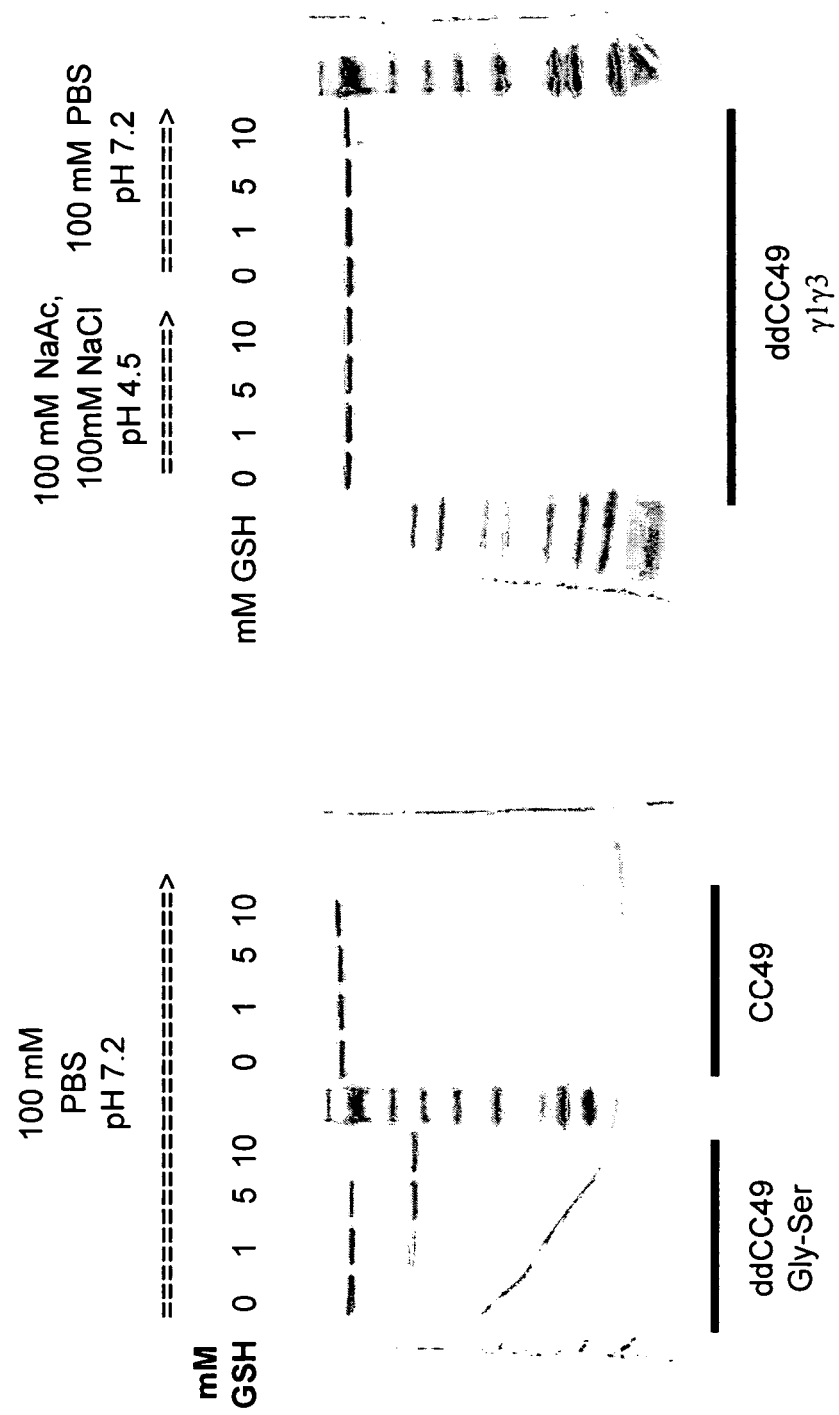
FIG. 24 shows that domain deleted CC49 G1/G3/Pro243Ala244Pro245+[Gly/Ser] (SEQ ID NO: 9) appears more stable toward glutathione (GSH) reduction, as is parent CC49, than domain deleted CC49 with a Gly-Ser hinge linker.

As shown in FIG. 24, domain deleted CC49 G1/G3/Pro243Ala244Pro245+[Gly/Ser] (SEQ ID NO: 9) appears more stable toward glutathione (GSH) reduction, as is parent CC49, than domain deleted CC49 with a Gly-Ser hinge linker. In addition, 100 mM Sodium Acetate at pH 4.5 further protects domain deleted CC49 G1/G3/Pro243Ala244Pro245+[Gly/Ser] (SEQ ID NO: 9) from GSH reduction compared to 100 mM PBS at pH 7.2. This unexpected observation of decreased sensitivity to reducing agents suggests that the G1/G3/Pro243Ala244Pro245+[Gly/Ser] (SEQ ID NO: 9) hinge design enables the use of chemistries using reducing agents, such as those used to prepare drug conjugates (e.g. SPDP linkers) or techniques for attaching radioisotopes to antibodies (eg. $^{99M}$Tc), while maintaining the physical integrity of the antibody. This advantage with respect to reducing agent sensitivity does not appear to alter pharmacokinetic advantages of CH2-domain deleted constructs (see mouse biodistribution data in Example 10). The decreased sensitivity to reducing agents also may be predictive of increased in vivo stability.

Example 12

Anti-CD20 Antibody Comprising a Connecting Peptide

The hinge region connecting peptide G1/G3/Pro243Ala244Pro245+[Gly/Ser] (SEQ ID NO: 9) was introduced into a CH2 domain-deleted C2B8 antibody as described in Example 3. C2B8 is a chimeric anti-CD20 monoclonal antibody consisting of murine heavy and light chain variable domains fused to human heavy and light chain constant domains, respectively. Correct modifications to the hinge region were confirmed by DNA sequence analysis. Plasmid DNA was used to transform CHO DG44 cells for transient production of antibody protein.

Figure 27:
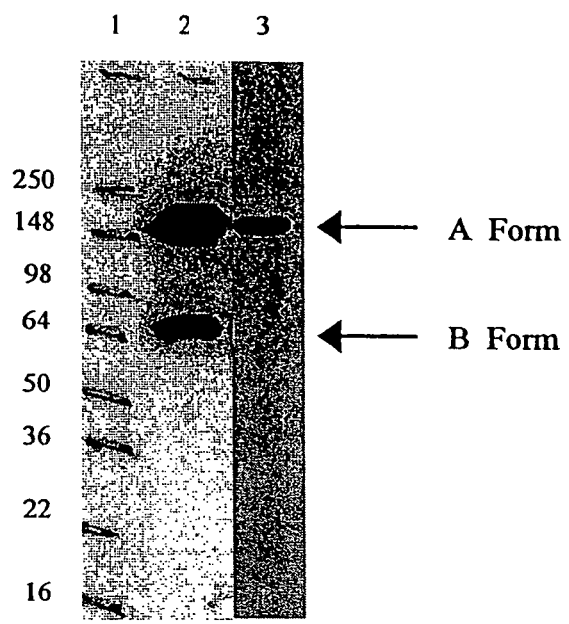
FIG. 27 shows that the inclusion of the G1/G3/Pro243Ala244Pro245+[Gly/Ser] connecting peptide (SEQ ID NO:9) into an antibody of different specificity (here the CH2 domain-deleted C2B8 antibody) results in the production of essentially all form A antibody with little or no detectable Form B (lane 3).

Supernatant was collected from cells producing CH2 domain-deleted C2B8 antibody containing the G1/G3/Pro243Ala244Pro245+[Gly/Ser] connecting peptide and concentration of antibody in the culture supernatants determined by immunoassay. Approximately 3 ng of total antibody protein from the transient cell culture was compared to CH2 domain-deleted huCC49 MAb by non-reducing SDS-PAGE electrophoresis followed by Western Blot with anti-human IgG HRP conjugated antibody to detect CH2 domain deleted huCC49 Form A and Form B forms. Under these conditions, Form A migrates as a single 120 kDa homodimer and Form B as a 60 kDa doublet. Incorporation of the connecting peptide shown in SEQ ID NO: 9 was found to substantially increase the proportion of Form A produced. Exemplary results are shown in FIG. 27. This result shows that the G1/G3/Pro243Ala244Pro245+[Gly/Ser] hinge (SEQ ID NO:9) resulted in the production of essentially all Form A CH2 domain-deleted C2B8 antibody with little or no detectable Form B, demonstrating that the utility of this hinge for producing the Form A isoform is generally applicable to antibodies of varying specificities.

Example 13

Anti-CD23 Antibody Comprising a Connecting Peptide

The hinge region connecting-peptide G1/G3/Pro243Ala244Pro245+[Gly/Ser] (SEQ ID NO: 9) was used to construct a CH2 domain-deleted 5E8 (5E8ΔCH2) antibody essentially as described in Example 3. 5E8 is a chimeric anti-CD23 monoclonal antibody consisting of primate heavy and light chain variable domains fused to human heavy and light chain constant domains, respectively. Correct modifications to the hinge region were confirmed by DNA sequence analysis. Nucleic acid and amino acid sequences of 5E8 light chain and heavy chain are shown in FIGS. 28 and 29, respectively. Plasmid DNA was used to transform CHO DG44 cells for production of antibody protein.

Figure 30:
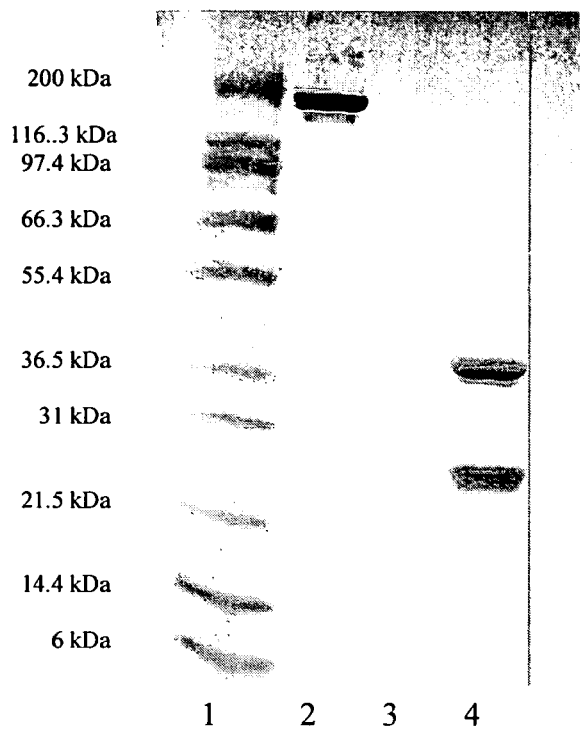
FIG. 30 shows that the inclusion of the G1/G3/Pro243Ala244Pro245+[Gly/Ser] connecting peptide (SEQ ID NO:9) into an antibody of different specificity (here the CH2 domain-deleted 5E8 antibody) results in the production of essentially all form A antibody with little or no detectable Form B (see lane 2).
Figure 31:
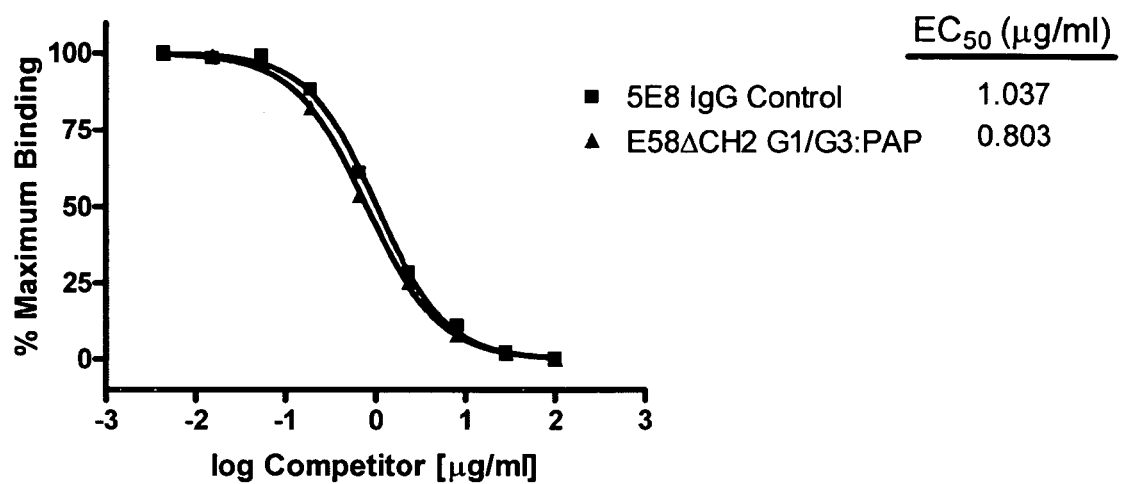
FIG. 31 shows the results of a competitive binding assay to soluble CD23 by time-resolved fluorometric immunoassay.

A cell line (1A7) containing the G1/G3/Pro243Ala244Pro245+[Gly/Ser] (SEQ ID NO:9) connecting peptide introduced into the 5E8ΔCH2 antibody sequence was used for antibody production. Antibody was produced and purified using methods described in Example 4 above. 5E8ΔCH2 G1/G3/Pro243Ala244Pro245 antibody, purified using only the Protein G column, eluted essentially as a single peak at ≧97% purity without further HIC purification. Reduced and non-reduced purified protein samples were analyzed by SDS-PAGE electrophoresis. Under non-reducing conditions, Form A is expected to migrate as a single 120 kDa homodimer and Form B as a 60 kDa doublet. The connecting peptide shown in SEQ ID NO: 9 was found to substantially increase the proportion of Form A produced. Exemplary results are shown in FIG. 30. This result shows that the G1/G3/Pro243Ala244Pro245+[Gly/Ser] hinge (SEQ ID NO:9) resulted in the production of essentially all Form A 5E8ΔCH2 antibody with little or no detectable Form B (see lane 2), demonstrating that the utility of this hinge for producing the Form A isoform is generally applicable to antibodies of varying specificities. 5E8ΔCH2 G1/G3/Pro243Ala244Pro245 antibody was examined by size exclusion chromatography and found to elute as a single peak indicating that there was no significant aggregation or decomposition of antibody product. 5E8ΔCH2 G1/G3/Pro243Ala244Pro245 antibody was further tested in a FRET (fluorescence resonance energy transfer) competitive binding assay for Cy5-labeled soluble. CD23 binding to Eu-labeled 5E8 IgG using a Delphia fluorimeter (Wallac 1420 Multilabel Counter Victor V, PerkinElmer). Competitive binding curves are shown in FIG. 31. 5E8ΔCH2 G1/G3/Pro243Ala244Pro245 (containing the connecting peptide shown in SEQ ID NO: 9), and control parent 5E8 IgG antibodies were evaluated. Relative binding activity of the hinge engineered antibody was indistinguishable from control parent 5E8 IgG antibody. From these results it is clear that introduction of the hinge region (containing the connecting peptide shown in SEQ ID NO: 9) in the 5E8ΔCH2 antibody led to the preferential synthesis of the A isoform while retaining full binding activity and supports the general utility of the engineered hinges.

Example 14 chB3F6 Antibody Comprising a Connecting Peptide

The hinge region connecting peptide G1/G3/Pro243Ala244Pro245+[Gly/Ser] (SEQ ID NO: 9) was used to construct a CH2 domain-deleted chimeric B3F6 (chB3F6ΔCH2) antibody essentially as described in Example 3. chB3F6 is a chimeric anti-CRIPTO monoclonal antibody consisting of murine heavy and light chain variable domains fused to human heavy and light chain constant domains, respectively. Correct modifications to the hinge region were confirmed by DNA sequence analysis. Nucleic acid and amino acid sequences of chB3F6 light chain and heavy chain are shown in are shown in FIGS. 32 and 33, respectively. Plasmid DNA was used to transform CHO DG44 cells for production of antibody protein.

A cell line (3C7) containing the G1/G3/Pro243Ala244Pro245+[Gly/Ser] (SEQ ID NO:9) connecting peptide introduced into the chB3F6ΔCH2 antibody sequence was used for antibody production. Antibody was produced and purified using methods described in Example 4 above. ChB3F6ΔCH2 G1/G3/Pro243Ala244Pro245 antibody, purified using only the Protein G column, eluted essentially as a single peak at 97% purity without further HIC purification.

Figure 34:
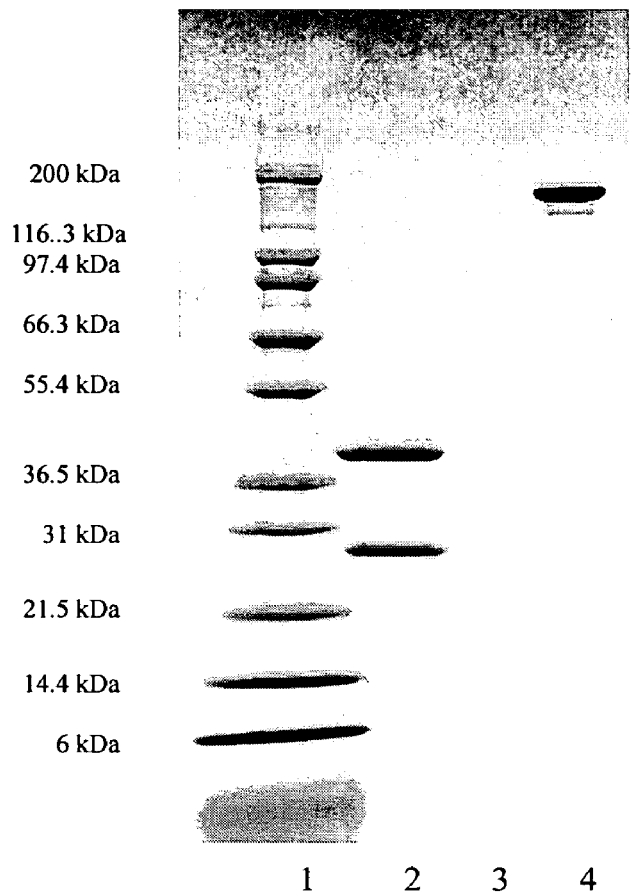
FIG. 34 shows that the inclusion of the G1/G3/Pro243Ala244Pro245+[Gly/Ser] connecting peptide (SEQ ID NO:9) into an antibody of different specificity (here the CH2 domain-deleted chB3F6 antibody) results in the production of essentially all form A antibody with little or no detectable Form B (see lane 4).
Figure 35:
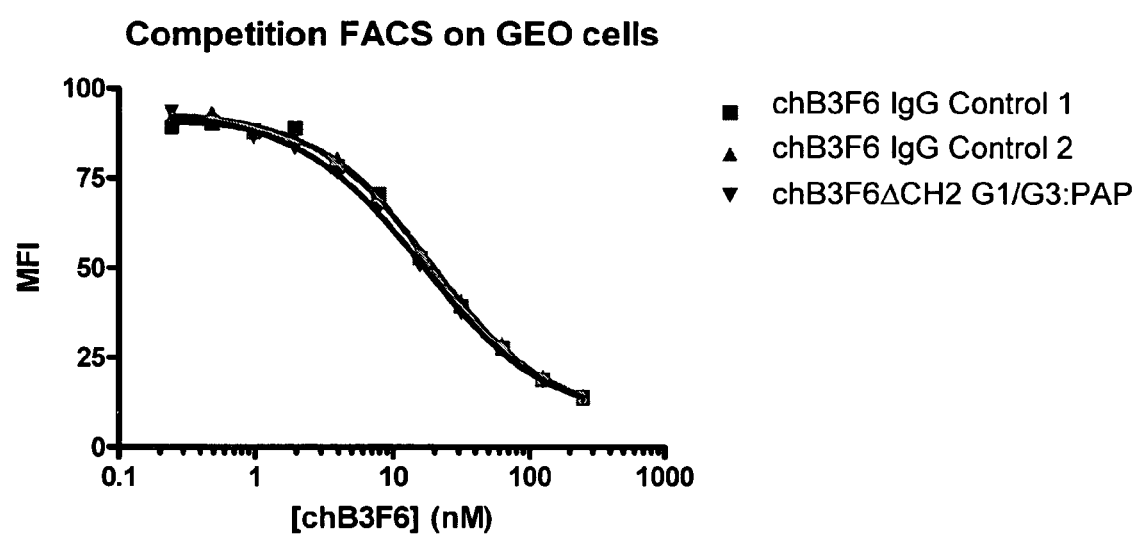
FIG. 35 shows that chimeric B3F6 (chB3F6) and chimeric B3F6 domain deleted antibody comprising a connecting peptide (B3F6ΔCH2 G1/G3/Pro243Ala244Pro245) compete equally for binding to GEO tumor cells.

Reduced and non-reduced purified protein samples were analyzed by SDS-PAGE electrophoresis. Under these conditions, Form A is expected to migrate as a single 120 kDa homodimer and Form B as a 60 kDa doublet. The connecting peptide shown in SEQ ID NO: 9 was found to substantially increase the proportion of Form A produced. Exemplary results are shown in FIG. 34. This result shows that the G1/G3/Pro243Ala244Pro245+[Gly/Ser] hinge (SEQ ID NO:9) resulted in the production of essentially all Form A chB3F6ΔCH2 antibody with little or no detectable Form B, demonstrating that the utility of this hinge for producing the Form A isoform is generally applicable to antibodies of varying specificities. ChB3F6ΔCH2 G1/G3/Pro243Ala244Pro245 antibody was examined by size exclusion chromatography and found to elute essentially as a single peak ranging from 93-98% monomer indicative of little or no significant aggregation or decomposition of antibody product. ChB3F6ΔCH2 G1/G3/Pro243Ala244Pro245 antibody was further tested in a flow cytometry competitive binding assay with FITC-labeled B3F6 IgG binding to GEO tumor cells, a source of the CRIPTO antigen. Competitive binding curves are shown in FIG. 35. ChB3F6ΔCH2 G1/G3/Pro243Ala244Pro245 (containing the connecting peptide shown in SEQ ID NO: 9), and two control samples of chB3F6 IgG antibodies were evaluated. Relative binding activity of the hinge engineered antibody was indistinguishable from the control parent chB3F6 IgG antibodies. From these results it is clear that introduction of the hinge region (containing the connecting peptide shown in SEQ ID NO: 9) in chB3F6ΔCH2 antibody led to the preferential synthesis of the A isoform while retaining full binding activity and further supports the general utility of the engineered hinges.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising polypeptide dimers having at least two antigen binding sites and at least two polypeptide chains, wherein said at least two polypeptide chains each comprise a complete Ig heavy chain, and a chimeric hinge,
wherein said chimeric hinge connects the CH1 and the CH2 domain of the Ig heavy chain, and
wherein greater than 50% of the polypeptide dimers comprise polypeptide chains that are linked via at least one interchain disulfide linkage, and
wherein amino acids at positions 226-242 (Kabat numbering) comprise: (i) the human IgG1 upper hinge region sequence EPKSCDKTHT (SEQ ID NO:2) or the human IgG4 upper hinge region sequence ESKYGPP (SEQ ID NO:50) at Kabat hinge positions 226-238; (ii) a cysteine residue (C) at Kabat hinge position 239; (iii) a proline residue (P) at Kabat hinge position 240; (444 iv) a proline (P) or serine (5) residue at Kabat hinge position 241; (v) the human IgG3 middle hinge sequence CPEPKSCDTPPPCPR (SEQ ID NO:37) at Kabat hinge positions 241EE-241SS; and (vi) a cysteine residue (C) at Kabat hinge position 242.

2. The composition of claim 1, wherein greater than 90% of the polypeptide dimers are linked via at least one interchain disulfide linkage.

3. The composition of claim 1, wherein the chimeric hinge further comprises a gly-ser linker.

4. The composition of claim 3, wherein the gly-ser linker consists of the amino acid sequence GGGSSGGGSG (SEQ ID NO:1).

5. The composition of claim 1, wherein the polypeptide dimers are linked via two or more interchain disulfide linkages.

6. The composition of claim 1, wherein the heavy chain is from an antibody of an isotype selected from the group consisting of: IgG1, IgG2, IgG3, and IgG4.

7. The composition of claim 1, wherein the polypeptide dimers comprise four polypeptide chains and wherein two of the polypeptide chains comprise at least one heavy chain and a chimeric hinge.

8. The composition of claim 1, wherein at least one antigen binding site binds to an antigen expressed by tumor cells.

9. The composition of claim 1 wherein the chimeric hinge is the amino acid sequence of SEQ ID NO:8.

10. The composition of claim 1, wherein the chimeric hinge is the amino acid sequence of SEQ ID NO:9.

11. The composition of claim 1, wherein the chimeric hinge is the amino acid sequence of SEQ ID NO:53.

12. A connecting peptide comprising the amino acid sequence SEQ ID NO:8.

13. A connecting peptide comprising the amino acid sequence SEQ ID NO:9.

14. A connecting peptide comprising the amino acid sequence SEQ ID NO:10.

15. A connecting peptide comprising the amino acid sequence SEQ ID NO:11.

16. A connecting peptide comprising the amino acid sequence SEQ ID NO:12.

17. A connecting peptide comprising the amino acid sequence SEQ ID NO:13.

18. A connecting peptide comprising the amino acid sequence SEQ ID NO:14.

19. A connecting peptide comprising the amino acid sequence SEQ ID NO:15.

20. A connecting peptide comprising the amino acid sequence SEQ ID NO:53.

21. A connecting peptide consisting of the amino acid sequence SEQ ID NO:7.

22. A connecting peptide consisting of amino acid sequence SEQ ID NO:8.

23. A connecting peptide consisting of amino acid sequence SEQ ID NO:9.

24. A connecting peptide consisting of amino acid sequence SEQ ID NO:10.

25. A connecting peptide consisting of amino acid sequence SEQ ID NO:11.

26. A connecting peptide consisting of amino acid sequence SEQ ID NO:12.

27. A connecting peptide consisting of amino acid sequence SEQ ID NO:13.

28. A connecting peptide consisting of amino acid sequence SEQ ID NO:14.

29. A connecting peptide consisting of amino acid sequence SEQ ID NO:15.

30. A connecting peptide consisting of amino acid sequence SEQ ID NO:53.

31. A composition comprising polypeptide dimers having at least two antigen binding sites and at least two polypeptide chains, wherein said at least two polypeptide chains each comprise (i) an Ig heavy chain lacking modified to lacking a CH2 domain, and (ii) a synthetic connecting peptide comprising a chimeric hinge,
  wherein said connecting peptide is selected from the group consisting of SEQ ID NO: 7-15 and 53 and wherein said connecting peptide connects said heavy chain to at least one of said binding sites, and
  wherein greater than 50% of the polypeptide dimers comprise polypeptide chains that are linked via at least one interchain disulfide linkage.

32. The composition of claim 6, wherein the heavy chain is from an IgG3 molecule.

33. The composition of claim 6, wherein the heavy chain is from an IgG4 molecule.

34. The composition of claim 31, wherein greater than 90% of the polypeptide dimers are linked via at least one interchain disulfide linkage.

35. The composition of claim 31, wherein the heavy chain is from an antibody of an isotype selected from the group consisting of IgG1, IgG2, IgG3, and IgG4.

36. The composition of claim 31, wherein the polypeptide dimers comprise four polypeptide chains and wherein two of the polypeptide chains comprise at least one heavy chain and a synthetic connecting peptide.

37. The composition of claim 31, wherein at least one antigen binding site binds to an antigen expressed by tumor cells.

38. The composition of claim 31, wherein the heavy chain is from an antibody of an IgG3 isotype.

* * * * *

UNITED STATES PATENT AND TRADEMARK OFFICE
CERTIFICATE OF CORRECTION

PATENT NO. : 7,700,097 B2
APPLICATION NO. : 10/880320
DATED : April 20, 2010
INVENTOR(S) : Gary R. Braslawsky et al.

It is certified that error appears in the above-identified patent and that said Letters Patent is hereby corrected as shown below:

At column 127, line 39 (Claim 1), of the printed patent, please change "(444 iv)" to --(iv)--.

At column 127, line 40 (Claim 1), of the printed patent, please change "(5)" to --(S)--.

At column 129, line 4 (Claim 31), of the printed patent, please remove "modified to lacking".

Signed and Sealed this

Twentieth Day of July, 2010

David J. Kappos
*Director of the United States Patent and Trademark Office*